(12) United States Patent
Szardenings et al.

(10) Patent No.: US 7,662,782 B2
(45) Date of Patent: *Feb. 16, 2010

(54) MELANOCORTIN 1 RECEPTOR SELECTIVE COMPOUNDS

(75) Inventors: Michael Szardenings, Wolfenbüttel (DE); Ruta Muceniece, Uppsala (SE); Ilze Mutule, Uppsala (SE); Felikss Mutulis, Uppsala (SE); Jarl Wikberg, Sigtuna (SE)

(73) Assignee: Action Pharma A/S, Arhus N (DK)

( * ) Notice: Subject to any disclaimer, the term of this patent is extended or adjusted under 35 U.S.C. 154(b) by 7 days.

This patent is subject to a terminal disclaimer.

(21) Appl. No.: 11/319,584

(22) Filed: Dec. 29, 2005

(65) Prior Publication Data

US 2007/0027086 A1 Feb. 1, 2007

Related U.S. Application Data

(63) Continuation of application No. 09/674,733, filed as application No. PCT/GB99/01388 on May 5, 1999, now Pat. No. 7,008,925.

(30) Foreign Application Priority Data

May 5, 1998 (SE) .................................... 9801571

(51) Int. Cl.
*A61K 38/00* (2006.01)

(52) U.S. Cl. .......................... 514/13; 514/12; 514/14; 514/15

(58) Field of Classification Search .................. None
See application file for complete search history.

(56) References Cited

U.S. PATENT DOCUMENTS

| 4,288,627 A | 9/1981 | Kubicek |
| 5,731,408 A | 3/1998 | Hadley et al. ............... 530/317 |
| 2009/0069242 A1 | 3/2009 | Jonassen |

FOREIGN PATENT DOCUMENTS

| WO | 91 17243 | 11/1991 |
| WO | 9511988 | 5/1995 |
| WO | 9946283 | 9/1999 |
| WO | 99 57148 | 11/1999 |
| WO | 01 04156 | 1/2001 |
| WO | 01 36980 | 5/2001 |
| WO | 01 90140 | 11/2001 |

OTHER PUBLICATIONS

Bagutti, C. et al., "[$^{111}$In]-DTPA-Labeled Analogues of α-Melanocyte-Stimulating Hormone for Melanoma Targeting: Receptor Binding In Vitro and In Vivo," *Int. J. Cancer* 58:749-755, Wiley-Liss, Inc. (1994).

Bhardwaj, R.S. et al., "Pro-Opiomelanocortin-Derived Peptides Induce IL-10 Production in Human Monocytes," *J. Immunol.* 156:2517-2521, The American Association of Immunologists (1996).

Cone, R.D. et al., "The Melanocortin Receptors: Agonists, Antagonists, and the Hormonal Control of Pigmentation," *Recent Prog. Horm. Res.* 51:287-317, The Endocrine Society (1996).

De Wied, D. and Jolles, J., "Neuropeptides Derived From Pro-Opiocortin: Behavioral, Physiological, and Neurochemical Effects," *Physiol. Rev.* 62:976-1059, The American Physiological Society (1982).

Eberle, A.N., "Structure-Activity Relationships of the Melanotropins," in *The Melanotropins: Chemistry, Physiology and Mechanisms of Action*, Eberle, A.N., Ed., S. Karger Publishing, Basel, Switzerland, pp. 333-379 (1988).

Gonindard, C. et al., "The Administration of an α-MSH Analogue Reduces the Serum Release of IL-1α and TNFα Induced by the Injection of a Sublethal Dose of Lipopolysaccharides in the BALB/c Mouse," *Pigment Cell Res.* 9:148-153, Munksgaard (1996).

Gruber, K.A. and Callahan, M.F., "ACTH-(4-10) through γ-MSH: evidence for a new class of central autonomic nervous system-regulating peptides," *Am. J. Physiol.* 257:R681-R694, The American Physiological Society (1989).

Hartmeyer, M. et al., "Human Dermal Microvascular Endothelial Cells Express the Melanocortin Receptor Type 1 and Produce Increased Levels of IL-8 upon Stimulation with α-Melanocyte-Stimulating Hormone," *J. Immunol.* 159:1930-1937, The American Association of Immunologists (Aug. 1997).

Hnatowich, M.R. et al., "ACTH receptors in nervous tissue. High affinity binding-sequestration of [$^{125}$I] [Phe$^2$,Nle$^4$]ACTH 1-24 in homogenates and slices from rat brain," *Can. J. Physiol. Pharmacol.* 67:568-576, National Research Council of Canada (1989).

(Continued)

*Primary Examiner*—Cecilia Tsang
*Assistant Examiner*—Marcela M Cordero Garcia
(74) *Attorney, Agent, or Firm*—Stanislaus Aksman Roberts Mlotkowski Safran & Cole P.C.

(57) ABSTRACT

The invention relates to methods of treatment comprising administering a compound of the general formula (1):

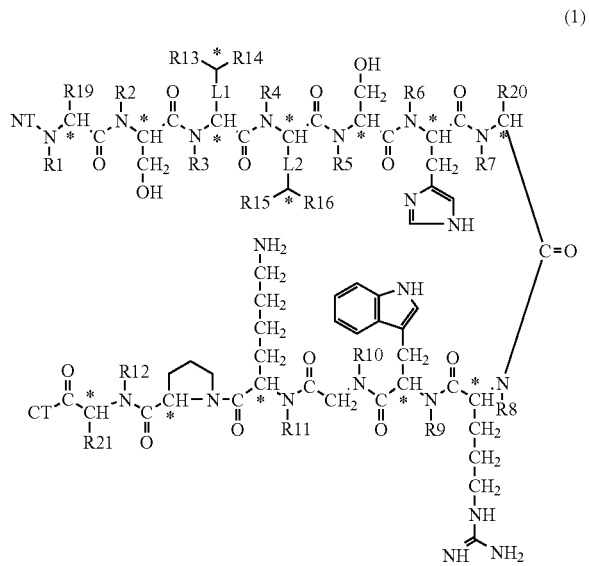

to a patient or a healthy individual.

39 Claims, 6 Drawing Sheets

OTHER PUBLICATIONS

Hol, E.M. et al., "Protection by an ACTH$_{4-9}$ Analogue Against the Toxic Effects of Cisplatin and Taxol on Sensory Neurons and Glial Cells In Vitro," *J. Neurosci. Res.* 39:178-185, Wiley-Liss, Inc. (1994).

Hruby, V.J. et al., "Cyclic Lactam α-Melanotropin Analogues of Ac-Nle$^4$-cyclo[Asp$^5$,D-Phe$^7$,Lys$^{10}$] α-Melanocyte-Stimulating Hormone-(4-10)-NH$_2$ with Bulky Aromatic Amino Acids at Position 7 Show High Antagonist Potency and Selectivity at Specific Melanocortin Receptors," *J. Med. Chem.* 38:3454-3461, American Chemical Society (1995).

Klein, M.C. et al., "Pressor and Cardioaccelerator Effects of Gamma MSH and Related Peptides," *Life Sci.* 36:769-775, Pergamon Press (1985).

Knittel, J.J. et al., "Structure-Activity Studies of Highly Potent Cyclic [Cys$^4$,Cys$^{10}$]Melanotropin Analogues," *J. Med. Chem.* 26:125-129, American Chemical Society (1983).

Lichtensteiger, W. et al., "Pre- and Postnatal Ontogeny of [$^{125}$I]Nle$^4$,D-Phe$^7$-α-MSH Binding Sites in Rat Brain," *Ann. N.Y. Acad. Sci.* 680:652-654, New York Academy of Sciences (1993).

Lin, S.-Y., et al. "A γ-Melanocyte Stimulating Hormone-like Peptide Causes Reflex Natriuresis After Acute Unilateral Nephrectomy," *Hypertension* 10:619-627, American Heart Association (1987).

Murphy, J.R. et al., "Genetic construction, expression and melanoma-selective cytotoxicity of a diphtheria toxin-related α-melanocyte-stimulating hormone fusion protein," *Proc. Natl. Acad. Sci. USA* 83:8258-8262, National Academy of Sciences (1986).

Prusis, P. et al., "A Three Dimensional Model for the Interaction of MSH with the Melanocortin-1 Receptor," *Biochem. Biophys. Res. Commun.* 210:205-210, Academic Press, Inc. (1995).

Sawyer, T.K. et al., "4-Norleucine, 7-D-phenylalanine-α-melanocyte-stimulating hormone: A highly potent α-melanotropin with ultralong biological activity," *Proc. Natl. Acad. Sci. USA* 77:5754-5758, National Academy of Sciences (1980).

Sawyer, T.K. et al., "[half-Cys$^4$,half-Cys$^{10}$]-α-Melanocyte-stimulating hormone: A cyclic α-melanocyte exhibiting superagonist biological activity," *Proc. Natl. Acad. Sci. USA* 79:1751-1755, National Academy of Sciences (1982).

Tatro, J.B. et al., "Interaction of an α-Melanocyte-stimulating Hormone-Diphtheria Toxin Fusion Protein with Melanotropin Receptors in Human Melanoma Metastases," *Canc. Res.* 52:2545-2548, American Association for Cancer Research (1992).

Thielemans, K.M.M., "Immunotherapy with Bispecific Antibodies," *Verh. K. Acad. Geneeskd. Belg.* 57:229-248, Paleis Der Academein (1995).

Wiegant, V.M. et al., "Intracerebroventricular ACTH Activates the Pituitary-Adrenal System:Dissociation from a Behavioral Response," *Life Sci.* 25:1791-1796, Pergamon Press (1979).

Schiöth, H.B. et al., "Binding and cyclic and linear MSH core peptides to the melanocortin receptor subtypes," *European Journal of Pharmacology* 319:369-373, Elsevier Science B.V. (Feb. 1997).

Szardenings, M. et al., "Phage Display Selection on Whole Cells Yields a Peptide Specific for Melanocortin Receptor 1," *J. Biol. Chem.* 272: 27943-27948, The American Society for Biochemistry and Molecular Biology, Inc. (Oct. 1997).

Abstract of Larsen et at: "Structural inducing probes (SIP)—blow new hope into the general use of peptides as drugs", Abstract from Peptides 2000, Proceedings of the European Peptide Symposium 26th.

Catania, A., Rajora, F., Capsoni, F., Minonzio, R.A., Star, and Lipton, J.M. "The Neuropeptide alpha-MSH Has Specific Receptors on Neutrophils and Reduces Chemotaxis in Vitro" Peptides 17: No. 4 675-679, 1996.

Ehrlich, "DNA cloning in bacilluas subtilis" 1978, Proc. Natl. Acad. Sci. USA 75 (1978) (3):1433).

Guo and Sherman, "3'-end-forming signals of yeast mRNA" 1995, Molecular and Cellular Biology 15:(2) 5983-5990.

Hartmeyer, M., Scholzen T., Becher E, Bhardwaj R.S., Schwarz T. and Luger LA., "Human Dermal Microvascular Endothelial Cells Express the Melanocortin Receptor Type 1 and Produce Increased Levels of IL-8 upon Stimulation with alpha-Melanocyte-Stimulating Hormone" J.Immunol., 159: (4)1930-1937, 1997.

Kullmann, W. 1987, "Proteases as Biocatalysts For The Synthesis of Model Peptides", Enzymatic Peptide Synthesis, CRC Press, Boca Raton, Florida, Chapter 7, pp. 41-59.

Lipton, J.M and Catania, A. "Anti-inflammatory actions of the neuroimmunomodulator alpha-MSH" Immunol. Today 18: (3) 140-145. 1997.

Liu et al., 1996., "Orthogonal Ligation of Unprotected Peptide Segments through Pseudoproline Formation for the Synthesis of HIV-1 Protease Analogs", J. Am. Chem. Soc. 118:307-312.

Luger, T.A., Scholzen T. and Grabbe S., "The role of alpha-metanocyte-stimulating hormone in cutaneous biology", J.Investig. DermatoLSymp.Proc., 2: 87-93, 1997.

Rajora, N., Boccoli, G., Catania and Lipton J.M., "alpha-MSH Modulates Experimental Inflammatory Bowel Disease", Peptides, 18: 381-385, 1997.

Romanos et al., "Foreign gene expression in yeast: a review", 1992, Yeast 8:423-488.

Star, R.A.,Rajora N., Huang J., Stock R.C., Catania A. and Lipton J.M.; "Evidence of autocrine modulation of macrophage nitric oxide synthase by alpha-melanocyte-stimulating hormone", Proc. Natl. Acad.Sci. U.S.A, 92: 8016-8020, 1995.

Wong, K.Y., Rojora, G., Boccoli, A., Catania, A., and Lipton J.M., "A Potential Mechanism of Local Anti-Inflammatory Action of Alpha-Melanocyte-Stimulating Hormone within the Brain: Modulation of Tumor Necrosis Factor-Alpha Production by Human Astrocytic Cells" Neuroimmunomodulation, 4: 37-41,1997.

"Useful proteins from recombinant bacteria" in Scientific American,1980, 242:74-94.

Hruby, Victor J. et al: "Cyclic Lactam α-Melanotropin Analogues of Ac-Nle4-cyclo[Asp51D-Phe7,Lys~°] α-Melanocyte-Stimulating Hormone-(4-10)-NH2 with Bulky Aromatic Amino Acids at Position 7 Show High Antagonist Potency and Selectivity at Specific MelanocortinReceptors", J. Med. Chem. 1995, 38, 3454-3461. Received May 18, 1995.

Rizzi, Anna et al: "Pharmacological characterization of the novel nociceptin/orphanin FQ receptor ligand, ZP12O: in vitro and in vivo studies in mice", British Journal of Pharmacology (2002) 137, 369-374.2002.

SchiOth, Helgi B. et al: "Selective properties of C-and N-terminals and core residues of the melanocyte-stimulating hormone on binding to the human melanocortin receptor subtypes", European Journal of Pharmacology 349 (1998) 359-366. Received Feb. 2, 1998; revised Mar. 9, 1998; accepted Mar. 10, 1998.

Hiltz, M.E. et al: "Anti-Inflammatory Activity of α-MSH(11-13) Analogs: Influences of Alteration in Stereochemistry", Peptides vol. 12, pp. 767-771. Received Mar. 4, 1991.

Szardenings, Michael et al: "New highly specific agonistic peptides for human melanocortin MC1 receptor", Peptides 21 (2000) 239-243. Received Aug. 9, 1999; accepted Oct. 28, 1999.

Sawyer, Tomi K et at: "4-Norleucine, 7-D-phenylalanine-α-melanocyte-stimutating homone: A highly potent α-melanotropin with ultratong biological activity", Proc. Natl. Sci. USA vol. 77 No. 10, pp. 5754-5758, Oct. 1980 Biochemistry. Jul. 7, 1980.

U.S. Appl. No. 09/341,590, filed Jul. 13, 1999 application as filed and Amendment of Feb. 12, 2009.

Schioth, H. B. et al., "Binding of cyclic and linear MSH core petides to the melanocortin receptor subtypes" European Journal of Pharmacology 319: 369-373, Elvester Science B.V. (Feb. 1997).

Szardenings, M. et al., "Phage Display Selection on Whole Cells Yields a Peptide Specific for Melanocortin Receptor 1," J. Biol. Chem. 272: 27943-27948, The American Society for Biochemistry and Molecular Biology, Inc. (Oct. 1997).

Szardenings et al. 1997. Journal of Biol. Chem. vol. 272, No. 44, pp. 27943-27948.

Bagutti, C. et al., "[.sup.111In] -DTPA-Labeled Analogues of .alpha.-Melanocyte-Stimulating Hormone for Melanoma Targeting: Receptor Binding In Vitro and In Vivo," Int. J. Cancer 58:749-755, Wiley-Liss, Inc. (1994).

Bhardwaj, R.S. et al., "Pro-Opiomelanocortin-Derived Peptides Induce IL-10 Production in Human Monocytes," Immunol. 156:2517-2521, The American Association of Immunologists (1996).

Cone, R.D. et al., "The Melancortin Receptors: Agonists, Antagonists, and the Hormonal Control of Pigmentation," Recent Prog. Horm. Res. 51:287-317, The Endocrine Society (1996).

De Wied, D. and Jolles, J., "Neuropeptides Derived From Pro-Opiocortin: Behavioral, Physiological, and Neurochemical Effects," Physiol. Rev. 62:976-1059, The American Physiological Society (1982).

Eberle, A.N., "Structure-Activity Relationships of the Melanotropins," in The Melanotropins: Chemistry, Physiology and Mechanisms of Action, Eberle, A.N., Ed., S. Karger Publishing, Basel, Switzerland, pp. 333-379 (1988).

Gonindard, C. et al., "The Administration of an .alpha.-MSH Analogue Reduces the Serum Release of IL-1.alpha. and TNF.alpha. Induced by the Injection of a Sublethal Dose of Lipopolysaccharides in the BALB/c Mouse," Pigment Cell Res. 9:148-153, Munksgaard (1996).

Gruber, K.A. and Callahan, M.F., "ACTH-(4-10) through .gamma.-MSH: evidence for a new class of central autonomic nervous system-regulating peptides," Am. J. Physiol. 257:R681-R694, The American Physiological Society (1989).

Hartmeyer, M. et al., "Human Dermal Microvascular Endothelial Cells Express the Melanocortin Receptor Type 1 and Produce Increased Levels of IL-8 upon Stimulation with .alpha.-Melanocyte-Stimulating Hormone," J. Immunol. 159:1930-1937, The American Association of Immunologists (Aug. 1997).

Hnatowich, M.R. et al., "ACTH receptors in nervous tissue. High affinity binding-sequestration of [.sup.125I] [Phe. sup.2,Nle.sup.4] ACTH 1-24 in homogenates and slices from rat brain," Can. J. Physiol. Pharmacol. 67:568-576, National Research Council of Canada (1989).

Hol, E.M. et al., "Protection by an ACTH.sub.4-9 Analogue Against the Toxic Effects of Cisplatin and Taxol on Sensory Neurons and Glial Cells In Vitro," J. Neurosci. Res. 39:178-185, Wiley-Liss, Inc. (1994).

Klein, M.C. et al., "Pressor and Cardioaccelerator Effects of Gamma MSH and Related Peptides," Life Sci. 36:769-775, Pergamon Press (1985).

Knittel, J.J. et al., "Structure-Activity Studies of Highly Potent Cyclic [Cys.sup.4,Cys.sup.10]Melanotropin Analogues," J. Med. Chem. 26:125-129, American Chemical Society (1983).

Lichtensteiger, W. et al., "Pre- and Postnatal Ontogeny of [.sup.125I]Nle.sup.4,D-Phe.sup.7-.alpha.-MSH Binding Sites in Rat Brain," Ann. N.Y. Acad. Sci. 680:652-654, New York Academy of Sciences (1993).

Lin, S.-Y., et al. "A .gamma.-Melanocyte Stimulating Hormone-like Peptide Causes Reflex Natriuresis After Acute Unilateral Nephrectomy," Hypertension 10:619-627, American Heart Association (1987).

Murphy, J.R. et al., "Genetic construction, expression and melanoma-selective cytotoxicity of a diphtheria toxin-related .alpha.-melanocyte-stimulating hormone fusion protein," Proc. Natl. Acad. Sci. USA 83:8258-8262, National Academy of Sciences (1986).

Prusis, P. et al., "A Three Dimensional Model for the Interaction of MSH with the Melanocortin-1 Receptor," Biochem. Biophys. Res. Commun. 210:205-210, Academic Press Inc. (1995).

Sawyer, T.K. et al., "[half-Cys.sup.4,half-Cys.sup.10] -.alpha.-Melanocyte-stimulating hormone: A cyclic .alpha.-melanotropin exhibiting superagonist biological activity," Proc. Natl. Acad. Sci. USA 79:1751-1755, National Academy of Sciences (1982).

Tatro, J.B. et al., "Interaction of an .alpha.-Melanocyte-stimulating Hormone-Diphtheria Toxin Fusion Protein with Melanotropin Receptors in Human Melanoma Metastases," Canc. Res. 52:2545-2548, American Association for Cancer Research (1992).

Thielemans, K.M.M., "Immunotherapy with Bispecific Antibodies," Verh. K. Acad. Geneeskd. Belg. 57:229-248, Paleis Der Academein (1995).

Wiegant, V.M. et al., "Intracerebroventricular ACTH Activates the Pituitary-Adrenal System:Dissociation from a Behavioral Response," Life Sci. 25:1791-1796, Pergamon Press (1979).

Schioth, H.B. et al., "Binding of cyclic and linear MSH core peptides to the melanocortin receptor subtypes," European Journal of Pharmacology 319:369-373, Elsevier Science B.V. (Feb. 1997).

Boyfield, I, Winn F & Coldwell M: Comparison of agonist potencies at human dopamine D2 and D3 receptors, expressed in the same cell line, using the Cytosensor Microphysiometer. Biochem. Soc. Trans. 1996, 24, 57S.

Campbell, M. J.: Lipofection reagents prepared by a simple ethanol injection technique. Biotechniques 1995, 18, No. 6, 1027-32.

Canevari, S, Mezzanzanica D, Mazzoni A, Negri D R, Ramakrishna V, Bolhuis R L, Colnaghi M I & Bolis G: Bispecific antibody targeted T cell therapy of ovarian cancer: clinical results and future directions. J. Hematother. 1995, 4, 423-427.

Adan, R A H, Oosterom J, Ludviksdottir G, Brakkee J H, Burbach J P H, Gispen W H, 1994, Identification of antagonists for melanocortin MC3, MC4 and MC5 receptors. Eur. J. Pharmacol. (1994) 269, 331-337.

Luger et al. "alfa-MSH related peptides: a new class of anti-inflammattory and immunomodulating drugs" Ann Rheum Dis 2007; 66 (Suppl III):iii52-iii55.doi:10.1136/ard.2007.079780.

Simpson, E R and Waterman M R, Regulation of the synthesis of steroidogenic enzymes in adrenal cortical cells by ACTH. (1988) Ann. Rev. Physiol. 50, 427-440.

Garrud, P, Gray J A & DeWied D: Pituitary-adrenal hormones and extinction of rewarded behavior in the rat. Physiol Psychol. 1974, 112, 109-119.

O'Donahue, T L, Handelmann G E, Loh Y P, Olton D S, Leibowitz J & Jacobowitz D M: Comparison of biological and behavioral activities of alpha- and gamma melanocyte stimulating hormones. Peptides 1981, 2, 101-104.

O'Donahue, T L, & Dorsa D M: The opiomelanotropinergic neuronal and endocrine systems. Peptides 1982, 3, 353-395.

Feng, J D, Dao T & Lipton J M: Effects of preoptic microinjections of MSH on fever and normal temperature control in rabbits. Brain Res. 1987, 18, 473-477.

De Wildt, D J, Kasbergen C M & Versteeg D H G: Effect of—melanocyte-stimulating hormone on cerebral blood flow in rats. J Cardiovascular Pharmacology 1995, 25, 898-905.

Friedman, J M: The alphabet of weight control. Nature 1997, 385, 119-120.

Chhajlani, V, Muceniece R and Wikberg J E S, 1993, Molecular cloning of a novel human melanocortin receptor, Biochem. Biophys. Res. Commun. 195, 866.

Chhajlani, V and Wikberg J E S, 1992, Molecular cloning and expression of the human melanocyte stimulating hormone receptor cDNA, FEBS Lett. 309, 417.

Gantz, I, Konda Y, Tashiro T, Shimoto Y, Miwa H, Munzert G, Watson S J, DelValle J and Yamada T, 1993a, Molecular cloning of a novel melanocortin receptor, J. Biol. Chem. 268, 8246.

Gantz, I, Miwa H, Konda Y, Shimoto Y, Tashiro T, Watson S J, DelValle J and Yamada T, 1993b, Molecular cloning, expression, and gene localization of a fourth melanocortin receptor, J. Biol. Chem. 268, 15174.

Mountjoy, K G, Robbins L S, Mortrud M T and Cone R D, 1992, The cloning of a family of enes that encode the melanocortin receptors, Science 257, 1248.

Low, M J, Simerly R B, Cone R D, 1994, Receptors for the melanocortin peptides in the central nervous system, Curr. Opin. Endocr. Diab. 79.

Siegrist, W and Eberle A N, 1995, Melanocortins and their implications in melanoma, TEM, 6, 115.

Xia, Y, Wikberg J E S & Chhajlani V: Expression of melanocortin 1 receptor in periaqueductal gray matter. Neuroreport. 1995, 6, 2193-2196.

Vanetti, M, Schönrock C, Meyerhof W & Höllt V: Molecular cloning of a bovine MSH receptor which is highly expressed in the testis. FEBS Lett. 1994, 348, 268-272.

Rajora, N, Boccoli G, Burns D, Sharma S, Catania A P & Lipton J M: Alpha-MSH modulates local and circulating tumour necrosis factor-alpha in experimental brain inflammation. J. Neurosci. 1997a, 17, 2181-2186.

Thörnvall, M, Dimitrou A, Xu X, Larsson E & Chhajlani V: Immunohistochemical detetion of the melanocortin 1 receptor in human testis, ovary and placenta using specific monoclonal antibody. Horm. Res. 1997, 48, 215-218.

Gantz, I, Shimoto Y, Konda Y, Miwa H, Dickinson C J & Yamada T: Molecular cloning, expression, and characterization of fifth melanocortin receptor. Biochem. Biophys. Res. Commun. 1994, 200, 1214-1220.

Griffon, N, Mignon V, Facchinetti P, Diaz J, Schwartz J-C & Sokoloff P: Molecular cloning and characterization of the fifth melanocortin receptor. Biochem. Biophys. Res. Commun. 1994, 200, 1007-1014.

Labbe et al. 1994: Labbé, O, Desarnaud F, Eggerickx D, Vassart G & Parmentier M: Molecular cloning of a mouse melanocortin 5 receptor gene widely expressed in peripheral tissues. Biochemistry 1994, 33, 4543-4549.

Barrett, P, MacDonald A, Helliwell R, Davidsson G & Morgan P: Cloning and expression of a member of the melanocyte-stimulating hormone receptor family. J. Mol. Endocrinology. 1994, 12, 203-213.

Fathi, Z, Iben L G & Parker E M: Cloning, expression, and tissue distribution of a fifth melanocortin receptor subtype. Neurochem Res. 1995, 20, 107-113.

Chhajlani, V, 1996, Distribution of cDNA for melanocortin receptor subtypes in human tissues, Biochem. Biophys. Res. Commun. 38, 73-80.

Schiöth, H B, Muceniece R, Wikberg J E S and Chhajlani V, 1995, Characterisation of melanocortin receptor subtypes by radioligand binding analysis, Eur. J. Pharmacol., Mol. Pharm. Sect. 288, 311.

Schiöth, H B, Kuusinen A, Muceniece R, Szardenings M, Keinänen K and Wikberg J E S, 1996a, Expression of functional melanocortin 1 receptors in insect cells, Biochem. Biophys. Res. Commun. 221, 807.

Schiöth, H B, Muceniece R and Wikberg J E S, 1996b, Characterisation of melanocortin 4 receptor by radioligand binding analysis. Pharmacol. & Toxicol. 79, 161.

Schiöth, H B, Chhajlani V, Muceniece R, Klusa V and Wikberg J E S, 1996c, Major pharmacological distinction of the ACTH receptor from the other melanocortic receptors, Life Sciences 59, 797.

Goninard, C, Goigoux C, Hollande L D & D'Hinterland L D: The administration of an alpha-MSH analogue reduces the serum release of IL-1 alpha and TNF alpha induced by the injection of a sublethal dose of lipopolysaccharides in the BALB/c mouse. Pigment Cell Res. 1996, 9, 148-153.

Desarnaud, F, Labbé O, Eggerickx D, Vassart G & Parmentier M: Molecular cloning, functional expression and pharmacological characterization of a mouse melanocortin receptor gene. Biochem J. 1994, 299, 367-373.

Zlokovic, B,V: "Cerebrovascular Permiability to peptides: Manipulations of Transport Systems at the Blood Brain Barrier" Pharmaceutical Res. 1995, 12: 1395 1406.

Fan, W, Boston B A, Kesterson R A, Hruby V J & Cone R D: Role of melanocortinergic neurons in feeding and the agouti obesity syndrome. Nature. 1997, 385, 165-168.

Feng, J D, Dao T & Lipton J M: Effects of preoptic microinjections of -MSH on fever and normal temperature control in rabbits. Brain Res. 1987, 18, 473-477.

Pardridge, W M "Recent Developments in Peptide Drug Delivery Into the Brain": Pharmacol. Toxicol. 1992, 71, 3-10.

Mountjoy, K G, Robbins L S, Mortrud M T and Cone R D, 1992, The cloning of a family of enes that encode the melanocortin receptors, Science 257, 1248.

Mountjoy, K G, Mortrud M T, Low M J, Simerly R B & Cone R D: Localization of the melanocortin-4 receptor (MC4-R) in endocrine and autonomic control circuits in the brain. Molecular Endocrinology 1994, 8, 1298-1308.

Mukherji, B & Chakraborty N G: Immunobiology and immunotherapy of melanoma. Curr. Opin. Oncol. 1995, 7, 159-161.

Nordstedt, C, Fredholm B B.: A modification of a protein binding method for rapid quantification of cAMP in cell culture supernatants and body fluid. Anal. Biochem. 1990, 189, 231 234.

O'Hare, K B, Duncan R, Strohalm J, Ulbrich K & Kopeckova P: Polymeric drug-carriers containing doxorubicin and melanocyte-stimulating hormone: in vitro and in vivo evaluation against murine melanoma. J Drug Target 1993, 1, 217-229.

Riedle, S, Rosel M & Zoller M: In vivo activation and expansion of T cells by a bi-specific antibody abolishes metastasis formation of human melanoma cells in SCID mice. Int. J. Cancer 1998, 75, 908-918.

Roselli-Rehfuss, L, Mountjoy K G, Robbins L S, Mortrud M T, Low M J, Tatro J B, Entwistle M L, Simerly R B and Cone R D: Identification of a receptor for g melanotropin and other proopiomelanocortin peptides in the hypothalamus and limbic system. Proc. Natl. Acad. Sci. USA 1993, 90, 8856-8860.

Soica, F F, Chluba de Tapia J, Iwata K, Eberle A N: B16 G4F mouse melanoma cells: an MSH receptor deficient cell clone. Febs Lett. 1993, 322, 177 80.

Xia "Immunological localization of melanocortin 1 receptor on the cell surface of WM 266-4 human melanoma cells" Cancer Letter 98 (1996) 157-162.

Tatro, J and Entwistle M L, 1994, Heterogeneity of brain melanocortin receptors suggested by differential ligand binding in situ., Brain Research 635, 148.

Toth, I "A Novel Chemical Approach to Drug Delivery: Lipidic Amino Acid Conjugates" Journal of Drug Targeting, 1994, vol. 2, pp. 217 239.

Patel et al., "Peptide Targeting and Delivery across the Blood-Brain Barrier Utilizing Symthetic Triglyceride Esters: Design, Synthesis, and Bioactivity" Bioconjugate Chem 1997, 8, 434-411.

Saito, Y et al.: "Vector-mediated delivery of 125 I-labeled β-amyloid peptide Aβ 1-40 through the blood-brain barrier and binding to Alzheimer disease amyloid of the Aβ 1-40/vector complex" Proc. Natl. Acad. Sci USA 1995, vol. 92, pp. 10227-10231.

Wu, D and Pardridge, W M: "Central Nervous System Pharmacologic Effect in Conscious Rats after Intravenous Injection of a Biotinylated Vasoactive Intestinal Peptide Analog Coupled to a Blood-Brain Barrier Drug Delivery System" J. Pharmacol. Exp. Ther. 1996, 279, pp. 77-83.

Fukuta, M et al. "Insulin Fragments as a Carrier for Peptide Delivery Across the Blood-Brain Barrier" Pharmaceutical Res. 1994, vol. 11, pp. 1681-1688.

Prokai-Tatrai, K et al.: "Brain-Targeted Delivery of a Leucine-enkephalin Analogue by Retrometabolic Design" J. Med. Chem. 1996, 39, pp. 4775-4782.

Tamai, I et al: "Structure-Internalization Relationship for Adsorptive-Mediated Endocytosis of Basic Peptides at the Blood-Brain Barrier" J. Pharmacol. Exp. Ther. 1997, 280, pp. 410-415.

Chhajlani V. "Distribution of cDNA for melanocortin receptor subtypes in human tissues" Biochem. and Mol. Biol. Int. Feb. 1996;38(1):pp. 73-80.

Toth, I "A Novel Chemical Approach to Drug Delivery: Lipidic Amino Acid Conjugates" Journal of Drug Targeting, 1994, vol. 2, pp. 217 239.

Patel et al., "Peptide Targeting and Delivery across the Blood-Brain Barrier Utilizing Symthetic Triglyceride Esters: Design, Synthesis, and Bioactivity" Bioconjugate Chem 1997, 8, 434- 411.

Saito, Y et al.: "Vector-mediated delivery of 125 I-labeled β- amyloid peptide Aβ 1-40 through the blood-brain barrier And binding to Alzheimer disease amyloid of the Aβ 1-40/vector complex" Proc. Natl. Acad. Sci USA 1995, vol. 92, pp. 10227-10231.

Wu, D and Pardridge, W M: "Central Nervous System Pharmacologic Effect in Conscious Rats after Intravenous Injection of a Biotinylated Vasoactive Intestinal Peptide Analog Coupled to a Blood-Brain Barrier Drug System" J. Pharmacol. Exp. Ther. 1996, 279, pp. 77- 83

Fukuta, M et al. "Insulin Fragments as a Carrier for Peptide Delivery Across the Blood-Brain Barrier' Pharmaceutical Res. 1994, vol. 11, pp. 1681-1688.

Prokai-Tatrai, K et al.: "Brain-Targeted Delivery of a Leucine-enkephalin analogue by Retrometabolic Design" J. Med. Chem. 1996, 39, pp. 4775-4782.

Tamai, I et al: "Structure-Internalization Relationship for Adsorptive-Mediated Endocytosis of Basic Peptides at the Blood-Brain Barrier" J. Pharmacol. Exp. Ther. 1997, 280, pp. 410-415.

Chhajlani V. "Distribution of cDNA for melanocortin receptor subtypes in human tissues" Biochem. And Mol. Biol. Int. 1996 Feb;38(1):pp. 73-80.

Simpson, E R and Waterman M R, Regulation of the synthesis of steroidogenic enzymes in adrenal cortical cells by ACTH. (1988) Ann. Rev. Physiol. 50, 427-440.

Garrud, P, Gray J A & DeWied D: Pituitary-adrenal hormones and extinction of rewarded behavior in the rat. Physiol Psychol. 1974, 112, 109-119.

O'Donahue, T L, Handelmann G E, Loh Y P, Olton D S, Leibowitz J & Jacobowitz D M: Comparison of biological and behavioral activities of alpha- and gamma melanocyte stimulating hormones. Peptides 1981, 2, 101-104.

O'Donahue, T L, & Dorsa D M: the opiomelanotropinergic neuronal and endocrine systems. Peptides 1982, 3, 353-395.

Feng, J D, Dao T & Lipton J M: Effects of preoptic microinjections of MSH on fever and normal temperature control in rabbits. Brain Res. 1987, 18, 473-477.

De Wildt, D J, Kasbergen C M & Versteeg D H G: Effect of -melanocyte-stimulating hormone on cerebral blood flow in rats. J Cardiovascular Pharmacology 1995, 25, 898-905.

Friedman, J M: The alphabet of weight control. Nature 1997, 385, 119-120.

Chhajlani, V, Muceniece R and Wikberg J E S, 1993, Molecular cloning of a novel human melanocortin receptor, Biochem. Biophys. Res. Commun. 195, 866.

Chhajlani, V and Wikberg J E S, 1992, Molecular cloning and expression of the human melanocyte stimulating hormone receptor cDNA, Febs Lett. 309, 417.

Gantz, I, Konda Y, Tashiro T, Shimoto Y, Miwa H, Munzert G, Watson S J, DelValle J and Yamada T, 1993a, Molecular cloning of a novel melanocortin receptor, J. Biol. Chem. 268, 8246.

Gantz, I, Miwa H, Konda Y, Shimoto Y, Tashiro T, Watson S J, DelValle J and Yamada T, 1993b, Molecular cloning, expression, and gene localization of a fourth melanocortin receptor, J. Biol. Chem. 268, 15174.

Mountjoy, K G, Robbins L S, Mortrud M T and Cone R D, 1992, the cloning of a family of enes that encode the melanocortin receptors, Science 257, 1248.

Low, M J, Simerly R B, Cone R D, 1994, Receptors for the melanocortin peptides in the central nervous system, Curr. Opin. Endocr. Diab. 79.

Siegrist, W and Eberle A N, 1995, Melanocortins and their implications in melanoma, TEM, 6, 115.

Xia, Y, Wikberg J E S & Chhajlani V: Expression of melanocortin 1 receptor in periaqueductal gray matter. Neuroreport. 1995, 6, 2193-2196.

Vanetti, M, Schönrock C, Meyerhof W & Höllt V: Molecular cloning of a bovine MSH receptor which is highly expressed in the testis. FEBS Lett. 1994, 348, 268-272.

Rajora, N, Boccoli G, Burns D, Sharma S, Catania A P & Lipton J M: Alpha-MSG modulates local and circulating tumour necrosis factor-alpha in experimental brain inflammation. J. Neurosci. 1997a, 17, 2181-2186.

Thornvall, M, Dimitrou A, Xu X, Larsson E & Chhajlani V: Immunohistochemical detetion of the melanocortin 1 receptor in human testis, ovary and placenta using specific monoclonal antibody. Horm. Res. 1997, 48, 215-218.

Gantz, I, Shimoto Y, Konda Y, Miwa H, Dickinson C J & Yamada T: Molecular cloning, expression, and characterization of fifth melanocortin receptor. Biochem. Biophys. Res. Commun. 1994, 200, 1214-1220.

Griffon, N, Mignon V, Facchinetti P, Diaz J, Schwartz J-C & Sokoloff P: Molecular cloning and characterization of the fifth melanocortin receptor. Biochem. Biophys. Res. Commun. 1994, 200, 1007-1014.

Labbe et al. 1994: Labbé, 0, Desarnaud F, Eggerickx D, Vassart G & Parmentier M: Molecular cloning of a mouse melanocortin 5 receptor gene widely expressed in peripheral tissues. Biochemistry 1994, 33, 4543-4549.

Barrett, P, MacDonald A, Helliwell R, Davidsson G & Morgan P: Cloning and expression of a member of the melanocyte-stimulating hormone receptor family. J. Mol. Endocrinology. 1994, 12, 203-213.

Fathi, Z, lben L G & Parker E M: Cloning, expression, and tissue distribution of a fifth melanocortin receptor subtype. Neurochem Res. 1995, 20, 107-113.

Chhajlani, V, 1996, Distribution of cDNA for melanocortin receptor subtypes in human tissues, Biochem. Biophys. Res. Commun. 38, 73-80.

Schiöth, H B, Muceniece R, Wikberg J E S and Chhajlani V, 1995, Characterisation of melanocortin receptor subtypes by radioligand binding analysis, Eur. J. Pharmacol., Mol. Pharm. Sect. 288, 311.

Schiöth, H B, Kuusinen A, Muceniece R, Szardenings M, Keinänen K and Wikberg J E S, 1996a, Expression of functional melanocortin 1 receptors in insect cells, Biochem. Biophys. Res. Commun. 221, 807.

Schiöth, H B, Muceniece R and Wikberg J E S, 1996b, Characterisation of melanocortin 4 receptor by radioligand binding analysis. Pharmacol. & Toxicol. 79,161.

Schiöth, H B, Chhajlani V, Muceniece R, Klusa V and Wikberg J E S, 1996c, Major pharmacological distinction of the Acth receptor from the other melanocortic receptors, Life Sciences 59, 797.

Goninard, C, Goigoux C, Hollande L D & D'Hinterland L D: The administration of an alpha-MSH analogue reduces the serum release of Il-1 alpha and TNF alpha induced by the injection of a sublethal dose of lipopolysaccharides in the Balb/c mouse. Pigment Cell Res. 1996, 9, 148-153.

Tatro, J B and Reichlin S. 1987, Specific receptors for -melanocyte-stimulatingiormone are widely distributed in tissues of rodents, Endocrinology 121, 1900. Tatro & Entwistle 1994.

Sawyer, T K, San Filippo P. J, Hruby V J, Engel M H, Heward C B, Burnett J B & Hadley M E: 4-Norleucine, 7-D-phenylalanine-a-melanocyte-stimulating-hormone: a highly potent a-melanotropin with ultralong biological activity. Proc. Natl, Acad. Sci. USA 1980, 77, 5754-5758.

Chen, W, Shields T S, Stork P. J & Cone R D: A colorimetric assay for measuring activation of Gs- and Gq-coupled signaling pathways. Anal Biochem. 1995, 226, 349-54.

Chluba De Tapia, J, Bagutti C, Cotti R, Eberle a N: Induction of constitutive melanogenesis in amelanotic mouse melanoma cells by transfection of the human melanocortin 1 receptor gene. J. Cell Science 1996, 109, 2023 2030.

Desarnaud, F, Labbé O, Eggerickx D, Vassart G & Parmentier M: Molecular cloning, functional expression and pharmacological characterization of a mouse melanocortin receptor gene. Biochem J. 1994, 299, 367-373.

Zlokovic, B,V: "Cerebrovascular Permiability to peptides: Manipulations of Transport Systems at the Blood Brain Barrier" Pharmaceutical Res. 1995, 12: 1395 1406.

Fan, W, Boston B A, Kesterson R A, Hruby V J & Cone R D: Role of melanocortinergic neurons in feeding and the agouti obesity syndrome. Nature. 1997, 385, 165-168.

Feng, J D, Dao T & Lipton J M: Effects of preoptic microinjections of -Msh on fever and normal temperature control in rabbits. Brain Res. 1987, 18, 473-477.

Pardridge, W M "Recent Developments in Peptide Drug Delivery Into the Brain": Pharmacol. Toxicol. 1992, 71, 3-10.

Mountjoy, K G, Robbins L S, Mortrud M T and Cone R D, 1992, the cloning of a family of enes that encode the melanocortin receptors, Science 257, 1248.

Mountjoy, K G, Mortrud M T, Low M J, Simerly R B & Cone R D: Localization of the melanocortin-4 receptor (MC4-R) in endocrine and autonomic control circuits in the brain. Molecular Endocrinology 1994, 8, 1298-1308.

Mukherji, B & Chakraborty N. G: Immunobiology and immunotherapy of melanoma. Curr. Opin. Oncol. 1995, 7, 159-161.

Nordstedt, C, Fredholm B B.: A modification of a protein binding method for rapid quantification of cAMP in cell culture supernatants and body fluid. Anal. Biochem. 1990, 189, 231 234.

O'Hare, K B, Duncan R, Strohalm J, Ulbrich K & Kopeckova P: Polymeric drug-carriers containing doxorubicin and melanocyte-stimulating hormone: in vitro and in vivo evaluation against murine melanoma. J Drug Target 1993, 1, 217-229.

Riedle, S, Rosel M & Zoller M: In vivo activation and expansion of T cells by a bi-specific antibody abolishes metastasis formation of human melanoma cells in SCID mice. Int. J. Cancer 1998, 75, 908-918.

Roselli-Rehfuss, L, Mountjoy K G, Robbins L S, Mortrud M T, Low M J, Tatro J B, Entwistle M L, Simerly R B and Cone R D: Identification of a receptor for g melanotropin and other proopiomelanocortin peptides in the hypothalamus and limbic system. Proc. Natl. Acad. Sci. USA 1993, 90, 8856-8860.

Solca, F F, Chluba de Tapia J, Iwata K, Eberle a N: B16 G4F mouse melanoma cells: an MSH receptor deficient cell clone. Febs Lett. 1993, 322, 177 80.

Siegrist, W and Eberle A N, 1995, Melanocortins and their implications in melanoma, TEM, 6, 115.

Thörnvall, M, Dimitrou A, Xu X, Larsson E & Chhajlani V: Immunohistochernical detetion of the melanocortin 1 receptor in human testis, ovary and placenta using specific monoclonal antibody. Horm. Res. 1997, 48, 215-218.

Xia "Immunological localization of melanocortin 1 receptor on the cell surface of WM 266-4 human melanoma cells" Cancer Letter 98 (1996) 157-162.

Tatro, J and Entwistle M L, 1994, Heterogeneity of brain melanocortin receptors suggested by differential ligand binding in situ., Brain Research 635, 148.

MELANOCORTIN 1 RECEPTOR SELECTIVE COMPOUNDS

This is a continuation of Ser. No. 09/674,733 filed May 2, 2001 now U.S. Pat. No. 7,008,925, which is a 371 of PCT/GB99/01388 filed May 5, 1999.

The prior application(s) set forth above are hereby incorporated by reference in their entirety.

BACKGROUND OF THE INVENTION

1. Field of the Invention

The present invention relates to new compounds having high affinity and selectivity for the melanocortin 1 receptor (MC1-receptor). The new compounds selectively activate or block the MC1-receptors, which makes it possible to discriminate between the physiological effects mediated by the MC1-receptors and other subtypes of melanocortin receptors, and to afford selective pharmacological actions upon their administration to an animal or a human. The invention also relates to methods for their manufacture and their pharmaceutical preparations, as well as to their use for the treatment of medical and veterinary conditions which can be influenced by the MC1-receptor.

2. Related Art

Melanocortic peptides (melanocortins) are natural peptide hormones of animals, in particular mammals including man, which bind to and stimulate MC-receptors. Examples of melanocortins are α-MSH, β-MSH, γ-MSH, ACTH, and their peptide fragments. α-MSH is mainly known for its ability to regulate peripheral pigmentation (Eberle 1988), whereas ACTH is known to induce steroidoneogenesis (Simpson and Waterman 1988). The melanocortic peptides also mediate a number of other physiological conditions. Thus, they are reported to act as immunomodulators and to affect one or more of motivation, learning, memory, behaviour, inflammation, body temperature, pain, perception, blood pressure, heart rate, vascular tone, brain blood flow, nerve growth, placental development, aldosteron synthesis and release, thyroxin release, spermatogenesis, ovarian weight, prolactin and FSH secretion, uterine bleeding in women, sebum and pheromone secretion, blood glucose levels, weight homeostasis, intrauterine fetal growth as well as other events surrounding parturition (Garrud et al., 1974, Wiegant et al., 1979, O'Donahue et al., 1981, O'Donahue & Dorsa 1982, DeWied & Jolles 1982, Klein et al., 1985, Feng et al. 1987, Lin et al. 1987, Eberle, 1988, Gruber & Callahan 1989, DeWildt et al., 1995. Fruedman 1997).

By the use of molecular cloning, genes encoding five different subtypes of MC-receptors have been identified (Chhajlani et al. 1993, Chhajlani and Wikberg 1992, Gantz et al. 1993a, b, Mountjoy et al. 1992). The MC-receptors belong to the class of G-protein coupled receptors which are all built from a single peptide forming 7 transmembrane domains. The five MC-receptors are termed MC1, MC2, MC3, MG4 and MC5 and they all couple in a stimulatory fashion to cAMP. Of these the MC2-receptor is the ACTH-receptor whereas the others constitute subtypes of melanocyte stimulating hormone receptors (MSH-receptors).

The MC1-receptor is present on melanocytes and melanoma cells (Low et al. 1994, Siegrist & Eberle 1995). Recent data also indicate that the MC1-receptor is expressed in limited areas (periaqueductal gray) of rat and human brain (Xia et al. 1995), as well as in the testis (Vanetti et al. 1994). Also, very importantly recently the MC1-receptor is shown to be present on macrophages (Star et al. 1995), neutrophils (Catania et al. 1996), glioma cells and astrocytes (Wong et al. 1997), monocytes and endothelial cells (Hartmeyer et al. 1997, and references therein). Recently the MC1-receptor mRNA was also detected in the normal mouse brain (Rajora et al. 1997a), suggesting a specific function of this receptor in the brain. Moreover, recent data obtained by immunohistochemical detection techniques show that MC1-receptors are present in testis and ovary (Thömvall et al. 1997). This suggests a specific role of the MC1-receptor in reproductive physiology, as well as possibly in reproductive pathophysiology.

The MC2-receptor is the ACTH receptor. It is present in the cortex of the adrenal gland. The MC3-receptor mRNA is found in distinct areas of the brain, as well as in placental and gut tissues (Gantz et al. 1993a, Desarnaud et al. 1994, Roselli-Rehfuss et al. 1993). The MC4-receptor is ubiquitous in the brain (Gantz et al. 1993b, Mountjoy et al, 1994). The MC5-receptor is expressed in the brain, as well as in several peripheral tissues (Chhajlani et al. 1993, Gantz et al. 1994, Griffon et al. 1994, Labbé et al. 1994, Barrett et al. 1994, Fathi et al. 1995). More recent data indicate that all the 5 cloned MC-receptors have a wider tissue distribution (Chhajlani 1996).

The five MC-receptors show unique affinities for the melanocortic peptides (Schiöth et al. 1995, Schiöth et al. 1996a, b,c). Thus, the MC1-receptor shows high affinity for α-MSH, but lower affinities for β-MSH, γ-MSH and ACTH. The MC2-receptor binds ACTH with high affinity, but it does not bind the MSH peptides. The MC3-receptor show slightly higher affinity for γ-MSH compared to β- and α-MSH. The MC4-receptor shows slight preference for β-MSH, over α-MSH, and a very low affinity for γ-MSH. The MC5-receptor shows the same potency order for the MSH peptides as the MC1-receptor, although with much lower affinities (Schiöth et al. 1995, Schiöth et al. 1996a,b,c).

A diversity of effects is induced by natural melanocortic peptides not yet fully related to the various MC-receptor subtypes. These effects should be mediated by different subtypes of the MC-receptors. Most pertinent, however, is that increasing evidence indicates the MC1-receptors play an important role in the modulation of inflammation. Thus, for example, α-MSH was shown to inhibit formation of nitric oxide (NO) in cultured murine macrophages stimulated with bacterial lipopolysaccharide and γ-interferon, an effect claimed to be caused by the inhibition of the production of NO synthase (NOS) by the stimulation of MC1-receptors in macrophages (Star et al. 1995). As NO is believed to be a common mediator of all forms of inflammation this indicates that stimulation of MC1-receptors mediates the anti-inflammatory effect earlier known to be induced by MSH-peptides. α-MSH is also known to increase the formation of interleukin 10 (IL-10) in monocytes, which is believed to be an important component in immunosuppressive effects induced by α-MSH (Bhardwaj et al. 1996).

Recent studies also show that α-MSH potently inhibits the chemotactic migration of neutrophils (Catania et al. 1996). Moreover, neutrophils were shown to contain MC1-receptor mRNA, which was upregulated on stimulation of the neutrophils with interferon and bacterial lipopolysaccharide (Catania et al. 1996). Thus, as neutrophil migration constitutes an important component in early inflammation, these results again indicate the importance of the MC1-receptor as mediators of inhibition of inflammation.

In another study the injection of α-MSH, as well as the MSH-analogue [Nle$^4$,D-Phe$^7$]α-MSH (NDP-MSH) was shown to inhibit the release of cytokines IL-1 and TNF-α into the blood after intra-peritoneal injection of lipopolysaccharide (Goninard et al. 1996). This supports the anti-inflammatory role of MSH-peptides.

Important anti-inflammatory roles of MC-receptors (presumed to be of the MC1 type) have also been implicated in the brain since α-MSH inhibits the production of tumour necrosis factor alpha (TNF-α) in vivo, as well as in vitro on glioma cells; in the later case α-MSH was shown to inhibit formation of TNF-α induced by bacterial endotoxin (Wong et al. 1997).

In another study α-MSH given intracerebroventricularly or intraperitonally inhibited formation of central TNF-α induced by locally administered bacterial lipopolysaccharide (Rajora et al. 1997a). TNF-α occurs in neurological disorders, infection and injury of the brain, and is thought to underlie pathological processes in the brain. These data indicate an important role of MC-receptors as mediators of central anti-inflammatory actions.

Recently α-MSH was also shown to reduce inflammation in a model for inflammatory bowel disease (Rajora et al. 1997b).

The α-MSH peptide too is ascribed an important role in cutaneous biology. Most well known is its ability to stimulate pigment formation of the skin. α-MSH may act not only on MC-receptors located to melanocytes but also on immunocompetent and inflammatory cells, keratinocytes, fibroblasts and endothelial cells of the skin, thereby modifying keratinocyte proliferation and differentiation, and regulate endothelial cell and fibroblast cytokine production, as well as fibroblast collagenase production. α-MSH is known to downregulate the production of proinflammatory cytokines and accessory molecules on antigen presenting cells. In contrast suppressor factors such as IL-10 are upregulated by α-MSH (Luger 1997). In vivo data show that systemic application of α-MSH inhibits the induction and elicitation of contact hypersensitivity and induces hapten tolerance (Luger 1997). Thus, the accumulating evidence indicates that the stimulation of MC-receptors, presumably of the MC1-receptor subtype, mediates important negative regulation mechanisms of cutaneous inflammation and hyper-proliferative skin diseases (Luger 1997).

In addition to these findings, Hartmeyer et al. (1997) have shown that α-MSH increases MC1-receptor expression in dermal microvasculature endothelial cells and causes increased release of interleukin 8 (IL-8) from these cells. This indicates a role of MC1-receptors in the skin as modulators of inflammation and immunity (see Hartmeyer et al. 1997).

For further reading on the anti-inflammatory role of MSH peptides reference is made to the review by Lipton and Catania (1997).

Since 1957 MSH-receptors have been known as physiological entities. Binding sites for MSH/ACTH peptides have been identified in number of brain and peripheral tissues (Hnatowich et al. 1989, Tatro & Reichlin 1987, Lichtensteiger et al. 1993, Tatro & Entwistle 1994). Peptide structure activity studies of these receptors have been performed on melanophores from lower vertebrates like *Rana pipiens* (frog), *Anolis carolinensis* (lizard) and *Xenopus laevis*. Receptor studies were later also performed by binding on melanoma cell lines. These test systems gave comparable results and it is now known that the data obtained with these systems refer to the MC1-receptor (Eberle 1988).

Using such test systems it was found that replacement of L-Phe by D-Phe in α-MSH provided high potency and prolonged action (Sawyer et al., 1980). Cyclic $[Cys^4, Cys^{10}]$α-MSH analogues were also synthesized; they were found to be potent melanotrophs in skin pigmentation bioassays (Knittle et al., 1983, Sawyer et al., 1982). However, while some of the previous known natural and synthetic peptides, as well as more recently synthesized ones, show high affinity for MC1-receptors, their selectivity versus other subtypes of MC-receptors are limited (see e.g. Hol et al. 1994, Adan et al. 1994, among others). Recently, however, a peptide found by phage display screening was described which showed higher selectivity for MC1-receptors compared to other subtypes for MC receptors (Szardenings et al. 1997). However, for clinical and other uses this peptide showed inferior properties due to 1) comparatively low affinity for MC1-receptors, 2) low agonistic effects on MC1-receptors compared to other peptide hormones and 3) low stability due to presence of oxidizable SH groups and instability in regard of proteolytic cleavage.

There remains a need to provide means and methods to selectively regulate MC1-receptors. Thereby pharmacological effects affecting processes and conditions related to tissues and cells expressing the MC1-receptor may be elicited. These processes and conditions comprise but are not limited to immune responses, inflammatory processes, imunotolerance, immunomodulation, allergic processes, reproductive processes, melanoma and malignant diseases related to MC1-receptor expressing cells.

There is furthermore a need to provide chemical compounds that activate MC1-receptors selectively and with high potency; to provide chemical compounds which antagonize the action of other hormones and agonists on MC1-receptors selectively and with high potency; and to provide a method for administration of said compounds to animals including man.

DESCRIPTION OF THE INVENTION

According to the present invention are disclosed novel compounds showing high selectivity and high affinity for MC1-receptors in combination with effective stimulation of cAMP formation in MC1-receptor expressing cells. On the other hand the compounds of the invention show low or negligible affinity for other subtypes of MC-receptors.

According to the present invention are also disclosed novel compounds which inhibit the production of nitric oxide (NO).

According to the present invention are also disclosed novel compounds which are immunomodulatory and anti-inflammatory.

The compounds according to the present invention are represented by the general formula (1):

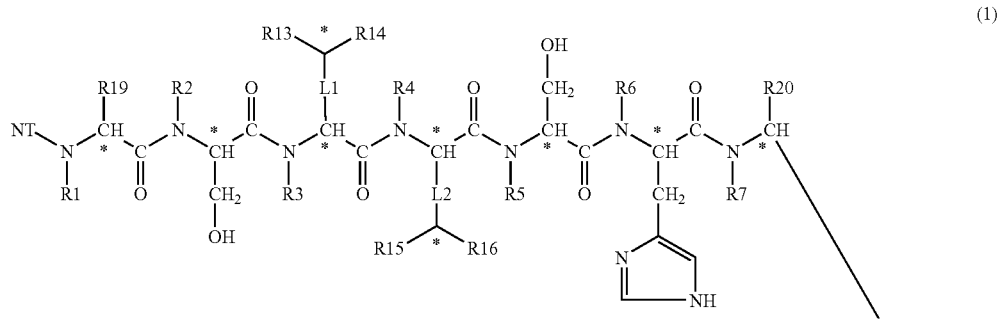

(1)

-continued

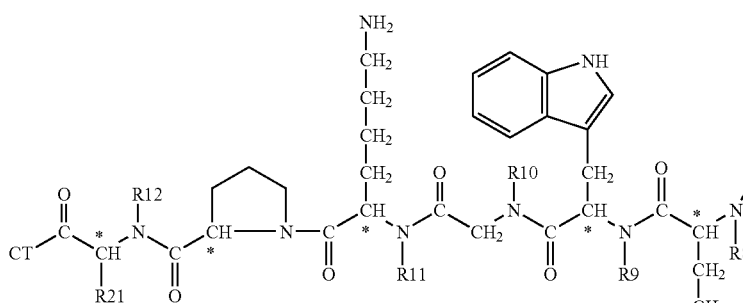
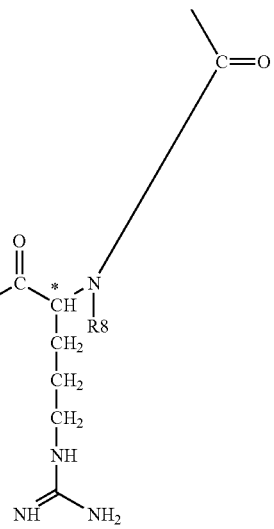

wherein R1, R2, R3, R4, R5, R6, R7, R8, R9, R10, R11 and R12 are selected independently from each other from H and methyl, with H being preferred, and wherein R13, R14, R15 and R16 are selected independently from each other from H and alkyl, in particular alkyl selected from methyl, ethyl, propyl, isopropyl, and wherein optionally one hydrogen in R13 and one hydrogen in R14 is exchanged for a bond between R13 and R14, and wherein optionally one hydrogen in R15 and one hydrogen in R16 is exchanged for a bond between R15 and R16, and wherein L1 and L2 are linkers which are independently selected from the group consisting of single bond, methyl, ethyl, with single bond being preferred, and wherein R19, R20 and R21 are selected independently from each other from H and —CH$_2$X, where X is H, alkyl, substituted alkyl, heteroalkyl, substituted heteroalkyl, alkenyl, substituted alkenyl, heteroalkenyl, substituted heteroalkenyl, alkynyl, substituted alkynyl, heteroalkynyl, substituted heteroalkynyl, cycloalkyl, substituted cycloalkyl, cycloheteroalkyl, substituted cycloheteroalkyl, cycloalkenyl, substituted cycloalkenyl, cycloheteroalkenyl, substituted cycloheteroalkenyl, aryl, substituted aryl, heteroaryl, substituted heteroaryl, functional group, and wherein NT is selected from H, hydroxyl, alkyl, aminoacid, aminoacid analogue, polypeptide and functional group, and CT is selected from hydrogen, hydroxyl, alkyl, aminoacid, aminoacid analogue, polypeptide and functional group, and wherein each asymmetric center (*) is in R or S configuration.

Preferably R20 is phenyl.

Recognizing that compounds according to formula (1) represent peptides, it is furthermore understood that the compounds of the invention are not limited to peptides according to formula (1), but include also compounds wherein one or several of the nitrogens of the peptide backbone have been exchanged for a carbon substituted with hydrogen, and/or wherein one or several of the oxygens of the carbonyl groups of the peptide backbone has been exchanged for two hydrogens.

The preferred stereomeric conformation of the compound (1) of the invention is disclosed in formula (2):

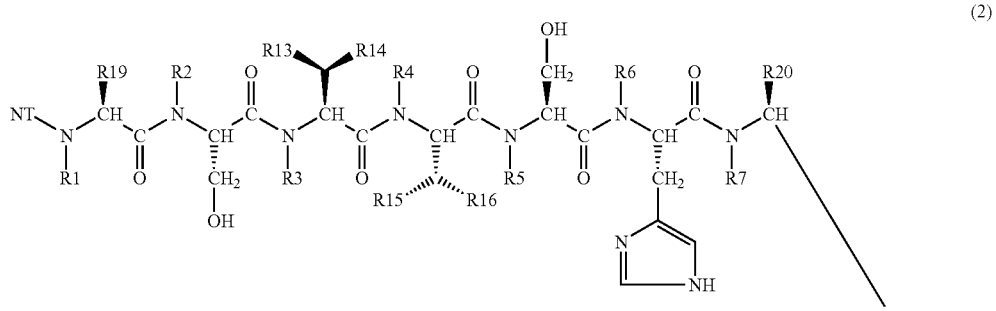

(2)

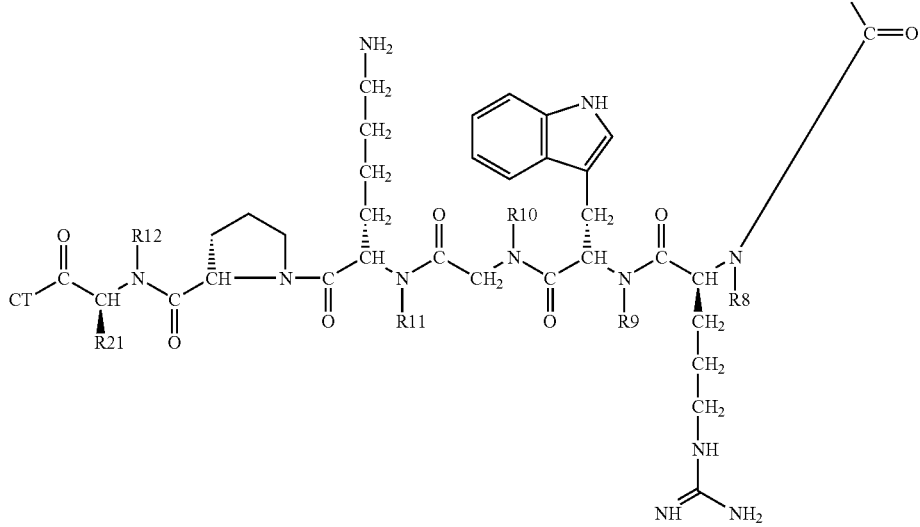

wherein R1, R2, R3, R4, R5, R6, R7, R8, R9, R10, R11 and R12 are selected independently from each other from H and methyl, with H being preferred, and wherein R13, R14, R15 and R16 are selected independently from each other from H and alkyl, in particular alkyl selected from methyl, ethyl, propyl, isopropyl, and wherein optionally one hydrogen in R13 and one hydrogen in R14 is exchanged for a bond between R13 and R14, and wherein optionally one hydrogen in R15 and one hydrogen in R16 is exchanged for a bond between R15 and R16, and wherein R19, R20 and R21 are selected independently from each other from H and —CH$_2$X, where X is H, alkyl, substituted alkyl, heteroalkyl, substituted heteroalkyl, alkenyl, substituted alkenyl, heteroalkenyl, substituted heteroalkenyl, alkynyl, substituted alkynyl, heteroalkynyl, substituted heteroalkynyl, cycloalkyl, substituted cycloalkyl, cycloheteroalkyl, substituted cycloheteroalkyl, cycloalkenyl, substituted cycloalkenyl, cycloheteroalkenyl, substituted cycloheteroalkenyl, aryl, substituted aryl, heteroaryl, substituted heteroaryl, functional group, and wherein NT is selected from H, hydroxyl, alkyl, aminoacid, aminoacid analogue, polypeptide and functional group, and CT is selected from hydrogen, hydroxyl, alkyl, aminoacid, aminoacid analogue, polypeptide and functional group.

For the compound according to formula (2) the preferred substituent of R20 is phenyl.

Recognizing that compounds according to formula (2) represent peptides, it is furthermore understood that the compounds of the invention are not limited to peptides according to formula (2), but include also compounds wherein one or several of the nitrogens of the peptide backbone has been exchanged for a carbon substituted by hydrogen, and/or wherein one or several of the oxygens connected to carbonyl groups of the peptide backbone has been exchanged for two hydrogens.

According to the invention is disclosed a particularly preferred compound (3), which in the following will be termed MS05 (SEQ ID NO:1):

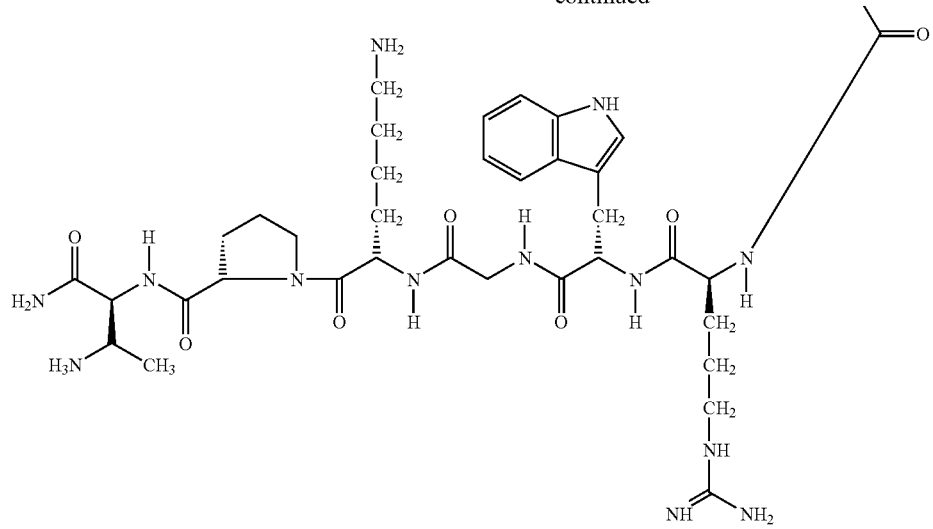
The invention also includes fragments of the compounds according to formula (1), (2) and (3), as detailed in the general formula (4) in which five moieties A, B, C, D, E have been delimitated:
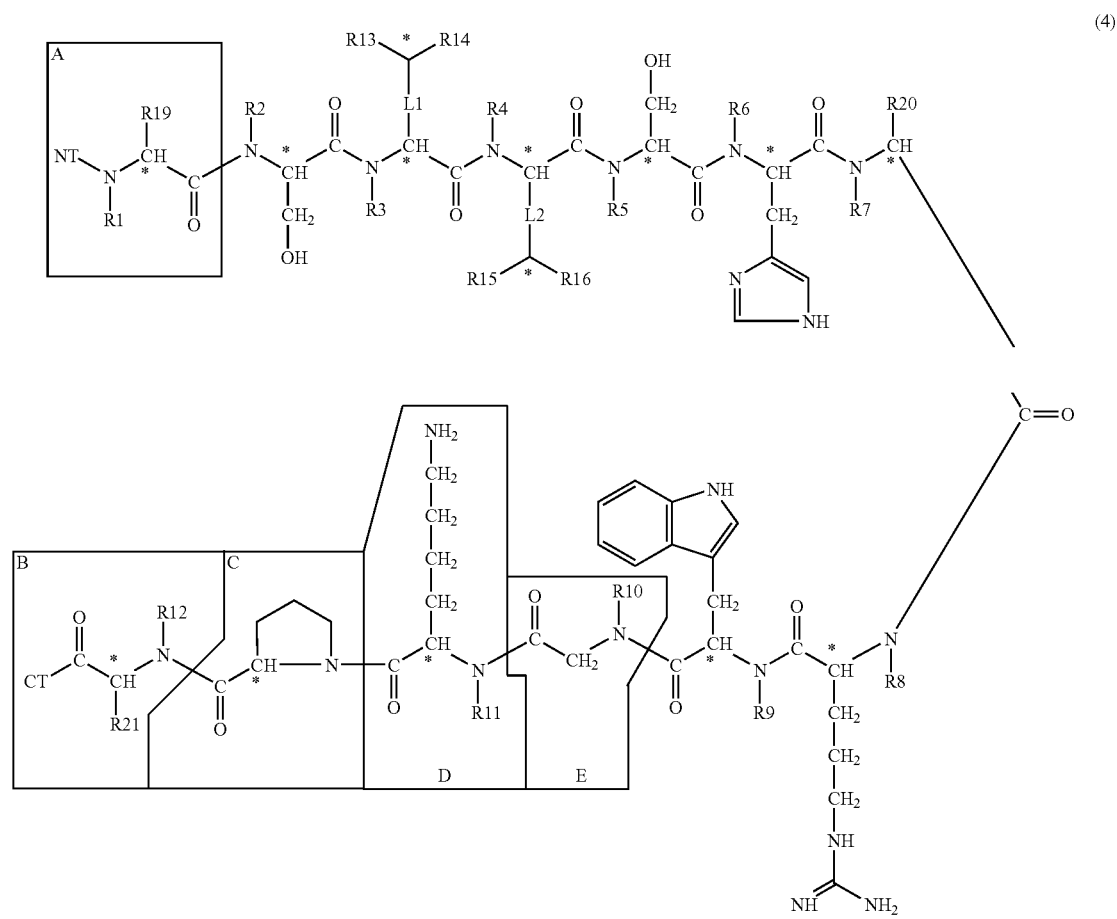
(4)

wherein R1, R2, R3, R4, R5, R6, R7, R8, R9, R10, R11 and R12 are selected independently from each other from H and methyl, with H being preferred, and wherein R13, R14, R15 and R16 are selected independently from each other from H and alkyl, in particular alkyl selected from methyl, ethyl, propyl, isopropyl, and wherein optionally one hydrogen in R13 and one hydrogen in R14 is exchanged for a bond between R13 and R14, and wherein optionally one hydrogen in R15 and one hydrogen in R16 is exchanged for a bond between R15 and R16, and wherein L1 and L2 are linkers which are independently selected from the group consisting of single bond, methyl, ethyl, with single bond being preferred, and wherein R19, R20 and R21 are selected independently from each other from H and —$CH_2X$, where X is H, alkyl, substituted alkyl, heteroalkyl, substituted heteroalkyl, alkenyl, substituted alkenyl, heteroalkenyl, substituted heteroalkenyl, alkynyl, substituted alkynyl, heteroalkynyl, substituted heteroalkynyl, cycloalkyl, substituted cycloalkyl, cycloheteroalkyl, substituted cycloheteroalkyl, cycloalkenyl, substituted cycloalkenyl, cycloheteroalkenyl, substituted cycloheteroalkenyl, aryl, substituted aryl, heteroaryl, substituted heteroaryl, functional group, and wherein NT is selected from H, hydroxyl, alkyl, aminoacid, aminoacid analogue, polypeptide or functional group, and CT is selected from hydrogen, hydroxyl, alkyl, aminoacid, aminoacid analogue, polypeptide, functional group, and wherein each asymmetric center (*) is in R or S configuration, and wherein moiety A is optionally exchanged for hydrogen, hydroxyl, alkyl, aminoacid, aminoacid analogue, polypeptide, or a functional group, and wherein moiety B is optionally exchanged for hydrogen, hydroxyl, alkyl, aminoacid, aminoacid analogue, polypeptide, or a functional group, and wherein optionally moiety C is exchanged for aminoacid or aminoacid analogue, and wherein optionally moiety D is exchanged for aminoacid or aminoacid analogue, and wherein optionally moiety E is exchanged for aminoacid or aminoacid analogue.

In a further advantageous embodiment of the invention according to formula (4) moiety C is exchanged for aminoacid or aminoacid analogue, whereas moieties D and E are retained.

In a further advantageous embodiments of the invention according to formula (4) moiety D is exchanged for aminoacid or aminoacid analogue, whereas moieties D and E are retained.

In a still further advantageous embodiment of the invention to formula (4), as defined above, moiety E is exchanged for aminoacid or aminoacid analogue, whereas the moieties C and D are retained.

In certain preferred embodiments of the invention one or several of R1, R2, R3, R4, R5, R6, R7, R8, R9, R10, R11 and R12 of the compounds according to formulae (1), (2) or (4) are selected to be methyl, whereas the rest is selected to be hydrogen, the selections being made so as to prevent or decelerate breakdown by proteases and/or peptidases. Moreover, the peptide backbone of the compounds according (1), (2) and (4) may be modified by exchanging , carbon, nitrogen and oxygen atoms by other atom(s), preferably oxygen, carbon and hydrogen, respectively, so as to prevent or decelerate breakdown by proteases and/or peptidases.

In even more advantageous embodiments of the invention less than 6, preferrably less than 5, more preferred less than 4 and preferably less than 2, and most preferred none of the R1, R2, R3, R4, R5, R6, R7, R8, R9, R10, R11 and R12 in compounds according to formula (1), (2) and (4) are selected to be methyl.

Moreover the peptide backbone of the compounds according to formula (1), (2) and (4) may be modified by exchanging carbon, nitrogen and oxygen atoms by other atom(s) so as to prevent or decelerate breakdown by proteases or peptidases, the preferred substitute for carbon being oxygen, for nitrogen being carbon, and for oxygen, hydrogen. In a preferred embodiment of this aspect of the invention preferably less than 5, more preferably less than 4, even more preferably less than 3, and most preferred less than 1 of said peptide backbone carbon, nitrogen and oxygen atoms are exchanged for oxygen, carbon or hydrogen.

In the present specification the term "peptide backbone" refers to the atoms marked by their bold characters in formulae (1), (2) and (4).

In addition R19, R20 and R21 may be selected so as to provide a modified compound the digestion of which by proteases or peptidases is delayed or prevented.

Included in the invention is a compound of formula (1), (2), (3) or (4) which has been subjected to minor structural alteration by the exchange of not more than five, preferably not more than four, more preferred not more than three, even more preferred not more than two and most preferred not more than one by methyl.

The invention comprises salts of the compound of the invention by known acids, including the trifluoroacetate, pharmaceutically acceptable salts being preferred.

In a preferred embodiment of the invention a rapid breakdown of the compound of the invention by endogenous enzymes is desired as this will provide a medicine short half life. It is however recognized that such a compound may act as a "hit-and-run" drug, the biological action of which extends beyond the period of time within which the presence of the compound of the invention can be detected in the respective animal; this effect due to a prolonged activation of the MC1-receptor.

It is also recognized that the structural variations of the compound of invention, as disclosed above, in particular the proper selection of substituents R19, R20, and R21, can be made so as to provide compounds with a capacity to either selectively activate or selectively block an MC1-receptor. Typical activation of MC1-receptor by a compound of the invention leads to stimulation of the generation of second messenger element cAMP, as shown in. Example 3, as well as biological responses and pharmacological effects related to the MC1-receptor. Activation of the MC1-receptor may also lead to receptor desensitization and/or receptor down regulation, something which in turn may lead to a decreased capacity of the MC1-receptor to generate biological responses and/or accumulation of cAMP. In some embodiments of the invention the capacity to afford MC1-receptor desensitization and/or MC1-receptor down regulation is a desired effect Moreover, in further embodiments of the invention upregulation and/or increased expression of the MC1-receptor can be afforded by the administration of the compound of the invention, which may also be a highly desirable effect.

On the other hand typical blockade by a compound of the invention of an MC1-receptor will prevent the induction of biological response by an endogenous or exogenous MSH peptide, a peptide analogue or a MC1-receptor stimulatory compound.

Compounds according to the invention typically showing capacity to activate MC1-receptors are represented by (but not limited to) compounds complying with formula (1), (2) or (4) in which R20 is aryl, substituted aryl, heteroaryl, substituted heteroaryl, phenyl or substituted phenyl. Compounds according to the invention typically showing capacity to block MC1-receptors are represented by (but not limited to) compounds complying with formula (1), (2) or (4) in which R20 is aryl, substituted aryl, heteroaryl, substituted heteroaryl, naphthalene, or substituted naphthalene.

Further embodiments of the invention are directed to compounds decreasing the formation of interleukin 1 (IL-1), interleukin 6 (IL-6): and tumour necrosis factor α (TNF-α), to afford decreased production of nitric oxide and downregulate the activity of nitric oxide synthase (NOS). Other embodiments of the invention are directed to compounds stimulating the production of interleukin 8 (IL-8) and/or interleukin 10 (IL-10). Yet other embodiments of the invention are directed to producing an effect opposite to that described in regard of IL-1, IL-6, TNF-α nitric oxide, NOS, IL-8 and IL-10.

The compounds of the invention may be manufactured by conventional chemical techniques known in the art. They are exemplified the synthesis of MS05 described in Example 1.1.

The compounds of the invention may also be manufactured by conventional molecular biological techniques known in the art. In this case the DNA-sequence encoding a peptide complying with formula (1), (2), (3) or (4) is typically manufactured first. The thus obtained DNA then is incorporated into an expression vector for use in a conventional expression system. Suitable expression systems are also known in the art and comprise eukaryotic or prokaryotic cells. Due to this possibility of manufacture of the compounds of the invention using molecular biological techniques, the present invention also includes DNA encoding a compound of the invention. The DNA encoding the compound of the invention may be joined at one or both of its 3' and 5'-ends to other DNA. The invention therefore includes DNA comprising a DNA sequence encoding the compound of the invention. The DNA encoding the compound of the invention may be present in a vector where it is joined with other DNA at one or both of its 3' and 5'-ends. The invention therefore includes a vector which comprises DNA encoding the compound of the invention.

The present invention also includes a fusion protein comprising one or several copies of the sequence of a compound of the invention. Such a fusion protein is typically manufactured by use of an expression system by utilizing the proper DNA, according to the principles described above, and by application of procedures well known in the art.

The invention also includes a vector comprising a DNA which encodes a fusion protein comprising the amino acid sequence of one or several copies of the compound of the invention. According to the present invention DNA can be exchanged for a chemically altered non-natural DNA, said non-natural DNA being capable of essentially affording the same function as natural DNA with respect to peptide or protein synthesis. Moreover, the DNA according to the invention can also be exchanged for RNA. It is particularly advantageous to use RNA or a non-natural RNA when the non-natural DNA or RNA is administered to an animal, in particular a human, the reason being avoidance of RNA or non-natural DNA recombining with endogenous DNA of the animal or human, thus diminishing the risk of long term side effects.

The term "alkyl" as employed herein by itself or as part of another group includes a straight or branched hydrocarbon chain of up to 18, preferably from 1 to 8 carbon atoms, such as methyl, ethyl, propyl, isopropyl, tert-butyl, butyl, pentyl, hexyl, heptyl or octyl.

The term "heteroalkyl" as employed herein by itself or as part of another group refers to alkyl wherein one or several carbon atoms are exchanged for heteroatom.

The term "alkenyl" as employed herein by itself or as part of another group includes a straight or branched hydrocarbon chain of up to 18, preferably from 2 to 8 carbon atoms comprising one or several carbon-carbon double bonds, such us propenyl, butenyl, pentenyl.

The term "heteroalkenyl" as employed herein by itself or as part of another group refers to alkenyl wherein one or several carbon atoms are exchanged for heteroatom.

The term "alkynyl" as employed herein by itself or as part of another group refers to alkyl or alkenyl containing one or several carbon-carbon triple bonds.

The term "heteroalkynyl" as employed herein by itself or as part of another group refers to heteroalkyl or heteroalkenyl containing one or several carbon-carbon triple bonds.

The term "cycloalkyl" as employed herein by itself or as part of another group refers to cyclic hydrocarbons containing from 3 to 12 carbons, preferably 3 to 8 carbons, such as cyclopropyl, cyclobutyl, cyclopentyl, cyclohexyl, cycloheptyl, cyclooctyl, which may optionally be fused with 1 or 2 cycles, each cycle being independently selected from the group consisting of cycloalkyl, cycloheteroalkyl, cycloalkenyl, cycloheteroalkenyl, aryl and/or heteroaryl.

The term "cycloheteroalkyl" as employed herein by itself or as part of another group refers to cycloalkyl where one or several carbon atoms are exchanged for heteroatom.

The term "cycloalkenyl" as employed herein by itself or as part of another group refers to cycloalkyl containing one or several carbon-carbon double bonds, such as cyclopentenyl and cyclohexenyl.

The term "cycloheteroalkenyl" as employed herein by itself or as part of another group refers to cycloheteroalkyl where one or more bonds between carbons, carbon and heteroatom, or heteroatoms are double.

The term "aryl" as employed herein by itself or as part of another group refers to phenyl which may optionally be fused with 1 or 2 cycles which are independently selected from cycloalkyl,-cycloheteroalkyl, cycloalkenyl, cycloheteroalkenyl, aryl, heteroaryl.

The term "heteroaryl" as employed herein by itself or as part of another group refers to a 5- to 12-membered aromatic ring, preferably 5- to 6-membered aromatic ring, which includes one or more heteroatoms, and which may optionally be fused with 1 or 2 cycles which are independently selected from cycloalkyl, cycloheteroalkyl, cycloalkenyl, cycloheteroalkenyl, aryl, heteroaryl.

The term "substituted" refers to one or more hydrogens being substituted, independently of each other, by alkyl, fluorinated alkyl, alkenyl, fluorinated alkenyl, alkynyl, fluorinated alkynyl, cycloalkyl, fluorinated cycloalkyl, cycloheteroalkyl, fluorinated cycloheteroalkyl, cycloalkenyl, fluorinated cycloalkenyl, cycloheteroalkenyl, fluorinated cycloheteroalkenyl, aryl, fluorinated aryl, heteroaryl, fluorinated heteroaryl, functional group. Moreover, if a structure connected with the term "substituted" is a cyclic structure fused with another cyclic structure or other cyclic structures, the latter cyclic structure(s) may also be substituted.

The term "halogen" as employed herein by itself or a part of another group refers to chlorine, bromine, fluorine and iodine, with chlorine being preferred.

The term "heteroatom" as employed herein by itself or as part of another group refers to nitrogen, oxygen or sulfur, to which one or more hydrogens may be connected according to its valence, and in which in the case of nitrogen one oxygen atom may be optionally connected to it by donor acceptor bond, thus forming N-oxide.

The term "functional group" as employed herein by itself or as part of another group refers to amino, alkylamino, dialkylamino, arylamino, arylazido, heteroarylamino, heteroarylazido, hydroxy, alkylhydroxy, fluorinated alkylhydroxy, cyano, carboxy, alkylcarboxy, arylcarboxy, halogen, nitro, hydroxylamino, acyl, fluorinated acyl, nitroso, sulfonyl, sulfinyl, thio, alkylthio, arylthio.

The term "fused" as employed herein by itself or as part of another group refers to two or three cycles having one or more common atoms, the preferred maximum number of fused cycles being three.

The term "aminoacid" as employed herein by itself or as part of another group refers to alanine, arginine, asparagine, aspartic acid, p-benzoyl-phenylalanine, β-cyclohexyl-alanine, cysteine, glutamic acid, glutamine, glycine, histidine, isoleucine, leucine, lysine, methionine, β-(2-naphtyl)-alanine, norleucine, phenylalanine, proline, serine, threonine, tryptophan, tyrosine, valine, 3,4-dichlorophenylalanine, 4-fluorophenylalanine, 4-nitrophenylalanine, 2-thienylalanine, 3-benzothienylalanine, 4-cyanophenylalanine, 4-iodophenylalanine, 4-bromophenylalanine, 4,4'-biphenylalanine, pentafluorophenylalanine, β, β-diphenylalanine, in either D- or L-conformations, D-L-1,2,3,4tetrahydroisoquinoline-3-carboxylic acid, as well as other substances having the following general structure (5):

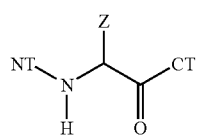

(5)

in which Z is H or —CH$_2$X, where X is H, alkyl, substituted alkyl, heteroalkyl, substituted heteroalkyl, alkenyl, substituted alkenyl, heteroalkenyl, substituted heteroalkenyl, alkynyl, substituted alkynyl, heteroalkynyl, substituted heteroalkynyl, cycloalkyl, substituted cycloalkyl, cycloheteroalkyl, substituted cycloheteroalkyl, cycloalkenyl, substituted cycloalkenyl, cycloheteroalkenyl, substituted cycloheteroalkenyl, aryl, substituted aryl, heteroaryl, substituted heteroaryl, or functional group, NT is H, functional group or bond to another aminoacid, and CT is functional group or bond to another aminoacid, the compound according to formula (5) being in either D- or L-conformation.

The term "aminoacid analogue" as employed herein by itself or as part of another group refers to a substance having the following general structure (6):

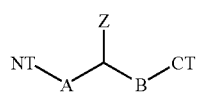

(6)

wherein A is oxygen, nitrogen or carbon to which hydrogen and/or methyl is attached according to valence, and wherein B is oxygen or carbon to which hydrogen and/or oxygen is attached according to valence, and wherein each asymmetric centre is in either R or S configuration, and wherein Z is H or —CH$_2$X, where X is H, alkyl, substituted alkyl, heteroalkyl, substituted heteroalkyl, alkenyl, substituted alkenyl, heteroalkenyl, substituted heteroalkenyl, alkynyl, substituted alkynyl, heteroalkynyl, substituted heteroalkynyl, cycloalkyl, substituted cycloalkyl, cycloheteroalkyl, substituted cycloheteroalkyl, cycloalkenyl, substituted cycloalkenyl, cycloheteroalkenyl, substituted cycloheteroalkenyl, aryl, substituted aryl, heteroaryl, substituted heteroaryl, or functional group, NT is H, functional group, bond to another aminoacid, or bond to another aminoacid analogue, and CT is functional group, bond to another aminoacid, or bond to another aminoacid analogue.

The compounds of the present invention have unique novel properties constituting their capacity to bind preferentially to the MC1-receptor among the five known subtypes of MC-receptors. This capacity is revealed in tests on recombinant human MC-receptors, using methods described in the literature (see Schiöth et al., Eur. J. Pharmacol., Mol. Pharm. Sect 1995, 288, 311 and Pharmacol. & Toxicol. 1996, 79, 161). In these tests the capacity of the compounds to compete for the binding of [$^{125}$I]-labelled NDP-MSH ([Nle$^4$, D-Phe$^7$]α-MSH) to recombinant human MC-receptor subtypes expressed in COS-1 cells was evaluated, as described in Example 2. With these assays the following dissociation constants (K$_i$s) were determined for some of the compounds of the invention:

| Compound | MC1 K$_i$ (nM) | MC3 K$_i$ (nM) | MC4 K$_i$ (nM) | MC5 K$_i$ (nM) |
|---|---|---|---|---|
| NDP-MSH | 0.11 | 0.39 | 2.3 | 2.9 |
| α-MSH | 0.68 | 52.3 | 2030 | 4990 |
| MS05 | 0.76 | 1365 | >>50000 | >>50000 |
| MS09 | 0.20 | 7.0 | 40 | 120 |

In the above table the K$_i$-values for non-labeled NDP-MSH and the natural α-MSH-peptide is given for comparison. It is evident from the Table that MS05, which is a particularly preferred compound of the invention, shows the same high affinity for the MC1-receptor as α-MSH, whereas it shows 1800-fold lower affinity for the MC3 receptor, and more than 65000-fold lower affinities for the MC4 and MC5 receptors, respectively. (In the above table >>50000 is intended to mean "larger than 50000" which means that MS05 did not show any appreciable capacity to bind to either the MC4- or MC5-receptor in concentrations up to 50000 nM). MS05 thereby shows very high selectivity for MC1-receptors when compared to its affinity for MC3, MC4 and MC5 receptors. Moreover, MS05 has very high affinity for the MC1-receptor. As is evident from the Table, MS09 is another preferred compound of the invention as it shows extremely high affinity for the MC-1 receptor. These properties are combined with an increased stability in comparison with compounds known in the art, something which seems to be due to the lack of easily oxidizable groups (e.g. —SH groups and —SH—CH$_3$ groups such as in cysteine and methionine). In addition MS05 and MS09 show a higher capacity to stimulate the generation of the second messenger cAMP compared to previously known compounds (see Example 3). The combination of the very high selectivity of MS05 and MS09 with their very high selectivity and good ability to stimulate formation of cAMP make MS05 and MS09 noteworthy. In Examples 3, 5 and 7 the high capacity of MS05 and MS09 to induce effective stimulation of cAMP is demonstrated.

Examples 4-7 show the capacity of the compounds of the invention to bind to native MSH-receptors (i.e. native MC1 receptors) in melanoma cells and macrophages, as well as to induce stimulation of cAMP in these cells. Example 8 demonstrates the capacity of the compounds of the invention to inhibit nitric oxide (NO) formation in macrophages where NO production had been stimulated by inflammatory agents (bacterial lipopolysaccharide and interferon gamma). The results show that the compounds of the invention are very effective inhibitors of NO which in a further sense demonstrates that the compounds of the invention are effective anti-inflammatory agents.

In the present specification by the term "high capacity to stimulate the second messenger cAMP" refers to the ability of 10 nM of a compound of the invention to induce at least 35%, preferably at least 45%, more preferred at least 55%, most preferred at least 65% stimulation of cAMP-formation in the MC1-receptor expressing cells described in Example 3, in comparison to that induced by 10 nM of α-MSH in the same system, using the method described in Example 3.

However, in the present specification a preferred method to determine whether or not a compound ("compound" is in this context also mutatis mutandis termed "test compound") shows a "high capacity to stimulate the second messenger cAMP" constitutes contacting a Specified_Concentration_A of the test compound to B16-F1 mouse melanoma cells (American Type Culture Collection) for a period of between 10 to 60 min, with a period of between 10-30 min being more preferred, and with a period of 20 min being most preferred, essentially using the procedures described in Example 5, and then determining the amount of cAMP formed in the cells. By a "high capacity to stimulate cAMP", according to this procedure, is defined a stimulation of cAMP amounting to at least 30%, more preferably amounting to at least 40%, somewhat more preferably amounting to at least 50%, even somewhat more preferably mounting to at least 60%, still even more preferably amounting to at least 70%, even still even more preferably amounting to at least 80%, and most preferably amounting to at least 90%, of that induced by contacting Specified_Concentration_A of α-MSH to B16-F1 mouse melanoma cells, using the same procedure as for the test compound. By "stimulation of cAMP" is in this context intended the increased level of cAMP induced over the basal level of cAMP, the basal level of cAMP being defined as the level of cAMP being present in the B16F1 cells which have been subjected to the identical procedures as when cells were contacted with test compound, except that no test compound or α-MSH is present during the period allocated for contacting. According to this procedure for determining the capacity of the test compound to stimulate cAMP by "Specified_Concentration_A" is intended a single concentration selected from within the range 1-100 nM, with 1 nM being preferred, 100 nM even more preferred and 10 nM most preferred.

By cAMP is in this context intended cyclic adenosine 3',5'-monophosphate (cyclic AMP).

As pointed out above the compounds of the invention are effective inhibitors of NO production. In the present specification a preferred method to determine whether or not a compound ("compound" is in this context also mutatis mutandis termed "test compound") is an "effective inhibitor of NO production" constitutes contacting Specified_Concentration_B of the test compound to mouse RAW 264.7 macrophage cells (American Type Culture Collection), the cells being concomitantly stimulated for their production of NO by the addition of between 0-300 ng/mL of bacterial lipopolysaccharide, with 50-150 ng/mL of bacterial lipopolysaccharide being more preferred, and with 100 ng/mL of bacterial lipopolysaccharide being most preferred, and the cells also being concomitantly stimulated for their production of NO by the addition of between 0-10 units/mL of mouse recombinant interferon gamma, with 3-7 units/mL of mouse recombinant interferon gamma being more preferred, and with 5 units/mL of mouse recombinant interferon gamma being most preferred, for a period of 1-22 hours, with 10-20 hrs being more preferred, and with 16 hours being most preferred, essentially using the procedures described in Example 8, and then determining the amount of nitric oxide (NO) formed, the NO being determined by using any method well known in the art, with the method described in Example 8, where the formation of NO is determined indirectly by measuring the amount of nitrite formed, being most preferred. By an effective inhibitor of NO production, according to this procedure, is defined an inhibition of NO production amounting to at least 30%, more preferably amounting to at least 40%, somewhat more preferably amounting to at least 50%, even somewhat more preferably amounting to at least 60%, still even more preferably amounting to at least 70%, even still even more preferably amounting to at least 80%, and most preferably amounting to at least 90%, of the inhibition of NO production afforded by contacting Specified_Concentration_B of α-MSH to the mouse RAW 264.7 macrophage cells, using the same procedure as for the test compound. By "inhibition of NO production" is in this context intended the reduction of NO production from the level of NO production obtained in RAW 264.7 cells which have been subjected to the identical procedures as when cells were contacted with test compound, except that no test compound or α-MSH is present during the period allocated for contacting. According to this procedure for determining the capacity of the test compound to inhibit NO production by "Specified_Concentration_B" is intended a single concentration selected from within the range 0.1-100 nM, with 0.1 nM being preferred, 100 nM somewhat more preferred, 1 nM even more preferred, and 10 nM most preferred.

In addition many of the compounds of the invention, in particular many of those complying with formula (1) and formula (2), including the compound according to formula (4), show increased stability against breakdown by peptidases while retaining their high selectivity and binding affinity for MC1-receptor. These properties are particularly valuable if prolonged half life in the body after systemic administration, is desired, and for causing sustained pharmacological actions in a living animal, in particular a human.

In addition, the compounds of the invention do not bind to MC2-receptors to an important extent which is of advantage. In the present specification, "MC1/MC3-selectivity" is defined as the ratio of the $K_i$ of a compound for an MC3-receptor ($K_i$-MC3) over the $K_i$ of the same compound for the MC1-receptor ($K_i$-MC1), the $K_i$ values being measured as described in Example 2, using the method described by Schiöth et al. 1995 and 1996b; hence:

$$MC1/MC3\text{-selectivity} = \frac{K_i\text{-}MC3}{K_i\text{-}MC1}$$

In the present specification, a "very high MC1/MC3-selectivity" of a compound of the invention refers to a MC1/MC3-selectivity of at least 60, preferably at least 100, more preferred of at least 200, even more preferred of at least 700, most preferred of at least 1000, even of at least 1200. However, in practically all of the embodiments of the present invention by a "very high MC1/MC3-selectivity" suffices an MC1/MC3-selectivity of at least 10, preferably at least 20, more preferably at least 30.

In the present specification "MC1/MC4-selectivity" of a compound is defined as the ratio of the $K_i$ of the compound for an MG4 receptor ($K_i$-MC4) over the $K_i$ of the same compound measured for the MC1-receptor ($K_i$-MC1), the $K_i$ values being measured as described in Example 2 by using the method described by Schiöth et al. 1995 and 1996b; hence:

$$MC1/MC4\text{-selectivity} = \frac{K_i\text{-}MC4}{K_i\text{-}MC1}$$

In the present specification a "very high MC1/MC4-selectivity" of a compound of the invention refers to a MC1/MC4 selectivity of at least 300, preferably of at least 1000, more preferred at least 3000, even more preferred of at least 10000, most preferred of more than 20000 and even more than 30000 and even 50000. However, in practically all of the embodiments of the present invention by a "very high MC1/MC4-selectivity" suffices an MC1/MC4-selectivity of at least 30, preferably at least 70, more preferably at least 150.

In the present specification "MC1/MC5-selectivity" of a compound is defined as the ratio of the $K_i$ of the compound for an MC5 receptor ($K_i$-MC5) over the $K_i$ of the same compound for the MC1-receptor ($K_i$-MC1), the $K_i$ values being measured as described in Example 2, using the method described by Schiöth et al. 1995 and 1996b; hence:

$$MC1/MC5\text{-selectivity} = \frac{K_i\text{-}MC5}{K_i\text{-}MC1}$$

In the present specification a "very high MC1/MC5-selectivity" of a compound of the invention refers to a MC1/MC5 selectivity of at least 300, preferably of more than 1000, more preferred of at least 3000, even more preferred of at least 10000, most preferred at least 20000 and even more than 30000 and 50000. However, in practically all of the embodiments of the present invention by a "very high MC1/MC5-selectivity" suffices an MC1/MC5-selectivity of at least 30, preferably at least 70, more preferably at least 150.

In the present context a "very high affinity" of a compound of the invention for an MC1-receptor indicates it exhibits a $K_i$ value of less than 30 nM, preferably of less than 15 nM, more preferred of less than 7 nM, even more preferred of less than 5 nM, most preferred of less than 3 nM, even less than 2 nM and less than 1 nM, the $K_i$ value for the MC1-receptor being measured as described in Example 2, by using the method described by Schiöth et al. 1995 and 1996b.

However, in the present context a "very high affinity" of a compound of the invention for an MC1-receptor is intended that it exhibits a $K_i$ value of less than 30 nM, preferably of less than 15 nM, more preferred of less than 7 nM, even more preferred of less than 5 nM, most preferred of less than 3 nM, even less than 2 nM and less than 1 nM, the $K_i$ value for the MC1-receptor being measured as described in Example 4 using mouse B16-F1 melanoma cells.

In the present context, whenever reference is made to the use of an MC1 receptor, or whenever reference is made to the human MC1 receptor, or to the MC1 receptor described by Chhajlani & Wikberg (FEBS Lett, 1992, 309, 417), or to the MC1 receptor used by Schiöth et al. Eur. J. Pharmacol. Mol. Pharm Sect, 1995, 288, 311-317 or Schioth, et al., Pharmacol. Toxicol. 1996, 79, 161-165, is intended the MC1 receptor which is encoded by the DNA which is available from Deutche Sammlung von Mikroorganismen und Zellkulturen (DSM), Braunschweig, Germany under the accession number DSM 7214, and which is described in the patent application no. PCT/DK93/00273 (WO94/04674).

However, in the present context, whenever reference to use of an MC1 receptor is made the receptor to be used can also be selected from a native MSH-receptor being present on melanoma cells of mammalian or human origin, without any matter of the present application being altered; the selection of the native MSH-receptor on B16-F1 melanoma cells being a preferred choice.

In the present context, whenever reference is made to an MSH-receptor is furthermore also intended a binding site which is capable of binding [$^{125}$I] NDP-MSH with a dissociation constant of 10 nM or lower, the dissociation constant being determined by using a radio-ligand binding procedure well known in the art, the preferred approach being described by Schioth et al. Eur. J. Pharmacol. Mol. Pharm Sect, 1995, 288, 311-317 or Schioth, et al. Pharmacol. Toxicol. 1996, 79, 161-165, with the extension that the MSH-receptor can be present in any natural or non-natural cell line of mammalian or human origin. Moreover, according to this definition of the MSH-receptor the [$^{125}$I] NDP-MSH binding can be largely prevented by the presence of between 0.1 µM to 10 µM of α-MSH during the assaying procedure.

In the present context, whenever reference is made to mouse RAW 264.7 macrophage cells, the RAW 264.7 macrophage cells can be exchanged with any other cells of mammalian or human origin that possesses MSH-receptors, and which NO production is inhibited by the addition of α-MSH, without any matter of the present context being altered.

Particularly preferred compounds according to the invention comprised by one or several of the structural formulas (1), (2), (3), (4), and for which one, preferably two, more preferred three, most preferred four of the properties selected from the group high MC1MC3-selectivity, high MC1/MC4-selectivity, high MC1/MC5-selectivity and high affinity for an MC1-receptor are combined. Moreover, an further preferred compound of the invention is one in which the said properties are combined with a high capacity to stimulate the second messenger cAMP.

By the term "high selectivity for MC1 receptors" is in the present context intended that a compound shows three, more preferably two, and most preferably one of the properties selected from the group of very high MC1/MC3-selectivity, very high MC1/MC4-selectivity, very high MC1/MC5-selectivity.

However, a very preferred compound according to the invention is comprised by one or several of the structural formulas (1), (2), (3), (4), which compound is also an effective inhibitor of NO production.

Marked positive treatment effects were found upon administration of MS05 to BALB/C mice. Animals were sensitized by injection of 2,4-dinitrofluorobenzene (DNFB). First 30 µL of 0.5% DNFB was administered to the shaved abdomen of the mice and after 4 days 10 µL of 0.3% DNFB was challenged to one paw, another paw being unchallenged and serving as a control. MS05 was administered, using a solution of MS05 in 0.9% saline, intraperitonally two hours before sensitization, and then the same dose was given intra-peritonally for four consecutive days, each dose of MS05 amounting to 0.05, 0.25, 0.37, 0.5 and 0.75 mg/kg. These treatments with MS05 were found to inhibit paw oedema by 3, 5, 12, 39 and 10%, respectively, compared to animals that were subjected to the same DNFB administration but which had not been given MS05. Moreover, in these tests the DNFB induced a marked increase in total blood white cell counts as well as marked increase in granulocyte counts of the blood, the increase in total white cell blood counts and granulocyte counts being essentially normalized by the MS05 treatment, the best effect being seen at 0.5 mg/kg of daily intraperitonally administrations of MS05. The DNFB administration also increased the count of lymphocytes/monocytes in the blood and this increase was essentially returned to normal levels upon the administration of MS05. Blood platelet counts was also increased in DNFB treated animals; the increase being returned towards the normal by administration of MS05. Similar reduction of the oedema induced by DNFB sensitization of the ears of BALB/c mice was seen upon intravenous injections of either MS05 or MS09, using solutions of MS05 and MS09 in 0.9% saline, to the animals. Thus, these results show that a compound of the invention prevents, ameliorates, and/or inhibits contact hypersensitivity, sensitization by a hapten, and/or has a positive treatment effect on oedema. Moreover these results show that the compound of the invention is capable of normalizing blood cell counts. Therefore the compound of the invention is in a further sense immunomodulatory. Moreover, these results demonstrate the capacity of a compound of the invention to be administrated in form of a pharmaceutical.

In further tests the MS05 or MS09 was administered to human microvascular endothelial cells (HMEC-1 cells; Department of Health & Human Services, Centres for Disease Control and Prevention, Atlanta, Ga. 30333, USA) in vitro. The HMEC-1 cells responded with an upregulated expression of mRNA for adhesion molecules ICAM-1, VCAM and E-Selectin, as well as by upregulation of the ICAM-1, VCAM and E-Selectin proteins, upon administration of TNF $\alpha$(10 ng/mL). The administration of MS05 or MS09 (preferred concentrations of MS05 and MS09 being within 0.01 nM to 10 μM, and preferred times for contacting the cells with MS05 or MS09 being 3-48 hours) led to inhibition of the upregulated expression of mRNA for adhesion molecules ICAM-1, VCAM and E-Selectin, as well as to inhibition of the upregulation of the ICAM-1, VCAM and E-Selectin proteins. These results demonstrate the capacity of the compound of the invention to be immunomodulatory, to be useful for the treatment of inflammation related to the vasculature, e.g. having positive treatment effects in vasculitis. In this context by ICAM-1 is intended intercellular adhesion molecule type 1, by VCAM is intended vascular adhesion molecule, and by E-Selectin is intended endothelial selectin (Sluiter et al, J. Cardiovasc. Pharmacol. 1993, 22 Suppl 4: S37-44, Elangbam et al., Vet. Pathol. 1997 Jan. 34(1): 61-73).

The compounds of the invention can be used for the treatment and diagnosis of diseases and disorders and/or pathological conditions, including preventive treatment, in an animal, in particular a mammal, but they are most preferably used for these purposes in man. Moreover, the compounds of the invention can be used also in healthy individuals and in healthy animals to change their physiological state.

In such treatment or diagnosis the compound of the invention is administered in form of a pharmaceutical composition further comprising a pharmaceutical acceptable carrier and, optionally, tabletting agents, wetting agents, binders and fillers, preservatives, such as antioxidants and anti-microbial agents, buffers and salts. Preferred carriers comprise injection media, particularly water. The compositions are administered by any conventional route including the oral, enteral, rectal and parenteral routes. Parenteral routes comprise intravenous, intramuscular, subcutaneous and peritoneal injection. The compounds of the invention may also be administered by inhalation, as nasal spray, and topically on the skin. They may also be administered epidurally, intrathecally and intracerebroventricularly.

In particular the pharmaceutical composition containing a pharmacologically effective amount of a compound of the invention is administered to an animal, in particular man, for alteration of physiological state, diagnosis, prevention or therapeutic treatment of diseases, in particular conditions which are positively affected by the simulation of MC1-receptors or alternatively positively affected by blockade, and/or by downregulation, and/or by desensitization of MC1-receptors. Examples of such conditions include inflammation of any type and any origin. In particular is therewith intended inflammation or any related condition as well as any condition involving the action of macrophages, neutrophils, monocytes, keratinocytes, fibroblasts, melanocytes, pigment cells and endothelial cells. Moreover included are conditions caused by or associated with increased production and/or release of inflammatory cytokines such as interleukins, in particular interleukin 1 (IL-1), interleukin 6 (IL-6), and tumor necrosis factor $\alpha$ (TNF-$\alpha$). Thus the compounds of the invention are useful for immunomodulatory treatment in man, mammals and animals. Included are also conditions associated with increased production of nitric oxide (NO) as well as upregulated activity of nitric oxide synthase (NOS). Moreover, the compounds of the invention are useful for treating conditions related to the testis and ovary.

In the present specification "increased production" refers to increased formation, increased release, or increased content of an endogenous compound locally, regionally or systemically in a patient compared to the content of said endogenous compound in a healthy individual. In the present specification "upregulated" refers to an increased activity or content of the compound compared with that in a healthy individual.

In the present specification "decreased production" is refers to decreased formation, decreased release, or decreased content of an endogenous compound in a patient compared to the content of said endogenous compound in a healthy individual. In the present specification "downregulated" refers to a decreased activity or content of the compound compared with that in healthy individual.

In particular, positive treatment effects or preventive effects are seen in conditions where inflammation or inflammatory like condition is caused by or being associated with one or more of the following: allergy, hypersensitivity, bacterial infection, viral infection, inflammation caused by toxic agent, fever, autoimmune disease, radiation damage by any source including UV-radiation, X-ray radiation, $\gamma$-radiation, $\alpha$- or $\beta$-particles, sun burns, elevated temperature, mechanical injury. Moreover, inflammation due to hypoxia, which is optionally followed by reoxygenation of the hypoxic area, is typically followed by severe inflammation, which condition is positively affected by treatment with a compound of the invention.

In very specific embodiments of the invention a compound of the invention is administered for prevention or therapeutic treatment of inflammatory diseases of the skin (including the dermis and epidermis) of any origin, including skin diseases having a inflammatory component Specific examples of this embodiment of the invention include treatment of contact dermatitis of the skin, sunburns of the skin, burns of any cause, and inflammation of the skin caused by chemical agent psoriasis, vasculitis, pyoderma gangrenosum, discoid lupus erythematosus, eczema, pustulosis palmo-plantaris, and phemphigus vulgaris.

Also comprised by the invention is the administration of the compound of the invention for treatment of an inflammatory disease in the abdomen, including an abdominal disease having a inflammatory component Specific examples of treatment of such disease with a compound of the invention are gastritis, including one of unknown origin, gastritis perniciosa (atrophic gastritis), ulcerous colitis (colitis ulcerosa), morbus Crohn, systemic sclerosis, ulcus duodeni, coeliac disease, oesophagitis and ulcus ventriculi.

Comprised by the invention is also administration of the compound of the invention for treatment of systemic or general and/or local immunological diseases, including those of an autoimmune nature, and other inflammatory diseases of a general nature. Specific examples include treatment of rheumatoid arthritis, psoriatic arthritis, systemic sclerosis, polymyalgia rheumabca, Wegener's granulomatosis, sarcoidosis, eosinophilic fasceitis, reactive arthritis, BechtereW's disease, systemic lupus erythematosus, arteritis temporalis, Behcet's disease, morbus Burger, Good Pastures' syndrome, eosinophilic granuloma, fibromyalgia, myositis, and mixed connective tissue disease. Included therein is also arthritis, including arthritis of unknown origin.

Further included in the invention is administration of the compound of the invention for treatment of a disease of the peripheral and central nervous system related to inflammation. Included in this aspect of the invention is the treatment of cerebral vasculitis, multiple sclerosis, autoimmune ophtalmitis, polyneuropathia. Comprised by the invention is also the administration of a compound of the invention for treatment of an inflammation of the central nervous system to prevent apoptotic cell death. Moreover, as the compounds of the invention show a distinct ability to induce nerve regeneration, positive treatment effects are often seen in central nervous system diseases involving damage of cells in this region. This aspect of the invention also includes treatment of traumatic injuries to the central nervous system, brain edema, multiple sclerosis, Alzheimer's disease, bacterial and viral infections in the central nervous system, stroke, and haemorrhagia in the central nervous system.

Comprised by the invention is also the administration of the compound of the invention for treatment of diseases of the eye and tear glands related to inflammation. Specific examples of such diseases comprise anterior and posterior uveitis, retinal vasculitis, otpicus neuritis, Wegener's granulomatosis, Sjögren's syndrome, episcleritis, scleritis, sarcoidosis affecting the eye and polychondritis affecting the eye.

Comprised by the invention is also the administration of the compound of the invention for treatment of diseases of the ear related to inflammation, specific examples of which include polychondritis affecting the ear and external otitis.

Comprised by the invention is also the administration of the compound of the invention for treatment of diseases of the nose related to inflammation, specific examples of which are sarcoidosis, polychondritis and mid-line granuloma of the nose.

Comprised by the invention is also the administration of the compound of the invention for treatment of diseases related to inflammation of the mouth, pharynx and salivary glands. Specific examples include Wegener's granulomatosis, mid-line granuloma, Sjögren's syndrome and polychondritis in these areas.

Included in the invention is also the administration of the compound of the invention for treatment of diseases related to inflammation in the lung. Specific examples include treatment of idiopathic alveolitis, primary pulmonary hypertension, bronchitis, chronic bronchitis, sarcoidosis, alveolitis in inflammatory systemic disease, pulmonary hypertension in inflammatory systemic disease, Wegener's granulomatosis and Good Pastures' syndrome.

Comprised by the invention is also the administration of the compound of the invention for treatment of diseases related to the inflammation of the heart. Specific examples include treatment of pericarditis, idiopathic pericarditis, myocarditis, Takayasus' arteritis, Kawasaki's disease, coronary artery vasculitis, pericarditis in inflammatory systemic disease, myocarditis in inflammatory systemic disease, endocarditis and endocarditis in inflammatory systemic disease.

Comprised by the invention is also the administration of the compound of the invention for treatment of diseases related to inflammation of the liver. Specific examples include treatment of hepatitis, chronic active hepatitis, biliary cirrhosis, hepatic damage by toxic agent, interferon induced hepatitis, hepatitis induced by viral infection, liver damage induced by anoxia, liver damage caused by mechanical trauma.

Comprised by the invention is also the administration of the compound of the invention for treatment of diseases related to inflammation of the pancreas. Specific examples include treatment (and prevention) of diabetes mellitus, acute pancreatitis, chronic pancreatitis.

Comprised by the invention is also the administration of the compound of the invention for treatment of diseases related to the inflammation of the thyroidea. Specific examples of these embodiments of the invention include treatment of thyreoiditis, autoimmune thyreoiditis and Hashimoto's thyreoiditis.

Comprised by the invention is also the administration of the compound of the invention for treatment of diseases related to inflammation of the kidney. Specific examples include treatment of glomerulonephritis, glomerulonephritis in systemic lupus erythematosus, periarteritis nodosa, Wegener's granulomatosis, Good-Pastures' syndrome, HLAb27 associated diseases, IgA nephritis (IgA=Immunoglobuline A), pyelonephritis, chronic pyelonephritis and interstitial nephritis.

Comprised by the invention is also the administration of the compound of the invention for treatment of diseases related to the inflammation of the joints. Specific examples include treatment of Bechterew's disease, psoriatic arthritis, rheumatoid arthritis, arthritis in colitis ulcerosa, arthritis in morbus Crohn, affection of joints in systemic lupus erythematosus, systemic sclerosis, mixed connective tissue disease, reactive arthritis, Reiter's syndrome. Moreover, included in this embodiment of the invention is treatment of arthrosis of any joint, in particular arthrosis of finger joints, the knee and the hip.

Comprised by the invention is also the administration of the compound of the invention for treatment of diseases related to the inflammation of blood vessels. Specific examples include treatment of arteritis temporalis, periarteritis nodosa, arteriosclerosis, Takayasus' arteritis and Kawasaki's disease. In particular advantageous is the capacity of a compound of the invention to afford protection against and prevention of arteriosclerosis. This is in part due to the capacity of the compound of the invention to prevent the induction of inducible nitric oxide synthase (iNOS) caused by the action of oxidized Low Density Lipoprotein on endothelial cells and blood vessel walls.

Comprised by the invention is also the administration of a compound of the invention for treatment of drug induced disorders of the blood and lymphoid system, including the treatment of drug induced hypersensitivity (including drug hypersensitivity) affecting blood cells and blood cell forming organs (e.g. bone marrow and lymphoid tissue). Specific embodiments of this aspect of the invention include the treatment of anemia, granulocytopenia, trombocytopenia, leukopenia, aplastic anemia, autoimmune hemolytic anemia, autoimmune thrombocytopenia and autoimmune granulocytopenia.

The compounds of the invention can also be administered for treatment of fast allergic disorders (Type I allergy). Included in this embodiment of the invention is the treatment of anaphylactic reactions, anaphylactoid reactions, asthma, asthma of allergic type, asthma of unknown origin, rhinitis, hay fever and pollen allergy.

Comprised by the invention is also the administration of the compound of the invention for the treatment of inflammation related to infections of any origin. Specific examples include treatment of inflammation secondary to infection caused by virus, bacteria, helminths and protozoae.

Comprised by the invention is also the administration of the compound of the invention for treatment of inflammations related to trauma and tissue injury of any origin.

Because of the capacity of the compounds of the invention to stimulate pigment formation in epidermal cells the compounds of the invention are also useful for inducing skin tanning for cosmetic reasons, for treatment of vitiligo, or any other condition where darkening of skin color is desired. Moreover, because of the ability of the compounds of the invention to inhibit pigment formation in cells of the skin they are also useful for inducing lighter skin color for cosmetic reasons, or during any condition where a lighter color of skin is desired.

The compounds of the invention are also useful for inducing formation of the second messenger element cAMP. In particular, such formation of cyclic adenosine 3',5'-monophosphate (cAMP) is desired for eliciting the specific pharmacological effects of the compounds of the invention when administered to a living organism, in particular a human. However, the induction of cAMP formation may also be of great value in cells or crushed cell systems in vitro, e.g. for analytical or diagnostic purposes. A specific embodiment of this aspect of the invention is given in Example 3.

The compounds of the invention are also useful for inhibiting the in vivo formation of the second messenger element cAMP. Such inhibition may also be used in cells or crushed cell systems in vitro, e.g. for analytical or diagnostic purposes.

The compounds of the invention are administered in pharmacologically effective amounts which may vary from 0.001 mg/day/kg body weight to 1000 mg/day/kg body weight depending on the nature of the compound, the desired treatment effect and route of administration; however, lower amounts may be effective, if delivered locally. The compounds of the invention have low toxicity and are well tolerated.

For analytical and diagnostic purposes the compounds of the invention can be used in radioactive form, including radioactive labels. In particular they may be manufactured so as to incorporate radioactive iodine or tritium, or any other suitable radionuclide. Such a radioactively labeled compound can be used in radio-ligand binding for the quantification of MC1-receptors, for the analysis of dissociation constant ($K_i$s or $K_d$s) of drugs competing with specific subtypes of melanocortin receptors, and for the localization of MC1-receptors in tissues and tissue sections e.g. by use of receptor autoradiographic techniques. Principles of radio-ligand binding and receptor autoradiography are well known in the art.

Alternatively the compounds of the invention can be labeled with any other type of label that allows detection of the respective compound, e.g. a fluorescent label, biotin, an enzyme, and the resulting compound be used for the same purpose as the corresponding radioactively labeled compound. The compound of the invention may also be labeled with other labels that are activated by secondary processes like irradiation with γ-radiation, light photons or by biochemical processes, the purpose being to cause changes in a target cell or tissue wherein the labeled compound of the invention is located. Such changes may be useful to affect the viability and fate the cells or tissues in an organism to which the compound is administered.

The compounds of the invention can also be provided with group that can be activated by light, in particular UV-light, the purpose being to obtain a compound useful for covalent labeling of MC1-receptors by use of the photoaffinity labeling technique. Photoaffinity labeling is a technique well known in the art which in the present context is useful for elucidating the structure and topological organisation of the MC1-receptor. Such photoactive derivatives of the compounds of the invention are also part of the present invention. Photoactive derivatives of the compounds of the invention may also be made to incorporate and easily detectable group or label, such as e.g. a radioactive atom, a fluorescent group or biotin. (For further details in regard of photoaffinity labeling see Leeb-Lundberg et al. J. Biol. Hem. 1984, 259, 2579 and Scimonelli & Eberle FEBS Lett 1978, 226, 134).

The compounds of the invention can also be labeled with gamma or positron emitting isotopes. A thus labeled compound may be administered systematically or locally to an animal, including a human. By virtue of the ability of the radioactive compound of the invention to bind selectively to MC1-receptors imaging of the in vivo binding of specific MC-receptor subtypes may be obtained by using techniques well known in the art such as scintigraphy, positron emission tomography (PET) or single photon emission computed tomography (SPECT). By using such methods information on the distribution and/or numbers of MC1-receptors in tissues of an animal or a human subject can be obtained. This information is of value for diagnosis of disease, in particular for diagnosis of malignant melanoma, as melanoma cells are known to be rich in MC1-receptors. Moreover, the very same technique may be used for the treatment of any other malignancy where the malignant cells contain MC1-receptors. Examples of the latter are cancer with originating from the ovaries or testes. For general examples of this technique, which is directly applicable for the compound of the invention, see Bagutt et al. 1994.

Moreover, the compound of the invention can also be tagged with a toxic agent and used for targeted delivery of the toxin to malignant melanoma cells or other cells bearing MC1-receptors (e.g. malignant cells with origin from the ovary or testis). In this context 'tagged' is intended to mean that the compound of the invention is covalently or non-covalently bound to a toxin, for instance ricin, doxorubicin and diphtheria toxin. By virtue of the high affinity and selectivity of the compound of the invention for the MC1-receptor specific delivery of the toxin to MC1-receptor bearing cells (e.g. melanoma cells) is achieved and malignant cell growth is selectively inhibited, even including killing of the malignant cells. The principles used for this approach are well known in the art (Murphy et al. 1986, Tatro et al. 1992, O'Hare et al. 1993). The compounds of the invention may also be tagged with a compound capable of activating the endogenous immune system. A thus formed hybrid of a compound of the invention and a immune system activating compound can be used for treatment of malignant melanoma or any other MC1-receptor expressing disease condition. The portion of the hybrid molecule containing the compound of the invention will, at the one hand, bind to the MC1-receptor of malignant melanoma cells (including both the primary tumor and metastases), as well as other MC1-receptor bearing malignant tumor cells, while, at the other hand, the immune system activating component will trigger an immune response directed against the tumor cells. This turn leads to inhibition of tumor cell growth and eventual tumor cell death. Typical example of such a "bispecific" hybrid compound is a hybrid between the compound of the invention [i.e. the compound according to formula (1), (2), (3) or (4)] and a compound capable of binding to a T-cell antigen. Typically the T-cell antigen binding compound of the hybrid compound is an antibody directed against T-cell antigen CD3. The antibody in this case is preferably a monoclonal antibody. The so formed hybrid compound will direct cytotoxic cells to the malignant melanoma cells or the MC1-receptor bearing malignant cells and inhibit the tumor growth. The compound of the invention may be attached to the antibody chemically by covalent or non-covalent bond(s). The hybrid compound may also be manufactured by genetic engineering by incorporating the DNA sequence encoding a peptide corresponding to the compound of the invention with other DNA encoding a suitable protein. The peptide sequence of the compound of the invention may thus become incorporated into a longer peptide sequence constituting, for instance, an antibody, a hybrid antibody, a hybrid molecule containing part of an antibody, or an antibody like protein. It is furthermore recognized that the hybrid compound may contain one or several copies of the compound of the invention. When several copies of the MC1-receptor binding moieties are incorporated into the hybrid compound of the invention the thus formed hybrid will show increased affinity to the MC1-receptor. This is an advantage in the treatment of MC1-receptor related malignant disease. In line with what was described above the present invention therefore includes a hybrid compound incorporating one or several copies of the compound of the invention with another molecule. For the general principles underlying immunotherapy using the approach described above reference see Riedle et al. 1998, Mukherji et al. 1995, Canevari et al. 1995 and Thielemans 1995. These approaches and methods can be adopted for targeting MC1-receptor expressing malignant conditions, by use of the approach outlined above.

The compounds of the invention may be used for the treatment and diagnosis of diseases, disorders and/or pathological conditions in an animal, in particular in man.

The compounds of the invention may be delivered to the preferred site in the body by a suitable drug delivery system. For example a compound of the invention may be coupled to a carrier molecule to make it lipophilic (see e.g. Toth, I: Drug Targeting, 1994, 2, 217-239; Patel et al., Bioconjugate Chem 1997, 8, 434411). Other techniques useful for delivering the compound of the invention to the desired site in the body are vector mediated carrier systems (see e.g. Pardridge, W M: Pharmacol Toxicol 1992, 71, 3-10; Saito, Y et al.: Proc. Natl. Acad. Sci USA 1995, 92, 10227-10231; Wu, D and Pardridge, W M: J. Pharmacol. Exp. Ther. 1996, 279, 77-83). Yet other examples of drug delivery technologies useful for the compounds of the invention include the conjugation of the compound of the invention with an active molecule capable of being transported through a biological barrier (see e.g. Zlokovic, B V: Pharmaceutical Research 1995, 12, 1395-1406). A specific example constitutes the coupling of the compound of the invention to fragments of insulin in order to achieve transport across the blood brain barrier (Fukuta, M et al. Pharmaceutical Res. 1994, 11, 1681-1688). Other examples which are principally useful for and adaptable to the compounds of the present invention are to be found in Prokai-Tatrai, K et al.: J. Med. Chem. 1996, 39, 4775-4782 and Tamai, I et al: J. Pharmacol. Exp. Ther. 1997, 280, 410-415. For general reviews of technologies for drug delivery suitable for the compounds of the invention see Zlokovic, B V: Pharmaceutical Res. 1995, 12; 13951406 and Pardrige, W M: Pharmacol. Toxicol. 1992, 71, 3-10.

The present invention also relates to a pro-drug which, upon administration to an animal or a human, is converted to a compound of the invention. A pro-drug of the compound of the invention can be used for the same purposes as described in this patent for the compounds of the invention, as well as is disclosed in the Examples given below.

The compound of the invention can be administered together with peptidase and/or protease inhibitors to prevent or delay the breakdown of the compound of the invention and thereby prolong its duration of pharmacological action in the body as well as its stability in the gastrointestinal tract when administered perorally. Peptidase/protease inhibitors that may be administered together with a compound of the invention are preferably selected from the group of angiotensin converting enzyme inhibitors (ACE-inhibitors) such as e.g. captopril (D-3-mercaptomethyl-propionyl-L-proline), enaplapril, phosphoramidone, amastatin.

The compounds of the present invention can be bound covalently or non-covalently to one or several of other molecule(s) of any desired structure(s); the thus formed modified compound or complex can be used for the same purposes as described in this patent for the compounds of the invention, as well as is disclosed in the Examples given below. In a particularly important embodiment of the invention a radioactively labeled molecule is covalently bound to the compound of the invention so as to make the compound of the invention radioactively labeled.

In the following the invention will be described in greater detail by reference to a number of preferred embodiments which however are only given for purposes of illustration and must not be considered to limit the invention in any way.

ABBREVIATIONS

Figure 1:
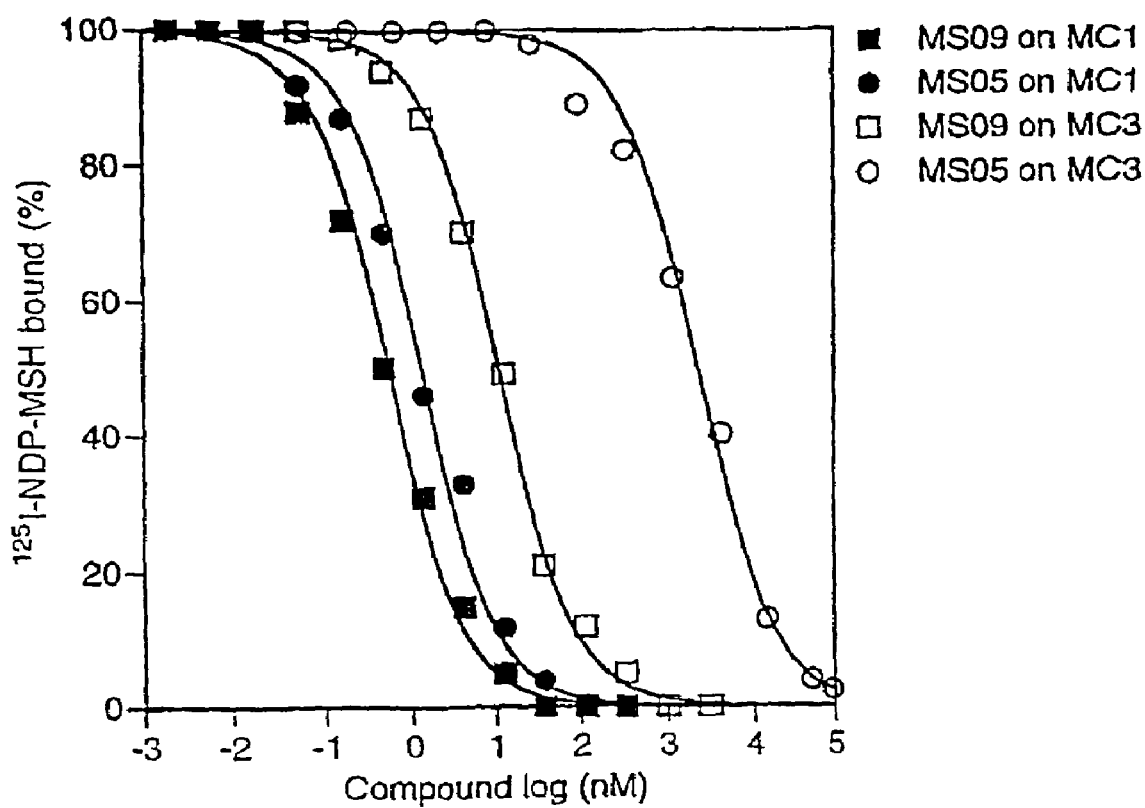
FIG. 1: Competion curves for MS05 and MS09 on MC1 and MC3 receptors.

Abbreviations used in the following examples:
Fmoc=9-fluorenylmethoxycarbonyl
DMF=N,N-Dimethylformamide
Fmoc-Val-OPfp=9-Fluorenylmethoxycarbonyl-L-valine pentafluoro phenyl ester
HOAt=1-Hydroxy-7-azabenzotriazole
Fmoc-Pro-OPfp=9-Fluorenylmethoxycarbonyl-L-proline pentafluorophenyl ester
Fmoc-Lys(Boc)-OPfp =α-s-Fluorenylmethoxycarbonyl-E-tert-butyloxycarbonyl-L-lysine pentafluorophenyl ester Fmoc-Gly-OPfp=9-Fluorenylmethoxycarbonyl-glycine pentafluorophenyl ester
Fmoc-Trp(Boc)-OH=9-Fluorenylmethoxycarbonyl-($N^{in}$-tert-butyloxycarbonyl)-L-tryptophan
HATU=O-(7-Azabenzotriazol-1-yl)-1,1,3,3-tetramethyluronium hexafluorophosphate
DIEA=N,N-diisopropylethylamine
Fmoc-Arg(Pbf)-OH=9-Fluorenylmethoxycarbonyl-($N^g$-2,2,4,6,7-pentamethyldihydrobenzofuran-5-sulfonyl)-L-arginine
Fmoc-Phe-OPfp=9-Fluorenylmethoxycarbonyl-L-phenylalanine pentafluorophenyl ester
Fmoc-His(Trt)-OH=9Fluorenylmethoxycarbonyl-$N^{im}$-trityl-L-histidine
Fmoc-Ser(But)-OH=9-Fluorenylmethoxycarbonyl-O-tert-butyl-L-serine
Fmoc-Ile-OPfp=9-Fluorenylmethoxycarbonyl-L-isoleucine pentafluorophenyl ester
Ac=acetyl
dPhe=D-phenylalanine
dSer=D-serine
NMeSer=N-methyl-L-serine
NMeVal=N-methyl-L-valine
NMedPhe=N-methyl-D-phenylalanine
PyAOP=Q-(7-azabenzotriazol-1-yl)-tris(pyrrolidino)-phosphonium hexafluorophosphate
TFFH=tetramethylfluoroformamidinium hexafluorophosphate
NDP-MSH=[$Nle^4$,$D-Phe^7$] α-MSH

EXAMPLE 1:1

Synthesis of L-seryl-L-seryl-L-Isoleucyl-L-isoleucyl-L-seryl-L-histidyl-L-phenylalanyl-L-arginyl-L-tryptophanyl-glycyl-L-lysyl-L-prolyl-L-valinamide (MS05) (SEQ ID NO:1)

The MS05 peptide (Ser-Ser-Ile-Ile-Ser-His-Phe-Arg-Trp-Gly-Lys-Pro-Val-$NH_2$) (SEQ ID NO:1) was assembled on a solid support using the Pioneer peptide synthesis system from PerSeptive Biosystems UK.

The starting cycle was as follows: 100 mg (0.02 mmole) of [5-(4-Fmoc-aminomethyl-3,5-dimethoxy) valeric acid attached to polyethylene-graft polystyrene support (Fmoc-PAL-PEG-PS, capacity 0.2 mmole/g) was placed into a peptide synthesis column. The Fmoc group was then removed by 5 min treatment with 20% piperidine in DMF, followed by a wash of the support with DMF.

After completion of the starting cycle the resin was subjected to repeated aminoacid coupling cycles, each cycle consisting of 30-90 min circulation of appropriate reagents (as detailed below) dissolved in 4 ml DMF through the column, followed by washing with DMF, 5 min treatment with 0.3 M acetic anhydride in DMF, washing with DMF, 5 min treatment with 20% piperidine in DMF, and then again washing with DMF before the start of the next cycle. Thirteen cycles were applied using reagents and treatment times as follows (in order): 1) Fmoc-Val-OPfp (40 mg, 0.08 mmol) and HOAt (11 mg, 0.08 mmol) (90 min), 2) Fmoc-Pro-OPfp (40 mg, 0.08 mmol) and HOAt (11 mg, 0.08 mmol)(60 min), 3) Fmoc-Lys(Boc)-OPfp (51 mg, 0.08 mmol) and HOAt (11 mg, 0.08 mmol) (30 min), 4) Fmoc-Gly-OPfp (37 mg, 0.08 mmol) and HOAt (11 mg, 0.08 mmol)( 30 min), 5) Fmoc-Trp (Boc)-OH (42 mg, 0.08 mmol), HATU (30 mg, 0.08 mmol) and DIEA (0.068 ml, 0.4 mmol) (30 min), 6) Fmoc-Arg(Pbf)-OH (52 mg, 0.08 mmol), HATU (30 mg, 0.08 mmol) and DIEA (0.068 ml, 0.4 mmol) (90 min), 7) Fmoc-Phe-OPfp (44 mg, 0.08 mmol) and HOAt (11 mg, 0.08 mmol)( 60 min), 8) Fmoc-His(Trt)-OH (50 mg, 0.08 mmol), HATU (30.0 mg, 0.08 mmol) and DIEA(0.068 ml, 0.4 mmol) (30 min), 9) Fmoc-Ser(tBu)-OH (31 mg, 0.08 mmol), HATU (30.0 mg, 0.08 mmol) and DIEA (0.068 ml, 0.4 mmol) (30 min), 10) Fmoc-Ile-OPfp (42 mg, 0.08 mmol) and HOAt (11 mg, 0.08 mmol) (90 min), 11) Fmoc-Ile-OPfp (42 mg, 0.08 mmol) and HOAt (11 mg, 0.08 mmol) (90 min), 12) Fmoc-Ser(tBu)-OH (31 mg, 0.08 mmol), HATU (30.0 mg, 0.08 mmol) and DIEA (0.068 ml, 0.4 mmol) (60 min), 13) Fmoc-Ser(tBu)-OH (31 mg, 0.08 mmol), HATU (30.0 mg, 0.08 mmol) and DIEA (0.068 ml, 0.4 mmol) (30 min).

After the last cycle the support was washed with DMF, followed by a methanol and methylene chloride wash, and dried in vacuo. The dried resin was treated with 2.5 ml of deprotection mixture (trifluoroacetic acid-phenol-anisole-1,2-ethanedithiol-water, 82:2:2:2:2) for 3 hours at room temperature. It was filtered, washed on the filter with trifluoroacetic acid, the filtrates combined and concentrated in vacuo at room temperature. Dry ether was added and the precipitate formed was filtered off and washed on the filter with ether, then dried in vacuo over KOH. Yield 31 mg. HPLC data (2×250 mm column, Vydac RP C18, 90A, 201HS1010): k'(main substance)=3.50 (19% acetonitrile in water+0.1% trifluoroacetic acid, detection at 220 nm). The raw product was dissolved in 1 ml of 60% MeCN in water and the solution divided into three portions and placed into centrifuge tubes, each of them then being diluted with 0.1% aqueous trifluoroacetic acid to 1.5 ml volume. It was centrifuged and the clear solutions were used for semipreparative HPLC (10×250 mm column, Vydac RP C18, 90A, 201HS1010, eluate −19% acetonitrile in water+0.1% trifluoroacetic acid, detection at 220 nm. Fractions containing the main peak were pooled and lyophilized. A white powder was formed. Yield of trifluoroacetate salt of MS-05 was 13.2 mg (33%). Rf 0.28(1-butanol-pyridine-acetic acid-water, 4:1:1:2). Mass spectrometry data: m/e=1514.3.

EXAMPLE 1:2

Synthesis of Ser-Ser-Ile-Ile-Ser-His-dPhe-Arg-Trp-Gly-Lys-Pro-Val-$NH_2$ (MS-09) (SEQ ID NO:2) tetrafluoroacetate was made essentially as described in Example 1.

Yield 36%. $R_f$ 0.56. k' 2.0 (21% MeCN in 0.1% TFA). m/e 1512.9.

EXAMPLE 1:3

Synthesis of Tyr-Ser-Ser-Ile-Ile-Ser-His-Phe-Arg-Trp-Gly-Lys-Pro-Val-$NH_2$ (MS30) (SEQ ID NO:3) tetratrifluoroacetate was made essentially as described in Example 1.

Yield 33%. $R_f$ 0.79. k' 4.4 (8.4% MeCN in 0.1% TFA). m/e 1675.9.

EXAMPLE 1:4

Synthesis of Tyr-Ser-Ile-Ile-Ser-His-Phe-Arg-Gly-Lys-Pro-Val-$NH_2$ (MS-31) (SEQ ID NO:4) tetratrifluoroacetate was made essentially as described in Example 1.

Yield 34%. $R_f$ 0.75. k' 2.7 (10.8% MeCN in 0.1% TFA). m/e 1589.1.

EXAMPLE 1:5

Synthesis of Ser-Ser-Ile-lle-Ser-His-Phe-Arg-Trp-Gly-Lys-Pro-Val-Tyr-$NH_2$ (MS-32) (SEQ ID NO:5) tetratrifluoroacetate was made essentially as described in Example 1.

Yield 28%. R$_f$ 0.75. k' 3.3 (9.6% MeCN in 0.1% TFA). m/e 1675.9.

EXAMPLE 1:6

Synthesis of Ser-Ile-Ile-Ser-His-Phe-Arg-Trp-Gly-Lys-Pro-Val-NH$_2$ (MS-33) (SEQ ID NO:6) tetratrifluoroacetate was made essentially as described in Example 1.

Yield. 26%. R$_f$ 0.73. k' 3.6 (8.4% MeCN in 0.1% TFA). m/e 1425.7.

EXAMPLE 1:7

Synthesis of Thr-Ser-Ile-Ile-Ser-His-Phe-Arg-Trp-Gly-Lys-Pro-Val-NH$_2$ (MS-34) (SEQ ID NO:7) tetratrifluoroacetate was made essentially as described in Example 1.

Yield 52%. R$_f$ 0.72. k' 2.4 (10.8% MeCN in 0.1% TFA). m/e 1527.1.

EXAMPLE 1:8

Synthesis of Ser-Thr-Ile-Ile-Ser-His-Phe-Arg-Trp-Gly-Lys-Pro-Val-NH$_2$ (MS-35) (SEQ ID NO:8) tetratrifluoroacetate was made essentially as described in Example 1.

Yield 49%. R$_f$ 0.68. k' 2.2 (10.8% MeCN in 0.1% TFA). m/e 1526.8.

EXAMPLE 1:9

Synthesis of Ser-Ser-Val-Ile-Ser-His-Phe-Arg-Trp-Gly-Lys-Pro-Val-NH$_2$ (MS-36) (SEQ ID NO:9) tetratrifluoroacetate was made essentially as described in Example 1.

Yield 42%. R$_f$ 0.68. k' 2.3 (10.8% MeCN in 0.1% TFA). m/e 1499.3:

EXAMPLE 1:10

Synthesis of Ser-Ser-Ile-Val-Ser-His-Phe-Arg-Trp-Gly-Lys-Pro-Val-NH$_2$ (MS-37) (SEQ ID NO:10) tetratrifluoroacetate was made essentially as described in Example 1.

Yield 69%. R$_f$ 0.65. k' 3.3 (12.0% MeCN in 0.1% TFA). m/e 1499.0.

EXAMPLE 1:11

Synthesis of Ac-Ser-Ser-Ile-Ile-Ser-His-Phe-Arg-Trp-Gly-Lys-Pro-Val-NH$_2$ (MS-38) (SEQ ID NO:11) tetratrifluoroacetate was made essentially as described in Example 1.

Yield 49%. R$_f$ 0.72. k' 1.8 (10.8% MeCN in 0.1% TFA). m/e 1554.7.

EXAMPLE 1:12

Synthesis of dSer-Ser-Ile-Ile-Ser-His-Phe-Arg-Trp-Gly-Lys-Pro-Val-NH$_2$ (MS-39) (SEQ ID NO:12) tetratrifluoroacetate was made essentially as described in Example 1.

Yield 44%. R$_f$ 0.69. k' 2.2 (12% MeCN in 0.1% TFA). m/e 1512.4.

EXAMPLE 1:13

Synthesis of NMeSer-Ser-Ile-Ile-Ser-His-Phe-Arg-Trp-Gly-Lys-Pro-Val-NH$_2$ (MS-40) (SEQ ID NO:13) tetratrifluoroacetate was made essentially as described in Example 1. Fmoc-NMeSer(Bu$^t$)-OH was added using PyAOP.

Yield 47%. R$_f$ 0.67. k' 1.7 (12% MeCN in 0.1% TFA). m/e 1526.6.

EXAMPLE 1:14

Synthesis of Ser-Ser-Ile-Ile-Ser-His-Phe-Arg-Trp-Gly-Lys-Pro-NMeVal-NH$_2$ (MS-41) (SEQ ID NO:14) tetratrifluoroacetate was made essentially as described in Example 1. Fmoc-NMeVal-OH was added using TFFH.

Yield 2.5%. R$_f$ 0.68. k' 4.4 (22.8% MeCN in 0.1% TFA). m/e 1527.3.

EXAMPLE 1:15

Synthesis of Ser-Ser-Ile-Ile-Ser-His-NMedPhe-Arg-Trp-Gly-Lys-Pro-Val-NH$_2$ (MS-42) (SEQ ID NO:15) tetratrifluoroacetate was made essentially as described in Example 1. Fmoc-NMedPhe-OH was added using PyAOP.

Yield 40%. R$_f$ 0.70. k' 2.5 (10.8% MeCN in 0.1% TFA). m/e 1527.0.

EXAMPLE 2

Assay of Binding Affinities of Compounds of the Invention for Human MC-receptors Expression of receptor clones. Human MC1- and MC5-receptor DNAs (Chhajlani and Wikberg 1992; Chhajlani et al., 1993), cloned into the expression vector pRc/CMV (In-Vitrogen Corp., USA), and human MC3- and human MC4-receptor DNAs (Gantz et al., 1993a & b), cloned into the expression vector pCMV/neo, were used. COS cells were grown and transfected with receptor clones as described (Schiöbth et al. 1995, 1996b). After transfection cells were cultivated for 48 h, detached from the Petri dishes, and used for radioligand binding as described (Schiöth et al. 1995, 1996b).

Binding studies. The transfected cells were washed with binding buffer (Minimum Essential Medium with Earle's salts, 25 mM HEPES, pH 7.0, 0.2% bovine serum albumin and distributed into 96 well plates. The cells were then incubated for 2 h at 37° C., with 0.1 ml binding buffer in each well containing [$^{125}$I][Nle$^4$, D-Phe$^7$]α-MSH and appropriate concentrations of the peptide to be tested. After incubation the plates were put on ice and the cells were washed with 0.1 ml of ice-cold binding buffer. The cells were then detached from the plates with 0.2 ml of 0.1 N NaOH. Radioactivity was counted by using a Wallac, Wizard automatic gamma counter. The competition data were analyzed by fitting it to the logistic function using non-linear regression analysis. The K$_i$-values were then calculated from the thus obtained IC50-values by using the Cheng and Prusoff equation, essentially as described by Schiöth et al. 1995, 1996b.

Results

K$_i$ values for NDP-MSH, α-MSH, MS05 and MS09 for MC1, MC3, MC4 and MC5 receptors are shown in the Table below:

| Compound | MC1 K$_i$ (nM) | MC3 K$_i$ (nM) | MC4 K$_i$ (nM) | MC5 K$_i$ (nM) |
|---|---|---|---|---|
| NDP-MSH | 0.11 | 0.39 | 2.3 | 2.9 |
| α-MSH | 0.68 | 52.3 | 2030 | 4990 |
| MS05 | 0.76 | 1365 | >>50000 | >>50000 |
| MS09 | 0.20 | 7.0 | 40 | 120 |

FIG. 1 shows competition curves for MS05 and MS09 on MC1 and MC3 receptors.

EXAMPLE 3

Assays of the Effect of the Compounds of the Invention on Generation of the Second Messenger cAMP in Cells Expressing MC1-receptors Preparation of Stable Cell Lines Human MC1-receptors had been cloned earlier into pZeoSV (Invitrogen) (Szardenings et al., 1997). The resulting vectors were used for transformation of the amelanotic mouse melanoma cell line B16G4F that lacks the mouse MC1-receptors (Solca et al., 1993) using liposomes (Campbell, 1995) as described previously (Schiöth et al., 1997b). Cells were cultivated in Dulbecco's modified Eagle's medium with 10% fetal calf serum at 7% $CO_2$ for 24 hours and seeded on large plates in the same medium containing 300 µg/ml Zeocin. The medium was exchanged every 4-5 days until cell foci appeared. Single foci were isolated and grown under antibiotic selection. Expression and binding characteristics of these receptors were determined and found to be identical with the same receptors expressed in other cell lines, as has already also been shown earlier for the human MC1-receptor (Chluba-de-Tapia et al. 1996).

Stimulation of Cell cAMP

For cAMP measurements the cells were detached from 60-80% confluent adherent cultures using Hank's balanced salts containing 0.5 mM EDTA and incubated for 30-60 min at 37° C. in ordinary growth medium containing 0.5 mM of the phosphodiesterase inhibitor 3-isobutyl-1-methyl-xanthine (IBMX). 20 µl aliquots of appropriate dilutions of test compounds in growth medium were prepared in 96 well microtitre plates and placed in a water bath at 37° C. For the stimulation about $1.5 \times 10^5$ cells in 180 µl were quickly added to each well to obtain immediate mixing. After 20 min 20 µl of 4.4 M perchloric acid were added, mixed, neutralized after a few minutes by addition of 20 µl base (5 M KOH, 1 M Tris) and centrifuged.

Determination of cAMP Concentrations

20 µl of acid treated supernatant obtained above were mixed with 50 µl buffer (100 mM Tris-Cl, 250 mM NaCl, 10 mM EDTA, 0.1% mercaptoethanol, 0.5 mM IBMX, pH=7.4) containing 0.01 µCi [$^3$H]cAMP (Amersham, 1.04 TBq/mmol, 1 µCi/µl, product no.: TRK304). 200 µl of the same buffer containing a 1:16 diluted porcine adrenal gland bark extract (prepared as described by Nordstedt and Fredholm, 1990) were added and the microtitre plates were incubated for at least 2 hours at 4° C. A standard curve was prepared in the same manner with dilutions of cAMP covering the range 2 µM -0.5 nM.

After completion of incubation the solutions were filtered over GF-B glassfibre filters (Whatman) and washed briefly with ca. 2 ml ice-cold washing buffer (50 mM Tris-Cl, pH=7.4). Radioactivity on the filters was measured after-addition of scintillation liquid. Stimulation experiments were determined in quadruplicates and standard curves in duplicates.

Results of Tests of MS05 and MSO9 on cAMP Formation in the MC1-receptor Expressing Cells The magnitude of stimulation of cAMP formation in the treated MC1-receptor expressing cells compared to the cAMP content in untreated control cells were tested for 10 nM and 1 µM MS05 and MS09, and were as given in the below table. For comparison the stimulation obtained by NDP-MSH, α-MSH, forskolin and MS04 (Szardenings et al. 1997) is also given.

| Compound | | Fold stimulation of cAMP | % of 10 nM α-MSH |
|---|---|---|---|
| NPD-MSH | (10 nM) | 7.4 ± 0.7 | 123% |
| NPD-MSH | (1 µM) | 5.9 ± 0.4 | |
| α-MSH | (10 nM) | 6.2 ± 0.7 | 100% |
| α-MSH | (1 µM) | 5.0 ± 0.6 | |
| MS04 | (10 nM) | 1.0 ± 0.1 | 0% |
| MS04 | (1 µM) | 4.6 ± 0.4 | |
| MS05 | (10 nM) | 4.6 ± 0.3 | 69% |
| MS05 | (1 µM) | 6.7 ± 0.3 | |
| MS09 | (10 nM) | 5.5 ± 0.9 | 89% |
| MS09 | (1 µM) | 7.0 ± 0.4 | |
| Forskolin | (1 µM) | 7.3 ± 1.1 | |
| Control | | 1 | |

In the above table the foldness of stimulation (compared to untreated control cells) is shown as the mean ± standard deviation of 3 independent experiments. Shown is also the ability of 10 nM of a compound to stimulate cAMP calculated in percent (%) of the capacity of 10 nM of α-MSH to induce stimulation of cAMP. It is evident from the above table that both MS05 and MS09 are effective stimulators of cAMP formation at both 10 nM and 1 µM concentration. Note that the MS04 peptide is completely devoid of effect on cAMP at 10 nM and 1 µM of MS04 is required to induce stimulation of cAMP formation. Both MS05 and MS09 are highly effective stimulators of cAMP at 10 nM.

EXAMPLE 4

Demonstration of the Capacity of the Compounds of the Invention to Bind to Melanocortin (MSH) Receptors in Mouse B16 Melanoma Cells Cell Culture B16 mouse melanoma cells (B16-Fl; CR6323, American Type Culture Collection, 12301 Parklawn Drive, Rockville, Md., 20852) were cultured in Dulbecco's modified Eagle medium (DMEM; Gibco BRL, Gaithersburg, USA, cat no. 041-01966H) supplemented with 10% heat inactivated fetal bovine serum, 100 IU penicillin/ml and 100 microgram streptomycin/ml at 37° C. in a humidified atmosphere of 95% air and 5% $CO_2$. Cells grown in monolayers were detached from the culture flasks using Hank's balanced salts containing 0.5 mM EDTA and collected by low speed centrifugation (700× g).

Receptor Binding Studies

Assays for MSH-receptor binding was done essentially as described (Xia et al., Cancer Letters, 1996, 98, 157-162), in principle according to earlier described methods (Eberle et al., J. Recept. Res. 1991, 11, 311-322). In brief, collected cells were washed with binding buffer (for composition of binding buffer see below) distributed into 96 well plates and sedimented onto the well bottoms by centrifugation. The cells were then incubated for 2 h at 37° C., with 0.1 ml binding buffer in each well, the buffer containing [$^{125}$I][Nle$^4$, D-Phe$^7$] α-MSH (0.2 nM), different concentrations of the test compound in different wells at 37° C. in binding buffer of the following composition MEM (MEM=Minimum Essential Medium, Gibco BRL, Gaithersburg, USA, cat no.041-01095H) with Eagle's salts, 25 mM Hepes, pH 7.4, 0.2% bovine serum albumin, 1 mM 1,10-phenanthroline, 0.5 microgram leupeptin/ml and 200 microgram bacitracin/ml. After incubation the plates were put on ice, centrifuged and the cells washed with 0.1 ml of ice-cold binding buffer, centrifuged and the binding buffer was sucked off. The finally sedimented and washed cells were then detached from the plates with 0.2 ml of 0.1 N NaOH. Radioactivity was counted by using a Wallac, Wizard automatic gamma counter. The competition data were analysed by law of massaction computer modelling essentially as described (Bergstrom & Wikberg, Acta Pharmacol. Toxicol. 1986, 59, 270-278).

Results

Figure 2:
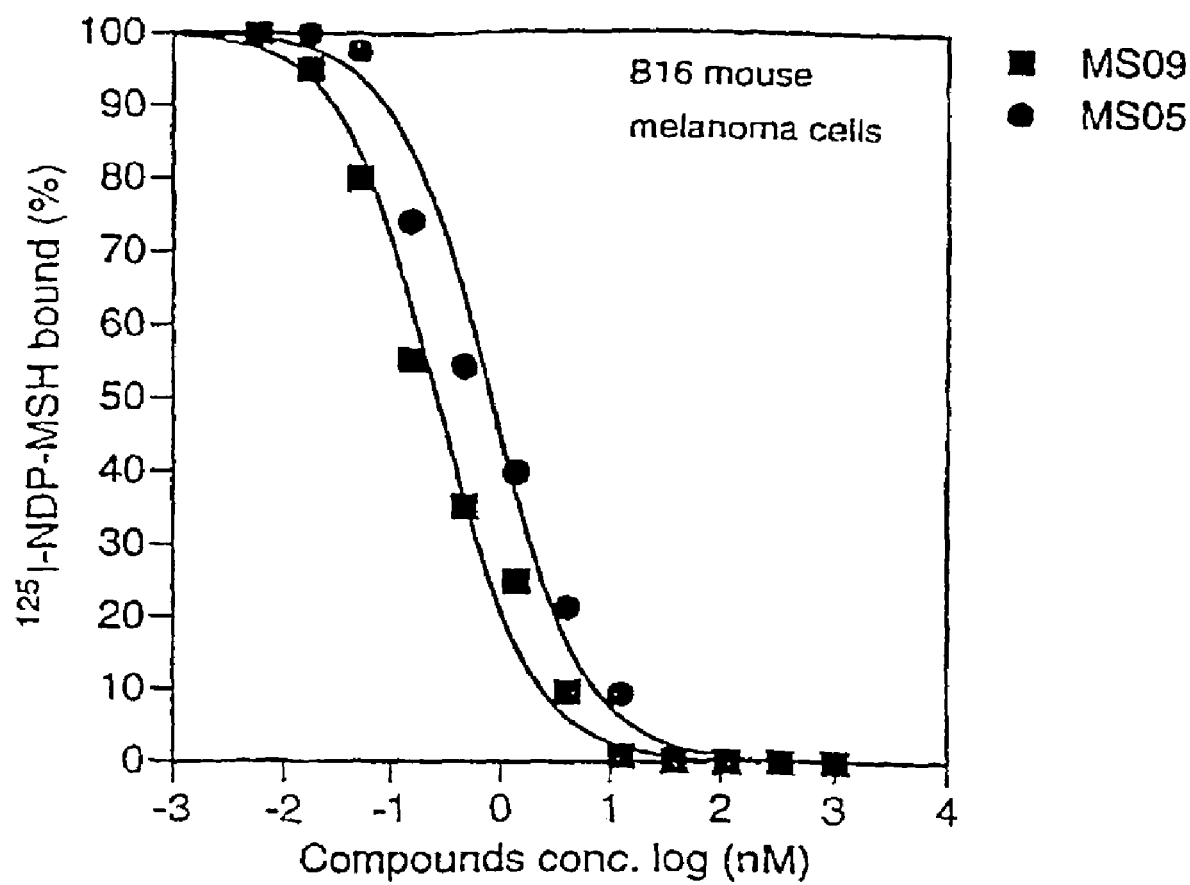
FIG. 2: Inhibition of the binding of [$^{125}$I]-NDP-MSH to B16 melanoma cells by MS05 and MS09.

As is seen from FIG. 2 both the MSO5 and the MSO9 peptide caused a dose dependent inhibition of the binding of [$^{125}$I]-NDP-MSH to the B16 melanoma cells. Analysis of data by law of massaction computer modelling indicated that the MSO5 and MSO9 peptides competed with [$^{125}$I]-NDP-MSH at one single class of binding site (i.e. the B16 melanoma cell MSH-receptor; in other words the native mouse MC1-receptor). The $K^i$ of MSO5 for the mouse B16 melanoma cell MSH-receptor was estimated to be 1.00±0.11 nM (mean ±SEM; n=2). The $K_i$ of MSO9 for the mouse B16 melanoma cell MSH receptor was estimated to be 0.060±0.0035 nM (mean±SEM; n=).

EXAMPLE 5

Demonstration of the Capacity of the Compounds of the Invention to Afford Stimulation of cAMP-formation in Mouse B16 Melanoma Cells Cell Culture B16 mouse melanoma cells (B16-F1; CRL-6323, American Type Culture Collection, 12301 Parklawn Drive, Rockville, Md., 20852), were cultured in Dulbecco's modified Eagle medium (DMEM; Gibco BRA Gaithersburg, USA, cat no. 041-01966H) supplemented with 10% heat-inactivated fetal bovine serum, 100 IU penicillin/mL and 100 µg streptomycin/mL at 37° C. in a humidified atmosphere of 95% air and 5% $CO_2$. Cells grown in monolayers were detached from 60-80% confluent adherent cultures using Hank's balanced salts containing 0.5 mM EDTA and collected by low speed centrifugation (700×g).

Stimulation of Cell cAMP

The cells were incubated for 30 min at 37° C. in DMEM containing 0.5 mM of the phosphodiesterase inhibitor 3-isobutyl-1-methyl-xanthine (IBMX). 20 µL aliquots of appropriate dilutions of test compounds in growth medium were prepared in 96 well microtitre plates The plates were then placed in a water bath at 37° C. and about 1.5×10$^5$ cells in 180 µL were quickly added to each well to obtain immediate mixing. After 20 min, 20 µL 4.4 M perchloric acid was added to each well with mixing, and after a few minutes 20 µL base (5 M KOH, 1 M Tris) was added to each well, whereafter the plates were centrifuged, and the supernatants collected.

Determination of cAMP Concentrations

Twenty µL of the above supernatants were mixed with 50 µL cAMP assay buffer (100 mM Tris-Cl, 250 mM NaCl, 10 mM EDTA, 0.1% mercaptoethanol, 0.5 mM IBMX, pH 7.4) containing 0.01 µCi [$^3$H] cAMP (Amersham, 1.04 TBq/mmol, 1 µCi/µL, product no.: TRK304) in 96-microtiter plate wells. 200 µL of cAMP assay buffer containing a 1:16 diluted porcine adrenal gland bark extract (prepared as described by Nordstedt and Fredholm, Anal. Chem. 1990, 189, 231-234) was then added into each well, and the microtitre plates were incubated for at least 2 hours at 4° C. A standard curve was prepared by exchanging the supernatants with cAMP standards covering the concentration range 2 µM -0.5 nM of final cAMP in the assays.

After completion of the incubations the solutions were rapidly filtered onto GF-B glassfibre filters (Whatman), followed by rapid washing of filters with 2 ml ice-cold washing buffer (50 mM Tris-Cl, pH 7.4). Filters were then placed into scintillation vials and a scintillation cocktail was added. Radioactivity was counted using a β-counter. Cell experiments were determined in quadruplicates and standard curves in duplicates.

Results

Figure 3:
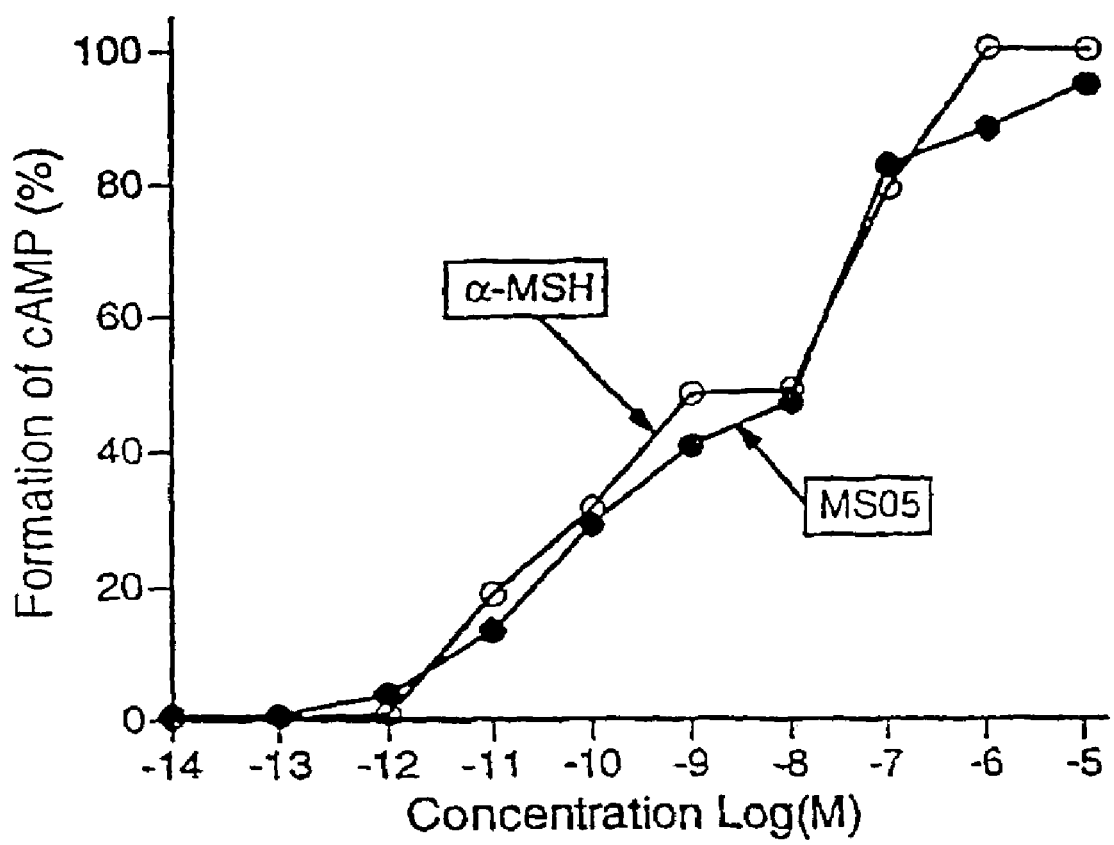
FIG. 3: Stimulation of cAMP-formation in mouse B16 melanoma cells by α-MSH and MS05.

The results from the test of α-MSH and MSO5 peptide on cAMP levels in mouse B16 melanoma cells is shown in FIG. 3. As can be seen from the figure, both peptides caused a marked increase in cAMP at similar potencies and efficacies.

EXAMPLE 6

Demonstration of the Capacity of the Compounds of the Invention to Bind to Melanocortin (MSH) Receptors in RAW264.7 Macrophage Cells.

Cell Culture

RAW 264.7 cells (TIB-71) were obtained from American Type Culture Collection, 12301 Parklawn Drive, Rockville, Md., 20852, USA, and cultured in Dulbecco's modified Eagle medium (DMEM; Gibco BRL, Gaithersburg, USA, cat no. 041-01966H) supplemented with 10% heat-inactivated fetal bovine serum, 100 IU penicillin/ml and 100 µg streptomycin/ml at 37° C. in a humidified atmosphere of 95% air and 5% $CO_2$. Cells grown in monolayers were detached from the culture flasks and collected by low speed centrifugation (700×g).

Receptor Binding Studies

MSH-receptor binding was done essentially as described (Xia et al., Cancer Letters, 1996, 98, 157-162), in principle according to earlier described methods (Eberle et al., J. Recept Res. 1991, 11, 311-322). In brief, the collected cells were washed, distributed into 96 well plates and sedimented onto the well bottoms by centrifugation. The cells were then incubated for 2 h at 37° C., with 0.1 ml binding buffer in each well containing [($^{125}$I][Nle$^4$, D-Phe$^7$] α-MSH (0.1 nM), different concentrations of the test compound in different wells at 37° C. in MEM (Minimum Essential Medium) with Eagle's salts, 25 mM Hepes, pH 7.4, 0.2% bovine serum albumin, 1 mM 1,10-phenanthroline, 0.5 microgram leupeptin/ml and 200 microgram bacitracin/ml. After incubation the plates were put on ice, centrifuged and the cells washed with 0.1 ml of ice-cold binding buffer, centrifuged and the binding buffer was sucked off. The finally sedimented and washed cells were then detached from the plates with 0.2 ml of 0.1 N NaOH. Radioactivity was counted by using a Wallac, Wizard automatic gamma counter. The competition data were analysed by law of massaction computer modelling essentially as described (Bergstrom & Wikberg, Acta Pharmacol. Toxicol. 1986, 59, 270278).

Results

Figure 4:
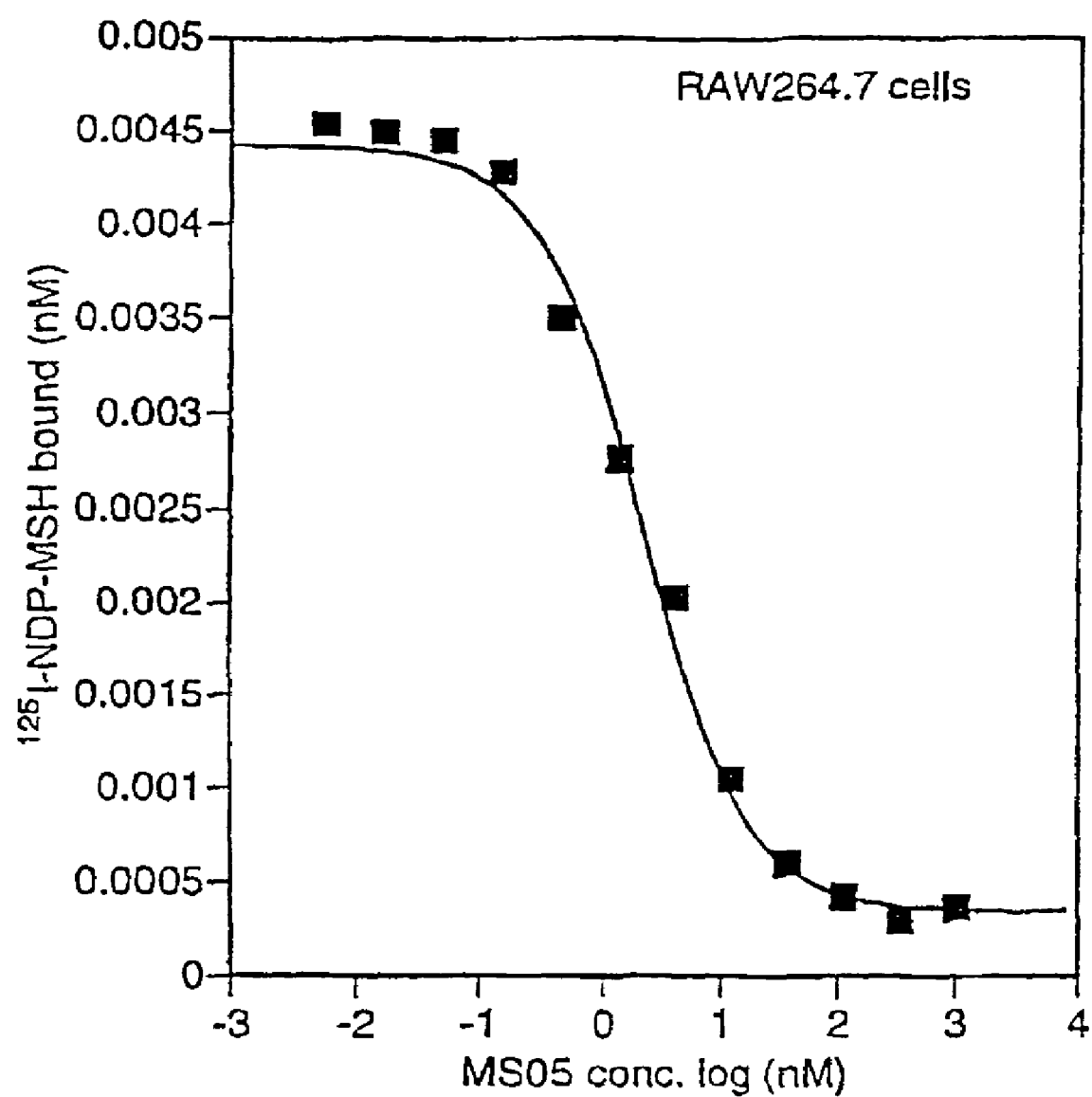
FIG. 4: Inhibition of the binding of [$^{125}$I]-NDP-MSH to mouse RAW 264.7 cells by MS05.

As is seen from FIG. 4, the MSO5 peptide caused a dose dependent inhibition of the binding of [$^{125}$I]-NDP-MSH to the mouse RAW 264.7 cells. Analysis of data by law of massaction computer modelling indicated that MSO5 competed with [$^{125}$I]-NDP-MSH at one single class of binding site (i.e. the RAW 264.7 cell MSH-receptor, which in other words is the native mouse MC1 receptor of the RAW 264.7 cells). The dissociation constant ($k_i$) of MSO5 for the binding site was estimated to be 1.35±0.61 nM (mean±SEM).

EXAMPLE 7

Figure 5:
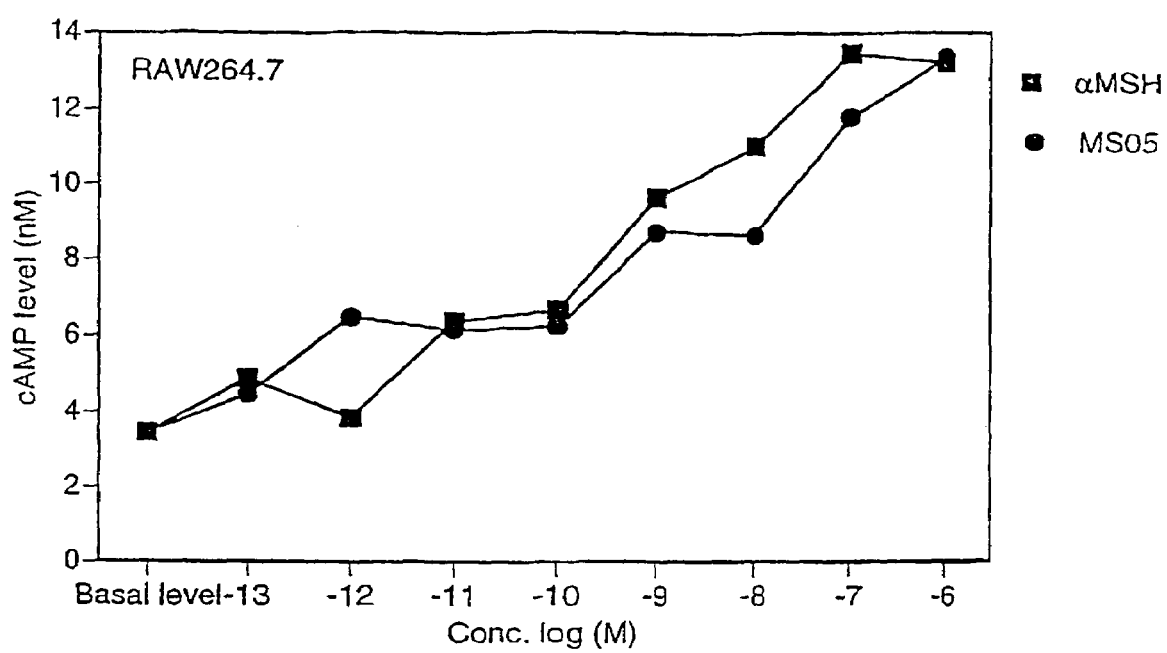
FIG. 5: Stimulation of cAMP-formation in mouse RAW 264.7 cells by α-MSH and MS05.

Demonstration of the Capacity of the Compounds of the Invention to Afford Stimulation of cAMP-formation in Mouse RAW 264.7 Macrophage Cells RAW 264.7 cells were grown as described in Example 6. cAMP was determined essentially as described in Example 5. Results for α-MSH and MSO5 peptide are shown in FIG. 5. As can be seen from the Figure, both peptides caused a marked increase in cAMP at similar potencies and efficacies.

EXAMPLE 8

Demonstration of the Capacity of the Compounds of the Invention to Inhibit Nitric Oxide Production in Mouse RAW264.7Macrophage Cells.

Cell Culture

RAW 264.7 cells (TIB-71), obtained from American Type Culture Collection, 12301 Parklawn Drive, Rockville, Md., 20852, USA, and cultured in Dulbecco's modified Eagle medium (Gibco, BRL) supplemented with 10% heat-inactivated fetal bovine serum, 100 IU penicillin/ml and 100 µg streptomycin/ml at 37° C. in a humidified atmosphere of 95% air and 5% $CO_2$. Cells grown in monolayers were detached from the culture flasks and collected by low speed centrifugation (700×g).

Incubation of Compounds of the Invention with RAW 264.7 Cells

The cells obtained as above were resuspended in F-12 (HAM) medium (Gibco, BRL) and distributed into 96-well plates at a density of $2.5 \times 10^6$ cells per well, and incubated with 100 ng/mL bacterial lipopolysaccharide (L4391, Sigma Chemical Company, P.O. Box 14508, St. Louis, Mo. 63178, USA), 5 units/mL of mouse recombinant interferon gamma (I-5517, Sigma Chemical Company, P.O. Box 14508, St Louis, Mo. 63178, USA) and the compounds of the invention using concentrations ranging 0-1 µM, for 16 h, whereafter an aliquot of the medium was collected for measurement of nitric oxide (NO).

Measurement of Nitric Oxide

Nitric oxide was measured by monitoring the nitrite production essentially using the method of Wishnok et al. (Methods in Enzymology, 1996, 268, 130-151). In brief 50 µL of culture medium was mixed with 50 µL Griess reagent (i.e. a 1:1 mixture of 0.1% N-naphthylethylenediamine dihydrochloride and 1% sulfanilamide in 5% (v/v) phosphoric acid) and after 10 min the absorption was measured at 540 nm. The nitrite concentrations were calculated from a standard curve constructed, by instead of culture medium, adding 50 µL of between 3 to 100 µM of $NaNO_2$ to the assays.

Results

Figure 6:
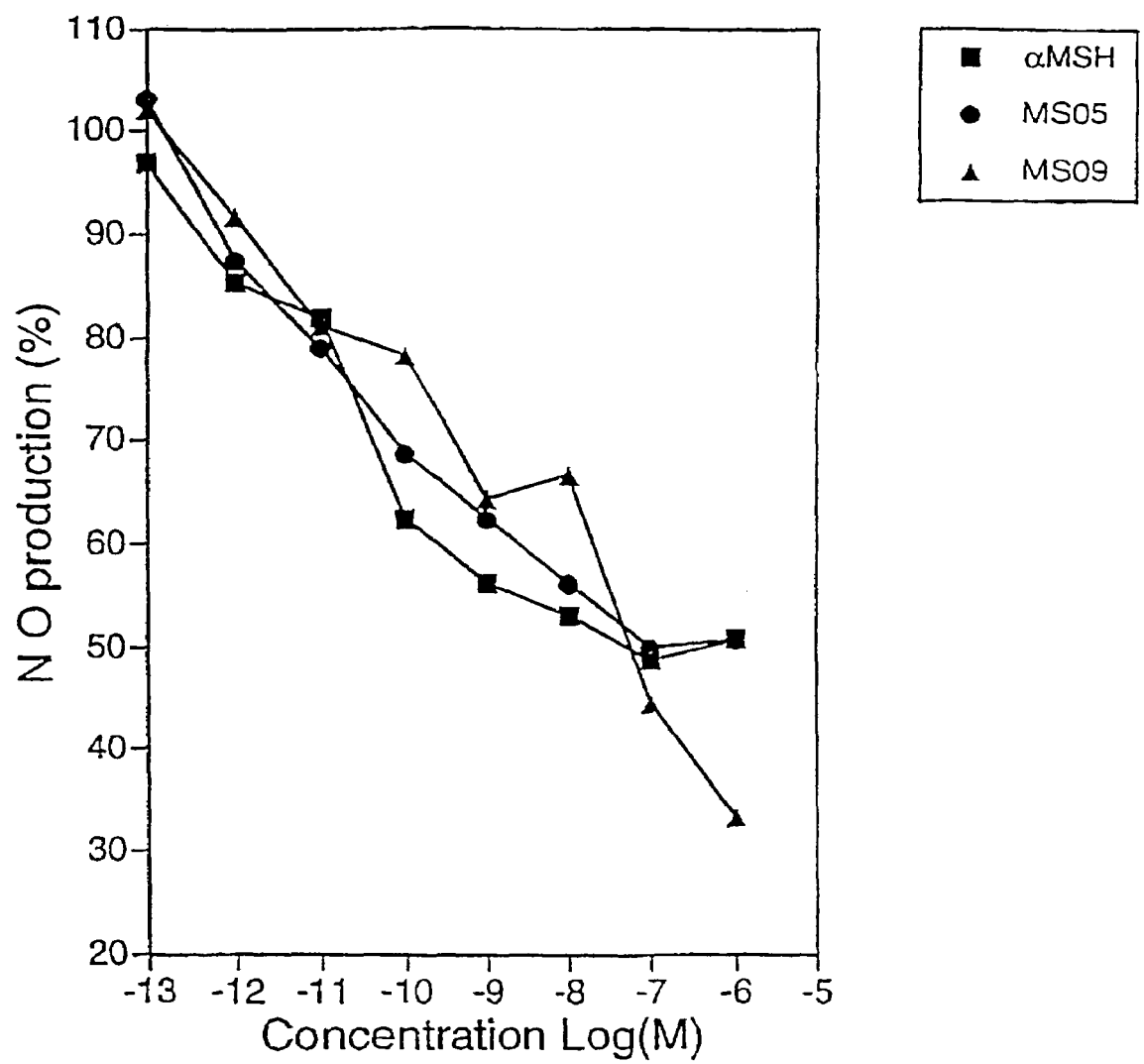
FIG. 6: Inhibition of nitric oxide production in mouse RAW 264.7 cells by α-MSH, MS05 and MS09.

The results are shown in FIG. 6. As can be seen from the Figure, the compounds of the invention, MSO5 and MSO9, as well as α-MSH caused, a strong dose dependent inhibition of the NO-production, the potencies and efficacies of MSO5 and MSO9 being similar to that of the α-MSH. This data shows that MSO5 and MSO9 share the capacity of α-MSH to inhibit inflammation. This is because NO is a key component of inflammation.

REFERENCES

Adan, R A H, Oosterom J, Ludviksdottir G, Brakkee J H, Burbach J P H, Gispen W H, 1994, Identification of antagonists for melanocortin MC3, MC4 and MC5 receptors. Eur. J. Pharmacol. 269, 331.

Bagutti, C, Stoltz B, Albert R, Bruns C, Pless J & Eberle A N: [$^{111}$In]-DTPA-labeled analogues of α-melanocyte stimulating hormone for melanoma targeting: Receptor binding in vitro and in vivo. Int. J. Cancer 1994, 58, 749-755.

Barrett P, MacDonald A, Helliwell R, Davidsson G & Morgan P: Cloning and expression of a member of the melanocyte-stimulating hormone receptor family. J. Mol. Endocrinology. 1994, 12, 203-213.

Bhardwaj, R D, Schwarz E, Mahnke K, Reimann H, Aragane Y, Scwartz T & Luger T A: Pro-opiomelanocortin-derived peptides induce IL-10 production in human monoytes. J. Immunol. 1996,156, 2517.

Boyfield, I, Winn F & Coldwell M: Comparison of agonist potencies at human dopamine D2 and D3 receptors, expressed in the same cell line, using the Cytosensor Microphysiometer. Biochem. Soc. Trans. 1996, 24, 57S.

Campbell, M. J.: Lipofection reagents prepared by a simple ethanol injection technique. Biotechniques 1995, 18, 1027-32.

Canevari, S, Mezzanzanica D, Mazzoni A, Negri D R, Ramakrishna V, Bolhuis R L, Colnaghi M I & Bolis G: Bispecific antibody targeted T cell therapy of ovarian cancer: clinical results and future directions. J. Hematother. 1995, 4, 423-427.

Catania, A, Rajora A, Capsoni F, Minonzio F, Star R A & Lipton J M: The neuropeptide alpha -MSH has specific receptors on neutrophils and reduces chemotaxis in vitro. Peptides 1996, 17, 675679.

Chen, W, Shields T S, Stork P J & Cone R D: A colorimetric assay for measuring activation of $G_s$- and $G_q$-coupled signaling pathways. Anal Biochem. 1995, 226, 349-54.

Chhajlani, V, 1996, Distribution of cDNA for melanocortin receptor subtypes in human tissues, Biochem. Biophys. Res. Commun. 38, 73-80.

Chhajlani, V and Wikberg J E S, 1992, Molecular cloning and expression of the human melanocyte stimulating hormone receptor cDNA, FEBS Lett. 309, 417.

Chhajlani, V, Muceniece R and wikberg J E S, 1993, Molecular cloning of a novel human melanocortin receptor, Biochem. Biophys. Res. Commun. 195, 866.

Chluba-De-Tapia, J, Bagutti C, Cotti R, Eberle A N: Induction of constitutive melanogenesis in amelanotic mouse melanoma cells by transfection of the human melanocortin-1 receptor gene. J. Cell Science 1996, 109, 2023-2030.

Cone, R D, Lu D, Koppula S, Vage D I, Klungland H, Boston B, Chen W, Orth D N, Pouton C & Kesterson R A: The melanocortin receptors: agonists, antagonists, and the hormonal control of pigmentation. Recent Prog Horm Res. 1996, 51,287-317;.

Desarnaud, F, Labbé O, Eggerickx D, Vassart G & Parmentier M: Molecular cloning, functional expression and pharmacological characterization of a mouse melanocortin receptor gene. Biochem J. 1994, 299, 367-373.

De Wied, D and Jolles J, 1982, Neuropeptides derived from pro-opiocortin: Behavioral, physiological, and neurochemical effects, Physiol. Rev. 62, 976.

De Wildt, D J, Kasbergen C M & Versteeg D H G: Effect of γ2-melanocyte-stimulating hormone on cerebral blood flow in rats. J Cardiovascular Pharmacology 1995, 25, 898-905.

Eberle, A N, 1988, The melanotropins; Chemistry, physiology and mechanisms of Action, (Karger, Basel, Switzerland) p333.

Fan, W, Boston B A, Kesterson R A, Hruby V J & Cone R D: Role of melanocortinergic neurons in feeding and the agouti obesity syndrome. Nature. 1997, 385, 165-168.

Fathi, Z, Iben L G & Parker E M: Cloning, expression, and tissue distribution of a fifth melanocortin receptor subtype. Neurochem Res. 1995, 20, 107-113.

Feng, J D, Dao T & Lipton J M: Effects of preoptic microinjections of α-MSH on fever and normal temperature control in rabbits. Brain Res. 1987, 18, 473-477.

Fruedman, J M: The alphabet of weight control. Nature 1997, 385, 119-120.

Gantz, I, Konda Y, Tashiro T, Shimoto Y, Miwa H, Munzert G, Watson S J, DelValle J and Yamada T, 1993a, Molecular cloning of a novel melanocortin receptor, J. Biol. Chem. 268, 8246.

Gantz, I, Miwa H, Konda Y, Shimoto Y, Tashiro T, Watson S J, DelValle J and Yamada T, 1993b, Molecular cloning, expression, and gene localization of a fourth melanocortin receptor, J. Biol. Chem. 268, 15174.

Gantz, I, Shimoto Y, Konda Y, Miwa H, Dickinson C J & Yamada T: Molecular cloning, expression, and characterization of fifth melanocortin receptor. Biochem. Biophys. Res. Commun. 1994, 200,1214-1220.

Garrud, P, Gray J A & DeWied D: Pituitary-adrenal hormones and extinction of rewarded behavior in the rat. Physiol Psychol. 1974, 112,109-119.

Goninard, C, Goigoux C, Hollande L D & D'Hinterland L D: The administration of an alpha-MSH analogue reduces the serum release of IL-1 alpha and TNF alpha induced by the injection of a sublethal dose of lipopolysaccharides in the BALB/c mouse. Pigment Cell Res. 1996, 9, 148-153.

Griffon, N, Mignon V, Facchinetti P, Diaz J, Schwartz J-C & Sokoloff P: Molecular cloning and characterization of the fifth melanocortin receptor. Biochem. Biophys. Res. Commun. 1994, 200, 1007-1014.

Gruber, K A & Callahan M F: ACTH(4-10) through y-MSH: Evidence for a new class of central autonomic nervous system-regulating peptides. Am. J. Physiol. 1989, 257, R681-R694.

Hartmeyer, M, Scholzen T, Becher E, Bhardwaj R S, Schwartz T & Luger T A: Human dermal microvascular endothelial cells express the melanocortin receptor type 1 and produce levels of IL upon stimulation with alpha-melanocyte stimulating hormone. J. Immunol. 1997,159, 1930-1937.

Hnatowich, M R, Queen G, Stein D & Labella F S: ACTH receptors in nervous tissue. High affinity binding-sequestration of [125I](Phe2, Nle4)ACTH 1-24 in homogenates and slices from rat brain. Can. J. Physiol. Pharmacol. 1989, 67, 568-576.

Hol, E M, Sodaar M P, Gispen W H & Bär P R: Protection by an ACTH4-9 analogue against the toxic effect of cisplatin and taxol on sensory neurons and glial cells in vitro. J. Neurosci. Res. 1994, 39, 178-185.

Hruby, V J, Lu E, Sharma S D, Castrucci A L, Kesterson R A, Al-Obeidi R A, Hadley M E and Cone R D, 1995, Cyclic lactam a-melanotropin analogues of Ac-Nle$^4$-cyclo(Asp$^5$, D-Phe$^7$, Lys$^{10}$) α-melanocyte-stimulating hormone(4-10)-NH$_2$ with bulky aromatic amino acids at position 7 show high antagonist potency and selectivity at specific melanocortin receptors, J. Med. Chem. 38, 3454.

Knittel, J J, Sawyer T K, Hruby, V J and Hadley, M E (1983) Structure-activity studies of highly potent [Cys$^4$, Cys$^{10}$] melanotropin analogues, J. Med. Chem. 28, 125-129.

Klein, M C, Hutchins P M, Lymangrover J R & Gruber K A: Pressor and cardioaccelerator effects of gamma MSH and related peptides. Life Sciences 1985, 36, 769-775.

Labbé, O, Desarnaud F, Eggerickx D, Vassart G & Parmentier M: Molecular cloning of a mouse melanocortin 5 receptor gene widely expressed in peripheral tissues. Biochemistry 1994, 33, 4543-4549.

Lichtensteiger, W, Hanimann B, Schlumpf M, Siegrist W & Eberle A N. Pre- and postnatal ontogeny of [125]Nle4, D-Phe7-alpha-MSH binding sites in rat brain. Ann N. Y. Acad. Sci. 1993, 680, 652-654.

Lin, S Y, Chaves C, Wiedemann E & Humphreys M H: A γ-melanocyte stimulating hormone-like peptide causes reflex natriuresis after acute unilateral nephrectomy. Hypertension 1987, 10, 619-627.

Lipton, J M & Catania A: Anti-inflammatory actions of the neuroimminomodulator α-MSH. Immunology Today 1997, 18, 140-145.

Low, M J, Simerly R B, Cone R D, 1994, Receptors for the melanocortin peptides in the central nervous system, Curr. Opin. Endocr. Diab. 79

Luger, T A, Scholzen T & Grabbe S: The role of alpha-melanocyte-stimulating hormone in cutaneous biology. J. Invest Dermatol. Symp. Proc. 1997, 2, 87-93.

Mountjoy, K G, Robbins L S, Mortrud M T and Cone R D, 1992, The cloning of a family of enes that encode the melanocortin receptors, Science 257, 1248.

Mountjoy, K G, Mortrud M T, Low M J, Simerly. R B & Cone R D: Localization of the melanocortin-4 receptor (MC4-R) in endocrine and autonomic control circuits in the brain. Molecular Endocrinology 1994, 8, 1298-1308.

Mukherii, B & Chakraborty N G: Immunobiology and immunotherapy of melanoma. Curr. Opin. Oncol. 1995, 7, 159-161.

Murphy, J R, Bishai W, Borowski M, Miyanohara A, Boyd J & Nagle S: Genetic construction, expression, and melanoma-selective cytotoxicity of a diphtheria toxin-related alpha-melanocyte-stimulating hormone fusion protein. Proc. Natl. Acad. Sci. USA. 1986, 83, 8258-8262.

Nordstedt, C, Fredholm B B.: A modification of a protein-binding method for rapid quantification of cAMP in cell-culture supernatants and body fluid. Anal. Biochem. 1990, 189, 231-234.

O'Donahue, T L, Handelmann G E, Loh Y P, Olton D S, Leibowitz J & Jacobowitz D M: Comparison of biological and behavioral activities of alpha- and gamma melanocyte stimulating hormones. Peptides 1981, 2, 101-104.

O'Donahue, T L, & Dorsa D M: The opiomelanotropinergic neuronal and endocrine systems. Peptides 1982, 3, 353-395.

O'Hare, K B, Duncan R, Strohalm J. Ulbrich K & Kopeckova P: Polymeric drug-carriers containing doxorubicin and melanocyte-stimulating hormone: in vitro and in vivo evaluation against murine melanoma. J Drug Target 1993, 1, 217-229.

Prusis, P, Frändberg P A, Muceniece R, Kalvinsh I and Wikberg J E S, 1995, A three dimentional model for the interaction of MSH with the melanocortin 1 receptor, Biochem. Biophys. Res. Commun. 210, 205.

Rajora, N, Boccoli G, Burns D, Sharma S, Catania A P & Lipton J M: Alpha-MSH modulates local and circulating tumour necrosis factor-alpha in experimental brain inflammation. J. Neurosci. 1997a,-17, 2181-2186.

Rajora, N, Boccoli G, Catania A & Lipton J M: Alpha-MSH modulates experimental inflammatory bowel disease. Peptides 1997b, 18, 381-385.

Riedle, S, Rosel M & Zoller M: In vivo activation and expansion of T cells by a bi-specific antibody abolishes metastasis formation of human melanoma cells in SCID mice. Int. J. Cancer 1998, 75, 908-918.

Roselli-Rehfuss, L, Mountjoy K G, Robbins L S, Mortrud M T, Low M J, Tatro J B, Entwistle M L, Simerly R B and Cone R D: Identification of a receptor for g melanotropin and other proopiomelanocortin peptides in the hypothalamus and limbic system. Proc. Natl. Acad. Sci. USA 1993, 90, 8856-8860.

Sawyer, T K, San Filippo P J, Hruby V J, Engel M H, Heward C B, Burnett J B & Hadley M E: 4-Norleucine, 7-phenylalanine-a-melanocyte-stimulating-hormone: A highly potent a-melanotropin with ultralong biological activity. Proc. Natl. Acad. Sci. USA 1980, 77, 5754-5758.

Sawyer, T K, Hruby V J, Darman P S and Hadley M E (1982) [half-Cys$^4$, half-Cys$^{10}$]-α-melanocyte stimulating hormone; A cyclic α-melanotropin exibiting superagonist biological activity, Proc. Natl. Acad. Sci. USA 79, 1751-1755.

Schiöth, H B, Muceniece R, Wikberg J E S and Chhajlani V, 1995, Characterisation of melanocortin receptor subtypes by-radioligand binding analysis, Eur. J. Pharmacol., Mol. Pharm. Sect. 288, 311.

Schiöth, H B, Kuusinen A, Muceniece R, Szardenings M, Keinänen K and Wikberg J E S, 1996a, Expression of functional melanocortin 1 receptors in insect cells, Biochem. Biophys. Res. Commun. 221, 807.

Schiöth, H B, Muceniece R and Wikberg J E S, 1996b, Characterisation of melanocortin 4 receptor by radioligand binding analysis. Pharmacol. & Toxicol. 79, 161.

Schiöth, H B, Chhajlani V, Muceniece R, Klusa V and Wikberg J E S, 1996c, Major pharmacological distinction of the ACTH receptor from the other melanocortic receptors, Life Sciences 59, 797.

Solca, F F, Chluba-de-Tapia J, Iwata K, Eberle A N: B16-G4F mouse melanoma cells: an MSH receptor-deficient cell clone. Febs Lett. 1993, 322, 177-80.

Siegrist, W and Eberle A N, 1995, Melanocortins and their implications in melanoma, TEM, 6, 115.

Simpson, E R and Waterman M R, Regulation of the synthesis of steroidogenic enzymes in adrenal cortical cells by ACTH. (1988) Ann. Rev. Physiol. 50, 427-440.

Star, R A, Rajora N, Huang J, Stock R C, Catania A & Lipton J M: Evidence of autocrine modulation of macrophage nitric oxide synthase by α-melanocyte-stimulating hormone. Proc. Natl. Acad. Sci. USA 1995, 92, 8016-8020.

Szardenings, M, Tomroth S, Mutulis F, Muceniece R, Keinanen K, Kuusinen A, Wikberg J E: Phage display selection on whole cells yields a peptide specific for melanocortin receptor 1. J. Biol. Chem. 1997, 272, 27943-27948.

Tatro, J B, Wen Z, Entwistle M L, Atkins M B, Smith T J, Reichlin S & Murphy J R: Interaction of an alpha-melanocyte-stimulating hormone-diphtheria toxin fusion protein with melanotropin receptors in human melanoma metastases. Cancer Res. 1992, 52, 2545-2548.

Tatro, J and Entwistle M L, 1994, Heterogeneity of brain melanocortin receptors suggested by differential ligand binding in situ., Brain Research 635, 148.

Tatro, J B and Reichlin S, 1987, Specific receptors for α-melanocyte-stimulating hormone are widely distributed in tissues of rodents, Endocrinology 121, 1900.

Thielemans, K M: Immunotherapy with bispecific antibodies. Verh. K. Acad. Geneeskd. Belg. 1995, 57, 229-247.

Thömvall, M, Dimitrou A, Xu X, Larsson E & Chhajlani V: Immunohistochemical detetion of the melanocortin 1 receptor in human testis, ovary and placenta using specific monoclonal antibody. Horm. Res. 1997, 48, 215-218.

Vanetti, M, Schönrock C, Meyerhof W & Höllt V: Molecular cloning of a bovine MSH receptor which is highly expressed in the testis. FEBS Left. 1994, 348, 268-272.

Wiegant, V M, Jolles J, Colbem D L, Zimmermann E and Gispen W H: Intracerebroventricular ACTH activates the pituitary-adrenal system: Dissociation from a behavioral response. Life Sci. 1979, 25, 1791-1796.

Wong, K Y, Rajora R, Boccoli G & Lipton J M: A potential mechanism of local anti-inflammatory action of alpha-melanocyte stimulating hormone within the brain: modulation of tumour necrosis factor-alpha production by human astrocytic cells. Neuroimmunomodulation 1997, 4, 37-41.

Xia, Y, Wikberg J E S & Chhajlani V: Expression of melanocortin 1 receptor in periaqueductal gray matter. Neuroreport. 1995, 6, 2193-2196.

Sequence Listing Free Text

<210>1
<223>Description of Artificial Sequence: Synthetic peptide with high affinity for melanocortin receptor 1
<210>2
<223>Description of Artificial Sequence: Synthetic peptide with high affinity for melanocortin receptor 1
<221>MOD$_{13}$RES
<222>(7)
<223>D amino-acid
<210>3
<223>Description of Artificial Sequence: Synthetic peptide with high affinity for melanocortin receptor 1
<210>4
<223>Description of Artificial Sequence: Synthetic peptide with high affinity for melanocortin receptor 1
<210>5
<223>Description of Artificial Sequence: Synthetic peptide with high affinity for melanocortin receptor 1
<210>6
<223>Description of Artificial Sequence: Synthetic peptide with high affinity for melanocortin receptor 1
<210>7
<223>Description of Artificial Sequence: Synthetic peptide with high affinity for melanocortin receptor 1
<210>8
<223>Description of Artificial Sequence: Synthetic peptide with high affinity for melanocortin receptor 1
<210>9
<223>Description of Artificial Sequence: Synthetic peptide with high affinity for melanocortin receptor 1
<210>10
<223>Description of Artificial Sequence: Synthetic peptide with high affinity for melanocortin receptor 1
<210>11
<223>Description of Artificial Sequence: Synthetic peptide with high affinity for melanocortin receptor 1
<210>12
<223>Description of Artificial Sequence: Synthetic peptide with high affinity for melanocortin receptor 1
<220>
<221>MOD_RES
<222>(1)
<223>D amino-acid
<210>13
<223>Description of Artificial Sequence: Synthetic peptide with high affinity for melanocortin receptor 1
<220>
<221>MOD_RES
<222>(1)
<223>N-methyl-L-serine
<210>14
<223>Description of Artificial Sequence: Synthetic peptide with high affinity for melanocortin receptor 1
<220>
<221>MOD_RES
<222>(13)
<223>N-methyl-L-valine
<210>15
<223>Description of Artificial Sequence: Synthetic peptide with high affinity for melanocortin receptor 1
<220>
<221>MOD_RES
<222>(7)
<223>N-methyl-D-phenylalanine

SEQUENCE LISTING

<160> NUMBER OF SEQ ID NOS: 15

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 1

Ser Ser Ile Ile Ser His Phe Arg Trp Gly Lys Pro Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<220> FEATURE:
<221> NAME/KEY: MOD_RES
<222> LOCATION: (7)..(7)
<223> OTHER INFORMATION: D amino acid

<400> SEQUENCE: 2

Ser Ser Ile Ile Ser His Phe Arg Trp Gly Lys Pro Val
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 3

Tyr Ser Ser Ile Ile Ser His Phe Arg Trp Gly Lys Pro Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide with high affinity for
      melanocoritn receptor 1

<400> SEQUENCE: 4

Tyr Ser Ile Ile Ser His Phe Arg Trp Gly Lys Pro Val
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 5

Ser Ser Ile Ile Ser His Phe Arg Trp Gly Lys Pro Val Tyr
1               5                   10

```
<210> SEQ ID NO 6
<211> LENGTH: 12
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 6

Ser Ile Ile Ser His Phe Arg Trp Gly Lys Pro Val
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 7

Thr Ser Ile Ile Ser His Phe Arg Trp Gly Lys Pro Val
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 8

Ser Thr Ile Ile Ser His Phe Arg Trp Gly Lys Pro Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 9

Ser Ser Val Ile Ser His Phe Arg Trp Gly Lys Pro Val
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1

<400> SEQUENCE: 10

Ser Ser Ile Val Ser His Phe Arg Trp Gly Lys Pro Val
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
```

```
<220> FEATURE:
<221> NAME/KEY: MOD_RES
<222> LOCATION: (1)..(1)
<223> OTHER INFORMATION: ACETYLATION

<400> SEQUENCE: 11

Ser Ser Ile Ile Ser His Phe Arg Trp Gly Lys Pro Val
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<220> FEATURE:
<221> NAME/KEY: MOD_RES
<222> LOCATION: (1)..(1)
<223> OTHER INFORMATION: D amino acid

<400> SEQUENCE: 12

Ser Ser Ile Ile Ser His Phe Arg Trp Gly Lys Pro Val
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<220> FEATURE:
<221> NAME/KEY: MOD_RES
<222> LOCATION: (1)..(1)
<223> OTHER INFORMATION: N-Methyl-L-Serine

<400> SEQUENCE: 13

Ser Ser Ile Ile Ser His Phe Arg Trp Gly Lys Pro Val
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<220> FEATURE:
<221> NAME/KEY: MOD_RES
<222> LOCATION: (13)..(13)
<223> OTHER INFORMATION: MeVal

<400> SEQUENCE: 14

Ser Ser Ile Ile Ser His Phe Arg Trp Gly Lys Pro Val
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide with high affinity for
      melanocortin receptor 1
<220> FEATURE:
<221> NAME/KEY: MOD_RES
<222> LOCATION: (7)..(7)
<223> OTHER INFORMATION: N-Methyl-D-Phenylalanine
```

-continued

```
<400> SEQUENCE: 15

Ser Ser Ile Ile Ser His Phe Arg Trp Gly Lys Pro Val
1               5                   10
```

The invention claimed is:

1. A method for treating an inflammatory disease condition comprising the administration of a pharmacologically effective amount of a compound of general formula (1):

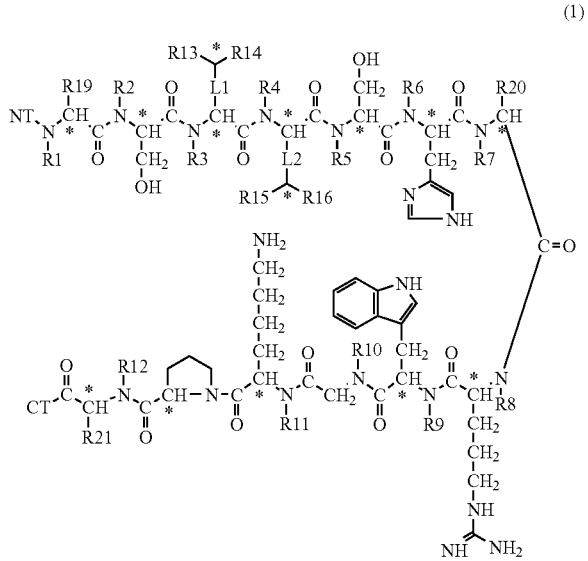

(1)

wherein R1, R2, R3, R4, R5, R6, R7, R8, R9, R10, R11 and R12 are selected independently from H and methyl, and wherein R13, R14, R15 and R16 are selected independently from H and alkyl and wherein optionally one hydrogen in R13 and one hydrogen in R14 is exchanged for a bond between R13 and R14, and wherein optionally one hydrogen in R15 and one hydrogen in R16 is exchanged for a bond between R15 and R16, and wherein L1 and L2 are linkers which are independently selected from the group consisting of single bond, methyl and ethyl, and wherein R19 and R20 are selected independently from H and —$CH_2X$, where X is H, alkyl, substituted alkyl, heteroalkyl, substituted heteroalkyl, alkenyl, substituted alkenyl, heteroalkenyl, substituted heteroalkenyl, alkynyl, substituted alkynyl, heteroalkynyl, substituted heteroalkynyl, cycloalkyl, substituted cycloalkyl, cycloheteroalkyl, substituted cycloheteroalkyl, cycloalkenyl, substituted cycloalkenyl, cycloheteroalkenyl, substituted cycloheteroalkenyl, aryl, substituted aryl, heteroaryl, substituted heteroaryl, functional group Q, wherein Q is selected from the group consisting of amino, alkylamino, dialkylamino, arylamino, arylazido, heteroarylamino, heteroarylazido, hydroxyl, alkylhydroxy, fluorinated alkylhydroxy, cyano, carboxy, alkylcarboxy, arylcarboxy, halogen, nitro, hydroxylamino, acyl, fluorinated acyl, nitroso, sulfonyl, sulfinyl, thio, alkylthio and arylthio, and wherein R21 is selected independently from H, —CH($CH_3$)$_2$, and —$CH_2X$, and wherein NT is selected from H, hydroxyl, alkyl, amino acid, amino acid analogue, polypeptide and functional group Q, and CT is selected from hydrogen, hydroxyl, alkyl, amino acid, amino acid analogue, polypeptide and functional group Q, and wherein each asymmetric center (*) is in R or S configuration, to a patient.

2. A method for treating an inflammatory disease or condition caused by or associated with one or more of the following: allergy, hypersensitivity, inflammation caused by toxic agent, fever, autoimmune disease, radiation damage caused by UV-radiation, X-ray radiation, γ-radiation, α- or β-particles, sun burns, mechanical injury or hypoxia, the method comprising the administration of a pharmacologically effective amount of a compound as defined in claim 1 to a patient.

3. A method for treating an inflammatory skin disease of any origin, the method comprising the administration of a pharmacologically effective amount of a compound as defined in claim 1 to a patient.

4. A method for treating an inflammatory disease in the abdomen, selected from the group consisting of an abdominal disease having an inflammatory component, gastritis, gastritis perniciosa (atrophic gastritis), ulcerous colitis (colitis ulcerosa), morbus Crohn, systemic sclerosis, ulcus duodeni, celiac disease, oesophagitis and ulcus ventriculi, the method comprising the administration of a pharmacologically effective amount of a compound as defined in claim 1 to a patient.

5. A method for treating an inflammatory disease or condition selected from the group consisting of rheumatoid arthritis, psoriatic arthritis, systemic sclerosis, polymyalgia rheumatica, Wegener's granulomatosis, sarcoidosis, eosinophil ic fasceitis, reactive arthritis, Bechterew's disease, systemic lupus erythematosus, arteritis temporalis, Behcet's disease, morbus Burger, Good Pastures' syndrome, eosinophilic granuloma, fibromyalgia, myositis, and mixed connective tissue disease, the method comprising the administration of a pharmacologically effective amount of a compound as defined in claim 1 to a patient.

6. A method for treating an inflammatory disease or condition of the peripheral and central nervous system selected from the group consisting of cerebral vasculitis, multiple sclerosis, autoimmune ophtalmitis and polyneuropathia, the method comprising the administration of a pharmacologically effective amount of a compound as defined in claim 1 to a patient.

7. A method for treating an inflammatory disease or condition of the eye and tear glands selected from the group consisting of anterior and posterior uveitis, retinal vasculitis, otpicus neuritis, Wegener's granulomatosis, Sjögren's syndrome, episcleritis, scleritis, sarcoidosis affecting the eye and polychondritis affecting the eye, the method comprising the administration of a pharmacologically effective amount of a compound as defined in claim 1 to a patient.

8. A method for treating an inflammatory disease or condition of the ear which is polychondritis affecting the ear and/or external otitis, the method comprising the administration of a pharmacologically effective amount of a compound as defined in claim 1 to a patient.

9. A method for treating an inflammatory disease or condition of the nose selected from the group consisting of sarcoidosis, polychondritis and mid-line granuloma of the nose, the method comprising the administration of a pharmacologically effective amount of a compound as defined in claim 1 to a patient.

10. A method for treating an inflammatory disease or condition of the mouth, pharynx and/or salivary gland, selected from the group consisting of Wegener's granulomatosis, mid-line granuloma, Sjögren's syndrome and polychondritis in these areas, the method comprising the administration of a pharmacologically effective amount of a compound as defined in claim 1 to a patient.

11. A method for treating an inflammatory disease or condition in the lung, selected from the group consisting of idiopathic alveolitis, primary pulmonary hypertension, bronchitis, chronic bronchitis, sarcoidosis, alveolitis in inflammatory systemic disease, pulmonary hypertension in inflammatory systemic disease, Wegener's granulomatosis and Good Pastures' syndrome, the method comprising the administration of a pharmacologically effective amount of a compound as defined in claim 1 to a patient.

12. A method for treating an inflammatory disease or condition of the heart, selected from the group consisting of pericarditis, idiopathic pericarditis, myocarditis, Takayasus' arteritis, Kawasaki's disease, coronary artery vasculitis, pericarditis in inflammatory systemic disease, myocarditis in inflammatory systemic disease, endocarditis and endocarditis in inflammatory systemic disease, the method comprising the administration of a pharmacologically effective amount of a compound as defined in claim 1 to a patient.

13. A method for treating an inflammatory disease or condition of the liver, selected from the group consisting of hepatitis, chronic active hepatitis, biliary cirrhosis, hepatic damage by toxic agent, interferon induced hepatitis, hepatitis induced by viral infection, liver damage induced by anoxia and liver damage caused by mechanical trauma, the method comprising the administration of a pharmacologically effective amount of a compound as defined in claim 1 to a patient.

14. A method for treating an inflammatory disease or condition of the endocrine or exocrine pancreas, selected from the group consisting of diabetes mellitus, late complications of diabetes mellitus, acute pancreatitis and chronic pancreatitis, the method comprising the administration of a pharmacologically effective amount of a compound as defined in claim 1 to a patient.

15. A method for treating an inflammatory disease or condition of the thyroid gland, selected from the group consisting of thyreoiditis, autoimmune thyreoiditis, Hashimoto's thyreoiditis, the method comprising the administration of a pharmacologically effective amount of a compound as defined in claim 1 to a patient.

16. A method for treating an inflammatory disease or condition of the kidney, selected from the group consisting of glomerulonephritis, glomerulonephritis in systemic lupus erythematosus, periarteritis nodosa, Wegener's granulomatosis, Good-Pastures' syndrome, HLAb27 associated diseases, IgA nephritis (IgA=Immunoglobuline A), pyelonephritis, chronic pyelonephritis and interstitial nephritis, the method comprising the administration of a pharmacologically effective amount of a compound as defined in claim 1 to a patient.

17. A method for treating an inflammatory disease or condition of the joints selected from the group consisting of Bechterew's disease, psoriatic arthritis, rheumatoid arthritis, arthritis in colitis ulcerosa, arthritis in morbus Grohn, affection of joints in systemic lupus erythematosus, systemic sclerosis, mixed connective tissue disease, reactive arthritis, Reiter's syndrome, arthrosis of any joint, arthrosis of finger joints, arthrosis of the knee and arthrosis of the hip, the method comprising the administration of a pharmacologically effective amount of a compound as defined in claim 1 to a patient.

18. A method for treating an inflammatory disease or condition of blood vessels, selected from the group consisting of arteritis temporalis, periarteritis nodosa, arteriosclerosis, Takayasus' arteritis and Kawasaki's disease, the method comprising the administration of a pharmacologically effective amount of a compound as defined in claim 1 to a patient.

19. A method for treating arteriosclerosis, the method comprising the administration of a pharmacologically effective amount of a compound as defined in claim 1 to a patient.

20. A method for treatment of drug induced disorders of the blood and lymphoid system, selected from the group consisting of drug induced hypersensitivity affecting blood cells and blood cell forming organs, drug hypersensitivity affecting blood cells and blood cell forming organs, anaemia, granulocytopenia, trombocytopenia, leukopenia, aplastic anaemia, autoimmune haemolytic anaemia, autoimmune thrombocytopenia, autoimmune granulocytopenia, the method comprising the administration of a pharmacologically effective amount of a compound as defined in claim 1 to a patient.

21. A method for treating a disease or condition related to fast allergic disorders selected from the group consisting of anaphylactic reactions, anaphylactoid reactions, asthma, asthma of allergic type, asthma of unknown origin, rhinitis, hay fever and pollen allergy, the method comprising the administration of a pharmacologically effective amount of a compound as defined in claim 1 to a patient.

22. A method for treating inflammation secondary to infection, the method comprising the administration of a pharmacologically effective amount of a compound as defined in claim 1 to a patient.

23. A method for treating an inflammatory disease or condition related to trauma and tissue injury of any origin, the method comprising the administration of a pharmacologically effective amount of a compound as defined in claim 1 to a patient.

24. A method for stimulating pigment formation in epidermal cells, the method comprising the administration of a pharmacologically effective amount of a compound as defined in claim 1 to a patient.

25. A method for inhibiting pigment formation in cells of the skin, the method comprising the administration of a pharmacologically effective amount of a compound as defined in claim 1 to a patient.

26. A method for treating an inflammatory disease or condition associated with oedema, wherein the oedema is associated with allergic reactions or inflammation, the method comprising the administration of a pharmacologically effective amount of a compound as defined in claim 1 to a patient.

27. A method for treating an inflammatory disease or condition of the blood vessels or vasculitis, the method comprising the administration of a pharmacologically effective amount of a compound as defined in claim 1 to a patient.

28. The method of claim 1 in which NT is a polypeptide, R1-R12 are hydrogen, R13 and R15 are methyl, R14 and R16 are ethyl, R19 is $CH_2OH$, R20 is $CH_2Ph$, R21 is $CH(CH_3)_2$ and CT is OH.

29. The method of claim 3 in which the skin disease is selected from the group consisting of contact dermatitis of the skin, sunburns of the skin, burns of any cause, inflammation of the skin caused by chemical agent, psoriasis, vasculitis, pyoderma gangrenosum, discoid lupus erythematosus, eczema, pustulosis palmo-plantaris, and phemphigus vulgaris.

30. The method of claim 3 in which the skin disease is eczema.

31. The method of claim 28 in which the disease is eczema.

32. The method of claim 1 in which the compound comprises SEQ ID NO:1.

33. The method of claim 1 in which NT is hydrogen, R1-R12 are hydrogen, R13 and R15 are methyl, R14 and R16 are ethyl, R19 is $CH_2OH$, R20 is $CH_2Ph$, R21 is $CH(CH_3)_2$ and CT is OH.

34. The method of claim 1 in which NT is hydrogen, R1-R12 are hydrogen, R13 and R15 are methyl, R14 and R16 are ethyl, R19 is $CH_2OH$, R20 is $CH_2Ph$, R21 is $CH(CH_3)_2$ and CT is $NH_2$.

35. The method of claim 1 in which NT is a polypeptide, R1-R12 are hydrogen, R13 and R15 are methyl, R14 and R16 are ethyl, R19 is $CH_2OH$, R20 is $CH_2Ph$, R21 is $CH(CH_3)_2$ and CT is $NH_2$.

36. The method of claim 24, which includes skin tanning for cosmetic reasons, skin tanning for treatment of vitiligo or skin tanning for treatment of any other condition where darkening of skin color is desired.

37. The method of claim 22, wherein the inflammation secondary to infection is caused by virus, bacteria, helminths and/or protozoae.

38. The method of claim 20, wherein the blood cells and blood cell forming organs are bone marrow or lymphoid tissue.

39. The method of claim 1 in which the compound comprises SEQ ID NO: 11.

* * * * *